(12) United States Patent
Knox et al.

(10) Patent No.: US 11,974,925 B2
(45) Date of Patent: May 7, 2024

(54) PATIENT SPECIFIC STEMLESS PROSTHESIS ANCHOR COMPONENTS

(71) Applicant: HOWMEDICA OSTEONICS CORP., Mahwah, NJ (US)

(72) Inventors: Kevin P. Knox, Fort Wayne, IN (US); Shawn M. Gargac, Fort Wayne, IN (US); Markus Scheibel, Berlin (DE)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 0 days.

(21) Appl. No.: 16/648,128

(22) PCT Filed: Sep. 21, 2018

(86) PCT No.: PCT/US2018/052294
§ 371 (c)(1),
(2) Date: Mar. 17, 2020

(87) PCT Pub. No.: WO2019/060780
PCT Pub. Date: Mar. 28, 2019

(65) Prior Publication Data
US 2020/0214845 A1 Jul. 9, 2020

Related U.S. Application Data

(60) Provisional application No. 62/562,966, filed on Sep. 25, 2017.

(51) Int. Cl.
*A61F 2/40* (2006.01)
*A61F 2/30* (2006.01)
*A61F 2/46* (2006.01)

(52) U.S. Cl.
CPC ........ *A61F 2/4003* (2013.01); *A61F 2/30942* (2013.01); *A61F 2/4059* (2013.01);
(Continued)

(58) Field of Classification Search
CPC ........ A61F 2/4003; A61F 2/40; A61F 2/4014; A61F 2/4612; A61F 2/30942;
(Continued)

(56) References Cited

U.S. PATENT DOCUMENTS

| 448,126 A | 3/1891 | Craig |
|---|---|---|
| 1,065,456 A | 6/1913 | Lowrey |

(Continued)

FOREIGN PATENT DOCUMENTS

| CA | 211530 | 5/2022 |
|---|---|---|
| DE | 4220217 | 12/1993 |

(Continued)

OTHER PUBLICATIONS

Non-Final Office Action issued in connection with U.S. Appl. No. 17/250,964, dated Jul. 26, 2021, 27 pages.
(Continued)

*Primary Examiner* — Yashita Sharma
(74) *Attorney, Agent, or Firm* — DUANE MORRIS LLP

(57) ABSTRACT

A stemless humeral anchor (10) includes a first end (12) configured to be embedded in a proximal portion of a humerus and a second end (14); a mating portion (16) for an articular component; a transversely extending collar (20); and a rotation control feature (22, 22A) for resisting rotation when the stemless humeral anchor is implanted. A void filling protrusion (24) can extend circumferentially from rotation control feature and can include a porous shell (26), in which a void filling component (28) can be disposed. The rotation control feature can comprise arms. One or more arms (22A) can have a larger radial extent than the others (22). A prosthesis assembly includes a base member (104) that has a helical structure (224) and one or more pathways (300). The pathway is accessible from a proximal end and is directed distally through the helical structure. The pathway
(Continued)

is located inward of an outer periphery of the helical structure. The pathway extends in a space between successive portions of the helical structure. The prosthesis assembly includes a locking device (108) that has a support member (132) and an arm (110) that projects away from the support member. The arm is disposed in the pathway when the support member is disposed adjacent to the proximal end of the base member. The arm is disposed through bone in the space between successive portions of the helical structure when the prosthesis assembly is implanted.

24 Claims, 53 Drawing Sheets

(52) U.S. Cl.
CPC .......... *A61F 2/4612* (2013.01); *A61F 2/4637* (2013.01); *A61F 2002/30011* (2013.01); *A61F 2002/30289* (2013.01); *A61F 2002/30408* (2013.01); *A61F 2002/30574* (2013.01); *A61F 2002/3093* (2013.01); *A61F 2002/4062* (2013.01)

(58) Field of Classification Search
CPC ............ A61F 2/4637; A61F 2002/4011; A61F 2002/4018; A61F 2002/4062; A61F 2002/4066; A61F 2002/30574; A61F 2002/30011; A61F 2002/30289; A61F 2002/20408; A61F 2002/3093; A61F 2/4059; A61F 2002/30408; A61F 2002/30405; A61F 2002/305; A61F 2002/4007; A61F 2002/4074; A61F 2250/0024; A61F 2/30767
See application file for complete search history.

(56) References Cited

U.S. PATENT DOCUMENTS

| | | |
|---|---|---|
| 1,123,730 A | 1/1915 | Greenfield |
| 2,444,099 A | 6/1948 | Hennessey, Jr. |
| 2,886,081 A | 5/1959 | Cowley |
| 3,523,395 A | 8/1970 | Rutter et al. |
| 3,609,056 A | 9/1971 | Hougen |
| 3,738,217 A | 6/1973 | Walker |
| 4,042,980 A | 8/1977 | Swanson et al. |
| 4,147,464 A | 4/1979 | Watson et al. |
| 4,250,600 A | 2/1981 | Gunther |
| 4,261,062 A | 4/1981 | Amstutz et al. |
| 4,406,023 A | 9/1983 | Harris |
| 4,550,450 A | 11/1985 | Kinnett |
| 4,601,289 A | 7/1986 | Chiarizzio et al. |
| 4,623,353 A | 11/1986 | Buechel et al. |
| 4,632,111 A | 12/1986 | Roche |
| 4,743,262 A | 5/1988 | Tronzo |
| D296,714 S | 7/1988 | Averill et al. |
| 4,865,605 A | 9/1989 | Dines et al. |
| 4,883,491 A | 11/1989 | Mallory et al. |
| 4,919,670 A | 4/1990 | Dale et al. |
| 4,964,865 A | 10/1990 | Burkhead et al. |
| 4,986,833 A | 1/1991 | Worland |
| 5,026,373 A | 6/1991 | Ray et al. |
| 5,032,132 A | 7/1991 | Matsen et al. |
| 5,044,393 A | 9/1991 | Jiles |
| 5,080,673 A | 1/1992 | Burkhead et al. |
| 5,112,338 A | 5/1992 | Anspach, III |
| 5,163,964 A | 11/1992 | Lazzeri et al. |
| 5,171,277 A | 12/1992 | Roger |
| 5,257,995 A | 11/1993 | Umber et al. |
| 5,282,865 A | 2/1994 | Dong |
| 5,358,526 A | 10/1994 | Tornier |
| 5,443,471 A | 8/1995 | Swajger |
| 5,489,309 A | 2/1996 | Lackey et al. |
| 5,489,310 A | 2/1996 | Mikhail |
| 5,507,817 A | 4/1996 | Craig et al. |
| 5,514,136 A | 5/1996 | Richelsoph |
| 5,534,006 A | 7/1996 | Szabo et al. |
| 5,540,697 A | 7/1996 | Rehmann et al. |
| 5,681,134 A | 10/1997 | Ebert |
| 5,702,486 A | 12/1997 | Craig et al. |
| 5,720,750 A | 2/1998 | Koller et al. |
| 5,723,018 A | 3/1998 | Cyprien et al. |
| 5,776,194 A | 7/1998 | Mikol et al. |
| 5,800,551 A | 9/1998 | Williamson et al. |
| 5,810,524 A | 9/1998 | Wirth, Jr. et al. |
| 5,820,315 A | 10/1998 | Collard |
| 5,830,215 A | 11/1998 | Incavo et al. |
| 5,849,015 A | 12/1998 | Haywood et al. |
| 5,954,727 A | 9/1999 | Collazo |
| 5,976,148 A | 11/1999 | Charpenet et al. |
| 6,045,582 A | 4/2000 | Prybyla |
| 6,063,124 A | 5/2000 | Amstutz |
| 6,099,214 A | 8/2000 | Lee et al. |
| 6,110,179 A | 8/2000 | Flivik et al. |
| 6,113,605 A | 9/2000 | Storer |
| 6,132,469 A | 10/2000 | Schroeder |
| 6,139,551 A | 10/2000 | Michelson et al. |
| 6,146,423 A | 11/2000 | Cohen et al. |
| 6,174,335 B1 | 1/2001 | Varieur et al. |
| 6,187,012 B1 | 2/2001 | Masini |
| 6,197,063 B1 | 3/2001 | Dews |
| 6,264,299 B1 | 7/2001 | Noda |
| 6,264,657 B1 | 7/2001 | Urbahns et al. |
| 6,306,171 B1 | 10/2001 | Conzemius |
| 6,322,564 B1 | 11/2001 | Surma |
| 6,364,910 B1 | 4/2002 | Shultz et al. |
| 6,368,271 B1 | 4/2002 | Sharratt |
| 6,368,353 B1 | 4/2002 | Arcand |
| 6,379,917 B1 | 4/2002 | Okun et al. |
| 6,409,730 B1 | 6/2002 | Green et al. |
| 6,508,840 B1 | 1/2003 | Rockwood, Jr. et al. |
| 6,520,994 B2 | 2/2003 | Nogarin |
| 6,537,278 B1 | 3/2003 | Johnson |
| 6,626,913 B1 | 9/2003 | McKinnon et al. |
| 6,666,874 B2 | 12/2003 | Heitzmann et al. |
| 6,719,799 B1 | 4/2004 | Kropf |
| 6,736,851 B2 | 5/2004 | Maroney et al. |
| 6,746,452 B2 | 6/2004 | Tuke et al. |
| 6,783,549 B1 | 8/2004 | Stone et al. |
| 6,786,684 B1 | 9/2004 | Ecker |
| 6,797,006 B2 | 9/2004 | Hodorek et al. |
| 7,044,973 B2 | 5/2006 | Rockwood, Jr. et al. |
| 7,097,663 B1 | 8/2006 | Nicol et al. |
| 7,140,087 B1 | 11/2006 | Giltner |
| 7,160,328 B2 | 1/2007 | Rockwood, Jr. et al. |
| 7,169,184 B2 | 1/2007 | Dalla Pria |
| 7,175,663 B1 | 2/2007 | Stone |
| 7,179,084 B1 | 2/2007 | Kometas |
| 7,189,036 B1 | 3/2007 | Watson |
| 7,189,261 B2 | 3/2007 | Dews et al. |
| 7,204,854 B2 | 4/2007 | Guederian et al. |
| 7,208,222 B2 * | 4/2007 | Rolfe ..................... A61F 2/442 |
| | | 428/137 |
| 7,344,565 B2 | 3/2008 | Seyer et al. |
| 7,465,319 B2 | 12/2008 | Tornier |
| 7,476,228 B2 | 1/2009 | Abou |
| 7,476,253 B1 | 1/2009 | Craig et al. |
| 7,585,327 B2 | 9/2009 | Winslow |
| 7,615,080 B2 | 11/2009 | Ondrla |
| 7,637,703 B2 | 12/2009 | Khangar et al. |
| 7,648,530 B2 | 1/2010 | Habermeyer et al. |
| 7,670,382 B2 | 3/2010 | Parrott et al. |
| 7,678,150 B2 | 3/2010 | Tornier et al. |
| 7,744,602 B2 | 6/2010 | Teeny et al. |
| 7,758,650 B2 | 7/2010 | Dews et al. |
| 7,887,544 B2 | 2/2011 | Tornier et al. |
| 7,927,376 B2 | 4/2011 | Leisinger et al. |
| D643,926 S | 8/2011 | Collins |
| 8,021,370 B2 | 9/2011 | Fenton et al. |
| 8,114,089 B2 | 2/2012 | Divoux et al. |
| 8,162,947 B2 | 4/2012 | Dreyfuss |

(56) References Cited

U.S. PATENT DOCUMENTS

| | | |
|---|---|---|
| 8,182,541 B2 | 5/2012 | Long et al. |
| 8,187,282 B2 | 5/2012 | Tornier et al. |
| 8,192,497 B2 | 6/2012 | Ondrla |
| 8,202,275 B2 | 6/2012 | Wozencroft |
| 8,221,037 B2 | 7/2012 | Neitzell |
| 8,231,682 B2 | 7/2012 | LaFosse |
| 8,246,687 B2 | 8/2012 | Katrana et al. |
| 8,262,667 B1 | 9/2012 | Silver et al. |
| D668,331 S | 10/2012 | Ren et al. |
| 8,277,512 B2 | 10/2012 | Parrott et al. |
| 8,317,871 B2 | 11/2012 | Stone et al. |
| 8,409,798 B2 | 4/2013 | Luy et al. |
| 8,419,798 B2 | 4/2013 | Ondrla et al. |
| D685,474 S | 7/2013 | Courtney |
| 8,500,744 B2 | 8/2013 | Wozencroft et al. |
| 8,506,638 B2 | 8/2013 | Vanasse et al. |
| 8,512,410 B2 | 8/2013 | Metcalfe et al. |
| D691,710 S | 10/2013 | White |
| 8,591,592 B2 | 11/2013 | Dreyfuss |
| 8,608,749 B2 | 12/2013 | Meridew et al. |
| 8,641,773 B2 | 2/2014 | Bergin et al. |
| 8,647,387 B2 | 2/2014 | Winslow |
| 8,663,333 B2 | 3/2014 | Metcalfe et al. |
| 8,663,334 B2 | 3/2014 | Viscardi et al. |
| 8,690,958 B2 | 4/2014 | Klawitter et al. |
| 8,702,800 B2 | 4/2014 | Linares et al. |
| 8,753,402 B2 | 6/2014 | Winslow et al. |
| 8,795,379 B2 | 8/2014 | Smith et al. |
| 8,840,671 B2 | 9/2014 | Ambacher |
| 8,845,742 B2 | 9/2014 | Kusogullari et al. |
| 8,864,834 B2 | 10/2014 | Boileau et al. |
| 8,870,962 B2 | 10/2014 | Roche et al. |
| 8,876,908 B2 | 11/2014 | Katrana et al. |
| 8,882,845 B2 | 11/2014 | Wirth et al. |
| 8,992,623 B2 | 3/2015 | Hopkins et al. |
| D745,678 S | 12/2015 | Courtney et al. |
| 9,233,003 B2 | 1/2016 | Roche et al. |
| 9,289,218 B2 | 3/2016 | Courtney, Jr. et al. |
| 9,326,862 B2 | 5/2016 | Smith et al. |
| 9,326,865 B2 | 5/2016 | Katrana et al. |
| 9,364,334 B2 | 6/2016 | Katrana et al. |
| 9,498,344 B2 | 11/2016 | Hodorek et al. |
| 9,498,345 B2 | 11/2016 | Burkhead et al. |
| 9,510,839 B2 | 12/2016 | Maroney et al. |
| 9,603,712 B2 | 3/2017 | Bachmaier |
| 9,610,165 B2 | 4/2017 | Poncet et al. |
| 9,615,928 B2 | 4/2017 | Visser et al. |
| 9,820,859 B2 | 11/2017 | Gervasi et al. |
| 9,956,083 B2 | 5/2018 | Humphrey |
| D831,218 S | 10/2018 | da Costa |
| 10,166,032 B2 | 1/2019 | Stone et al. |
| D840,539 S | 2/2019 | Courtney et al. |
| 10,335,285 B2 | 7/2019 | Viscardi et al. |
| 10,368,999 B2 | 8/2019 | Greiwe |
| 10,433,969 B2 | 10/2019 | Humphrey |
| 10,456,264 B2 | 10/2019 | Hodorek et al. |
| 10,463,499 B2 | 11/2019 | Emerick et al. |
| 10,537,390 B2 | 1/2020 | Varadarajan et al. |
| D875,936 S | 2/2020 | Martin |
| 10,548,737 B2 | 2/2020 | Hodorek et al. |
| 10,828,169 B2 * | 11/2020 | Britton ............... A61F 2/4014 |
| 10,898,348 B2 | 1/2021 | Vivanz et al. |
| 10,945,862 B2 | 3/2021 | Roby et al. |
| 11,076,962 B2 | 8/2021 | Kemp et al. |
| D938,034 S | 12/2021 | Knox et al. |
| 11,229,524 B2 * | 1/2022 | Sperling ............... A61F 2/4003 |
| D951,449 S | 5/2022 | Knox et al. |
| D952,143 S | 5/2022 | Conklin |
| 11,364,127 B2 | 6/2022 | Deransart et al. |
| 2001/0047210 A1 | 11/2001 | Wolf |
| 2001/0049561 A1 | 12/2001 | Dews et al. |
| 2002/0116007 A1 | 8/2002 | Lewis |
| 2002/0156534 A1 | 10/2002 | Grusin et al. |
| 2003/0028253 A1 | 2/2003 | Stone et al. |
| 2003/0031521 A1 | 2/2003 | Haughton et al. |
| 2003/0074080 A1 | 4/2003 | Murray |
| 2003/0114933 A1 | 6/2003 | Bouttens et al. |
| 2003/0125810 A1 | 7/2003 | Sullivan et al. |
| 2004/0010262 A1 | 1/2004 | Parkinson et al. |
| 2004/0049270 A1 | 3/2004 | Gewirtz |
| 2004/0186586 A1 | 9/2004 | Seyer et al. |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0199258 A1 | 10/2004 | Macara |
| 2004/0220674 A1 | 11/2004 | Pria |
| 2004/0243136 A1 | 12/2004 | Gupta et al. |
| 2004/0254646 A1 | 12/2004 | Stone et al. |
| 2005/0098915 A1 | 5/2005 | Long et al. |
| 2005/0107882 A1 | 5/2005 | Stone et al. |
| 2005/0112397 A1 | 5/2005 | Rolfe et al. |
| 2005/0203539 A1 | 9/2005 | Grimm et al. |
| 2005/0209597 A1 | 9/2005 | Long et al. |
| 2005/0261775 A1 | 11/2005 | Baum et al. |
| 2005/0267478 A1 | 12/2005 | Corradi et al. |
| 2006/0004378 A1 | 1/2006 | Raines |
| 2006/0009852 A1 | 1/2006 | Winslow et al. |
| 2006/0020344 A1 | 1/2006 | Shultz et al. |
| 2006/0064173 A1 | 3/2006 | Guederian |
| 2006/0089656 A1 | 4/2006 | Allard et al. |
| 2006/0142866 A1 | 6/2006 | Baratz et al. |
| 2006/0161167 A1 | 7/2006 | Myers et al. |
| 2006/0195105 A1 | 8/2006 | Teeny et al. |
| 2006/0200165 A1 | 9/2006 | Tulkis |
| 2006/0200249 A1 | 9/2006 | Beguin et al. |
| 2007/0010825 A1 | 1/2007 | Leisinger et al. |
| 2007/0100458 A1 | 5/2007 | Dalla Pria |
| 2007/0123890 A1 | 5/2007 | Way et al. |
| 2007/0123893 A1 | 5/2007 | O'Donoghue |
| 2007/0123909 A1 | 5/2007 | Rupp et al. |
| 2007/0156246 A1 | 7/2007 | Meswania et al. |
| 2007/0162038 A1 | 7/2007 | Tuke |
| 2007/0162141 A1 | 7/2007 | Dews et al. |
| 2007/0173945 A1 | 7/2007 | Wiley et al. |
| 2007/0198094 A1 | 8/2007 | Berelsman et al. |
| 2007/0212179 A1 | 9/2007 | Khangar et al. |
| 2007/0219562 A1 | 9/2007 | Slone et al. |
| 2007/0225817 A1 | 9/2007 | Reubelt et al. |
| 2007/0233132 A1 | 10/2007 | Valla |
| 2007/0288096 A1 | 12/2007 | Surma |
| 2008/0021564 A1 | 1/2008 | Gunther |
| 2008/0077146 A1 | 3/2008 | Pernsteiner et al. |
| 2008/0010900 A1 | 5/2008 | Maroney et al. |
| 2008/0109000 A1 | 5/2008 | Maroney et al. |
| 2008/0172061 A1 | 7/2008 | Ragbir |
| 2008/0195111 A1 | 8/2008 | Anderson |
| 2008/0221576 A1 | 9/2008 | Keller |
| 2008/0249577 A1 | 10/2008 | Dreyfuss |
| 2009/0099662 A1 | 4/2009 | Splieth et al. |
| 2009/0171462 A1 | 7/2009 | Poncet et al. |
| 2009/0281630 A1 | 11/2009 | Delince et al. |
| 2009/0306782 A1 | 12/2009 | Schwyzer |
| 2010/0042214 A1 | 2/2010 | Nebosky et al. |
| 2010/0082035 A1 | 4/2010 | Keefer |
| 2010/0087927 A1 | 4/2010 | Roche et al. |
| 2010/0114326 A1 * | 5/2010 | Winslow ............... A61F 2/3601 |
| | | 623/23.42 |
| 2010/0121331 A1 | 5/2010 | Sharp et al. |
| 2010/0191340 A1 | 7/2010 | Dreyfuss |
| 2010/0268238 A1 | 10/2010 | Sikora et al. |
| 2010/0274360 A1 | 10/2010 | Gunther |
| 2010/0278601 A1 | 11/2010 | Beynon |
| 2010/0331902 A1 | 12/2010 | Biegun |
| 2011/0035013 A1 | 2/2011 | Winslow et al. |
| 2011/0082587 A1 | 4/2011 | Ziaei et al. |
| 2011/0118846 A1 | 5/2011 | Katrana et al. |
| 2011/0137424 A1 | 6/2011 | Lappin et al. |
| 2011/0153023 A1 | 6/2011 | Deffenbaugh et al. |
| 2011/0224673 A1 | 9/2011 | Smith |
| 2011/0276144 A1 | 11/2011 | Wirth et al. |
| 2011/0313533 A1 | 12/2011 | Gunther |
| 2012/0022664 A1 | 1/2012 | Vandermeulen et al. |
| 2012/0083769 A1 | 4/2012 | Burgi et al. |
| 2012/0109321 A1 | 5/2012 | Stone et al. |

(56) References Cited

U.S. PATENT DOCUMENTS

| | | |
|---|---|---|
| 2012/0184964 A1 | 7/2012 | Hudak, Jr. |
| 2012/0221111 A1 | 8/2012 | Burkhead, Jr. et al. |
| 2012/0232562 A1 | 9/2012 | Mani et al. |
| 2012/0253467 A1 | 10/2012 | Frankle |
| 2012/0265315 A1 | 10/2012 | Kusogullari et al. |
| 2012/0265319 A1 | 10/2012 | Prybyla et al. |
| 2012/0277880 A1 | 11/2012 | Winslow et al. |
| 2012/0290099 A1 | 11/2012 | Gibson et al. |
| 2012/0296339 A1 | 11/2012 | Iannotti et al. |
| 2012/0296435 A1 | 11/2012 | Ambacher |
| 2013/0018382 A1 | 1/2013 | Jones et al. |
| 2013/0018476 A1* | 1/2013 | Katrana ............. A61F 2/4612 623/19.14 |
| 2013/0123929 A1 | 5/2013 | McDaniel et al. |
| 2013/0123930 A1 | 5/2013 | Burt |
| 2013/0150972 A1 | 6/2013 | Iannotti et al. |
| 2013/0173006 A1 | 7/2013 | Duport |
| 2013/0178943 A1 | 7/2013 | Duport |
| 2013/0190882 A1 | 7/2013 | Humphrey |
| 2013/0204375 A1 | 8/2013 | Winslow et al. |
| 2013/0211539 A1 | 8/2013 | McDaniel et al. |
| 2013/0261626 A1 | 10/2013 | Chavarria et al. |
| 2013/0261629 A1 | 10/2013 | Anthony et al. |
| 2013/0261630 A1 | 10/2013 | Courtney, Jr. et al. |
| 2013/0261754 A1 | 10/2013 | Anthony et al. |
| 2013/0261755 A1 | 10/2013 | Anthony et al. |
| 2013/0282129 A1 | 10/2013 | Phipps |
| 2013/0325134 A1 | 12/2013 | Viscardi et al. |
| 2013/0331849 A1 | 12/2013 | Splieth et al. |
| 2014/0012272 A1 | 1/2014 | Leisinger |
| 2014/0012380 A1 | 1/2014 | Laurence et al. |
| 2014/0058523 A1 | 2/2014 | Walch et al. |
| 2014/0074246 A1 | 3/2014 | Huebner et al. |
| 2014/0107792 A1 | 4/2014 | Hopkins et al. |
| 2014/0156012 A1 | 6/2014 | Winslow |
| 2014/0236304 A1 | 8/2014 | Hodorek et al. |
| 2014/0257304 A1 | 9/2014 | Eash |
| 2014/0257499 A1 | 9/2014 | Winslow et al. |
| 2014/0288657 A1 | 9/2014 | Lederman et al. |
| 2014/0296988 A1 | 10/2014 | Winslow et al. |
| 2014/0358239 A1 | 12/2014 | Katrana et al. |
| 2014/0358240 A1 | 12/2014 | Katrana et al. |
| 2014/0379089 A1 | 12/2014 | Bachmaier |
| 2015/0134066 A1 | 5/2015 | Bachmaier |
| 2015/0190151 A1 | 7/2015 | Budhabbatti et al. |
| 2015/0250601 A1 | 9/2015 | Humphrey |
| 2015/0265411 A1 | 9/2015 | Deransart et al. |
| 2015/0289984 A1 | 10/2015 | Budge |
| 2015/0297354 A1 | 10/2015 | Walch et al. |
| 2015/0328015 A1 | 11/2015 | Olson et al. |
| 2016/0030196 A1 | 2/2016 | Eraly et al. |
| 2016/0051367 A1 | 2/2016 | Gervasi et al. |
| 2016/0059403 A1 | 3/2016 | Mugnier |
| 2016/0157911 A1 | 6/2016 | Courtney, Jr. et al. |
| 2016/0206445 A1 | 7/2016 | Gheevarughese et al. |
| 2016/0324648 A1 | 11/2016 | Hodorek et al. |
| 2016/0331551 A1 | 11/2016 | Slade et al. |
| 2016/0374815 A1 | 12/2016 | Siccardi et al. |
| 2017/0007330 A1 | 1/2017 | Britton et al. |
| 2017/0027702 A1 | 2/2017 | Goldstein et al. |
| 2017/0056187 A1 | 3/2017 | Humphrey et al. |
| 2017/0071748 A1 | 3/2017 | Humphrey |
| 2017/0105843 A1 | 4/2017 | Britton et al. |
| 2017/0112634 A1 | 4/2017 | Gunn et al. |
| 2017/0150978 A1 | 6/2017 | Iannotti et al. |
| 2017/0273800 A1 | 9/2017 | Emerick et al. |
| 2017/0304063 A1 | 10/2017 | Hatzidakis et al. |
| 2017/0340449 A1 | 11/2017 | Deransart et al. |
| 2017/0367714 A1 | 12/2017 | McCulloch et al. |
| 2017/0367836 A1 | 12/2017 | Cardon et al. |
| 2018/0028249 A1 | 2/2018 | Jaumard |
| 2018/0036019 A1 | 2/2018 | Iannotti et al. |
| 2018/0092757 A1 | 4/2018 | Behzadi et al. |
| 2018/0092760 A1 | 4/2018 | Sperling et al. |
| 2018/0103967 A1 | 4/2018 | Rouyer et al. |
| 2018/0161176 A1 | 6/2018 | Vivanz et al. |
| 2018/0193168 A1 | 7/2018 | Termanini et al. |
| 2018/0200067 A1 | 7/2018 | Axelson et al. |
| 2018/0206859 A1 | 7/2018 | Pendleton et al. |
| 2018/0271667 A1 | 9/2018 | Kemp et al. |
| 2018/0280152 A1 | 10/2018 | Mutchler et al. |
| 2019/0105165 A1 | 4/2019 | Sikora et al. |
| 2019/0105169 A1 | 4/2019 | Sperling |
| 2019/0159906 A1 | 5/2019 | Knox et al. |
| 2019/0175354 A1 | 6/2019 | Knox et al. |
| 2019/0216518 A1 | 7/2019 | Courtney, Jr. et al. |
| 2019/0231558 A1 | 8/2019 | Beck et al. |
| 2019/0328536 A1 | 10/2019 | Martin et al. |
| 2019/0336307 A1 | 11/2019 | Sungu et al. |
| 2019/0374349 A1 | 12/2019 | Müller |
| 2020/0000573 A1 | 1/2020 | Whittaker et al. |
| 2020/0008947 A1 | 1/2020 | Emerick et al. |
| 2020/0121474 A1 | 4/2020 | Pendleton et al. |
| 2020/0188125 A1 | 6/2020 | Hodorek et al. |
| 2020/0214845 A1 | 7/2020 | Knox et al. |
| 2020/0214853 A1 | 7/2020 | Sweitzer |
| 2020/0222205 A1 | 7/2020 | Gosik-Wolfe et al. |
| 2020/0289276 A1 | 9/2020 | Lefebvre et al. |
| 2021/0030565 A1 | 2/2021 | Dun et al. |
| 2021/0045895 A1 | 2/2021 | Sapio et al. |
| 2021/0212840 A1 | 7/2021 | Sweitzer et al. |
| 2021/0212841 A1 | 7/2021 | Sweitzer et al. |
| 2021/0228362 A1 | 7/2021 | Whitwell et al. |
| 2021/0228370 A1 | 7/2021 | Ek et al. |
| 2021/0228371 A1 | 7/2021 | Deransart et al. |
| 2021/0228372 A1 | 7/2021 | Knox et al. |
| 2021/0244487 A1 | 8/2021 | Beck |
| 2021/0251643 A1 | 8/2021 | Stump |
| 2021/0290411 A1 | 9/2021 | Gosik-Wolfe |
| 2021/0315713 A1 | 10/2021 | Keach et al. |
| 2021/0330476 A1 | 10/2021 | Alden |
| 2021/0338456 A1 | 11/2021 | Wolfe et al. |
| 2021/0386558 A1 | 12/2021 | Alden |
| 2021/0393414 A1 | 12/2021 | Robicheaux et al. |
| 2022/0023053 A1 | 1/2022 | Kim et al. |
| 2022/0023071 A1 | 1/2022 | Sweitzer |
| 2022/0104835 A1 | 4/2022 | Blaser et al. |
| 2022/0117756 A1 | 4/2022 | Blaser et al. |
| 2022/0125591 A1 | 4/2022 | Rivera, Jr. |
| 2022/0151794 A1 | 5/2022 | Fattori et al. |
| 2022/0287850 A1 | 9/2022 | Daudet |
| 2022/0354658 A1 | 11/2022 | Knox et al. |

FOREIGN PATENT DOCUMENTS

| | | |
|---|---|---|
| DE | 10233204 | 1/2004 |
| DE | 102004042502 | 3/2006 |
| EP | 0 274 094 | 8/1990 |
| EP | 1 413 265 | 4/2004 |
| EP | 0 959 822 | 5/2004 |
| EP | 1 125 565 | 12/2004 |
| EP | 1 518 519 | 3/2005 |
| EP | 1 004 283 | 5/2005 |
| EP | 1 639 967 | 3/2006 |
| EP | 1 762 191 | 3/2007 |
| EP | 1 952 788 | 8/2008 |
| EP | 1 867 303 | 9/2010 |
| EP | 1 977 720 | 1/2011 |
| EP | 1 550 420 | 2/2012 |
| EP | 2 261 303 | 11/2012 |
| EP | 1 706 074 | 12/2012 |
| EP | 2 564 814 | 3/2013 |
| EP | 2 567 676 | 3/2013 |
| EP | 2 574 313 | 4/2013 |
| EP | 2586387 A1 | 5/2013 |
| EP | 2 616 013 | 7/2013 |
| EP | 2 474 288 | 9/2013 |
| EP | 2 663 263 | 5/2014 |
| EP | 2 502 605 | 8/2014 |
| EP | 2 800 541 | 11/2014 |
| EP | 2 815 726 | 8/2015 |
| EP | 2 353 549 | 6/2016 |
| EP | 3 117 801 | 1/2017 |
| EP | 2 965 720 B1 | 7/2017 |

(56) References Cited

FOREIGN PATENT DOCUMENTS

| | | |
|---|---|---|
| FR | 2 674 122 | 9/1992 |
| FR | 2980685 B1 | 10/2013 |
| FR | 2997290 B1 | 11/2015 |
| GB | 2405346 | 3/2005 |
| JP | 2002506361 A | 2/2002 |
| JP | 2005511243 A | 4/2005 |
| JP | 2009523578 A | 6/2009 |
| JP | 3179628 U | 11/2012 |
| JP | 2015532863 A | 11/2015 |
| JP | 2016528956 A | 9/2016 |
| JP | 2019506281 A | 3/2019 |
| WO | WO 01/67988 | 9/2001 |
| WO | WO 02/17822 | 3/2002 |
| WO | 2006106419 A2 | 10/2006 |
| WO | WO 2008/011078 | 1/2008 |
| WO | WO 2008/146124 | 12/2008 |
| WO | WO 2011/081797 | 7/2011 |
| WO | WO 2012/035263 | 3/2012 |
| WO | WO 2012/130524 | 10/2012 |
| WO | WO 2013/009407 | 1/2013 |
| WO | WO 2013/064569 | 5/2013 |
| WO | WO 2013/148229 | 10/2013 |
| WO | WO 2014/005644 | 1/2014 |
| WO | WO 2014/058314 | 4/2014 |
| WO | WO 2015/112307 | 7/2015 |
| WO | 2016094739 A1 | 6/2016 |
| WO | WO 2016/094739 | 6/2016 |
| WO | WO 2017/165090 | 9/2017 |
| WO | WO 2017/184792 | 10/2017 |
| WO | WO 2018/022227 | 2/2018 |
| WO | WO 2019/060780 | 3/2019 |
| WO | WO 2019/106278 | 6/2019 |
| WO | 2019133905 A1 | 7/2019 |

OTHER PUBLICATIONS

Final Rejection issued in connection with U.S. Appl. No. 16/249,720, dated Aug. 20, 2021, 40 pages.
Final Rejection issued in connection with U.S. Appl. No. 16/580,367, dated Aug. 24, 2021, 9 pages.
Non-Final Office Action issued in connection with U.S. Appl. No. 16/519,937, dated Aug. 17, 2021, 21 pages.
Barth, et al., "Is global humeral head offset related to intramedullary canal width? A computer tomography morphometric study," Journal of Experimental Orthopaedics, 2018, vol. 5, pp. 1-8.
Boileau, et al., "The Three-Dimensional Geometry of the Proximal Humerus: Implications for Surgical Technique and Prosthetic Design," J Bone Joint Surg, Sep. 1997, vol. 79-B, Issue 5, pp. 857-865.
Routman, et al., "Reverse Shoulder Arthroplasty Prosthesis Design Classification System," Bulletin of the Hospital for Joint Diseases, 2015, vol. 73 (Suppl 1), pp. S5-S14.
International Search Report and Written Opinion for PCT/US2018/052294 dated Apr. 4, 2019 in 13 pages.
Final Rejection issued in connection with U.S. Appl. No. 17/250,964, dated Sep. 9, 2021, 22 pages.
Non-Final Office Action issued in connection with U.S. Appl. No. 17/250,964, dated Feb. 24, 2022, 12 pages.
First Office Action issued in connection with Japanese Patent Application No. 2019-555151, dated Feb. 21, 2022, 5 pages.
First Examination Report issued in connection with Australian Patent Application No. 2021250994, dated Jun. 2, 2022, 5 pages.
Office Action issued in connection with Japanese Patent Application No. 2021-518159, dated May 24, 2022, 5 pages.
Third Examination Report issued in connection with Australian Patent Application No. 2019355854, dated May 10, 2022, 4 pages.
Non-Final Office Action issued in connection with U.S. Appl. No. 17/717,253, dated Jun. 29, 2022, 56 pages.
First Examination Report issued in connection with Australian Patent Application No. 2020360410, dated Nov. 24, 2022, 5 pages.
First Office Action issued in connection with Japanese Patent Application No. 2022-520122, dated Apr. 18, 2023, 4 pages.
Med Gadget, "Tornier Announces First Implant in U.S. Trial of Its Simpliciti Stemless Shoulder Joint Replacement System", first available Aug. 5, 2011. (https:/Avwww.medgadget.com/2011/08/tornier-announces-first-implant-in-u-s-trial-of-its-simpliciti-stemless-shoulder-joint-replacement-system.html) (Year: 2011).
Wright Media, "Tornier Aequalis Reversed FX", first available May 19, 2016. (https:/Avww.wrightemedia.com/ProductFiles/Files/PDFs/ CAW-1146_EN_LR_LE.pdf) (Year: 2016).
Wright Media, "Aequalis Ascend Flex", first available Jul. 30, 2019. (https:/Avww.wrightemedia.com/ProductFiles/Files/PDFs/AP-010187_EN_LR_LE.pdf) (Year: 2019).
Arthrex, "Univers Revers Shoulder System", first available Apr. 24, 2019. (https:/Avww.arthrex.com/resources/surgical-technique-guide/ qkv6M00_50qt2QFBx1PKnA/univers-revers-shoulder-system) (Year: 2019).
First Office Action issued in corresponding Japanese Patent Application No. 2021-506973, dated Jun. 5, 2023, 5 pages.
Communication Pursuant to Article 94(3) issued in connection with European Patent Application No. 18746503.4, dated Oct. 17, 2023, 5 pages.
Non-Final Office Action issued in connection with U.S. Appl. No. 17/650,722, dated Nov. 15, 2023, 10 pages.
Notice of Allowance issued in connection with U.S. Appl. No. 17/645,607, dated Dec. 20, 2023, 11 pages.
Non-Final Office Action issued in connection with U.S. Appl. No. 17/359,745, dated Nov. 26, 2023, 7 pages.
Final Office Action issued in connection with U.S. Appl. No. 16/910,663, dated Nov. 16, 2023, 9 pages.
Final Office Action issued in connection with Japanese Patent Application No. 2022-520122, dated Sep. 26, 2023, 3 pages.
Non-Final Office Action issued in connection with U.S. Appl. No. 17/281,683, dated Oct. 6, 2023, 7 pages.
Communication Pursuant to Article 94(3) issued in connection with European Patent Application No. 19759204.1, dated May 9, 2023, 6 pages.
Non-Final Office Action issued in connection with U.S. Appl. No. 16/910,663, dated Dec. 15, 2022, 9 pages.
Non-Final Office Action issued in connection with U.S. Appl. No. 17/451,499, Feb. 9, 2024, 7 pages.

\* cited by examiner

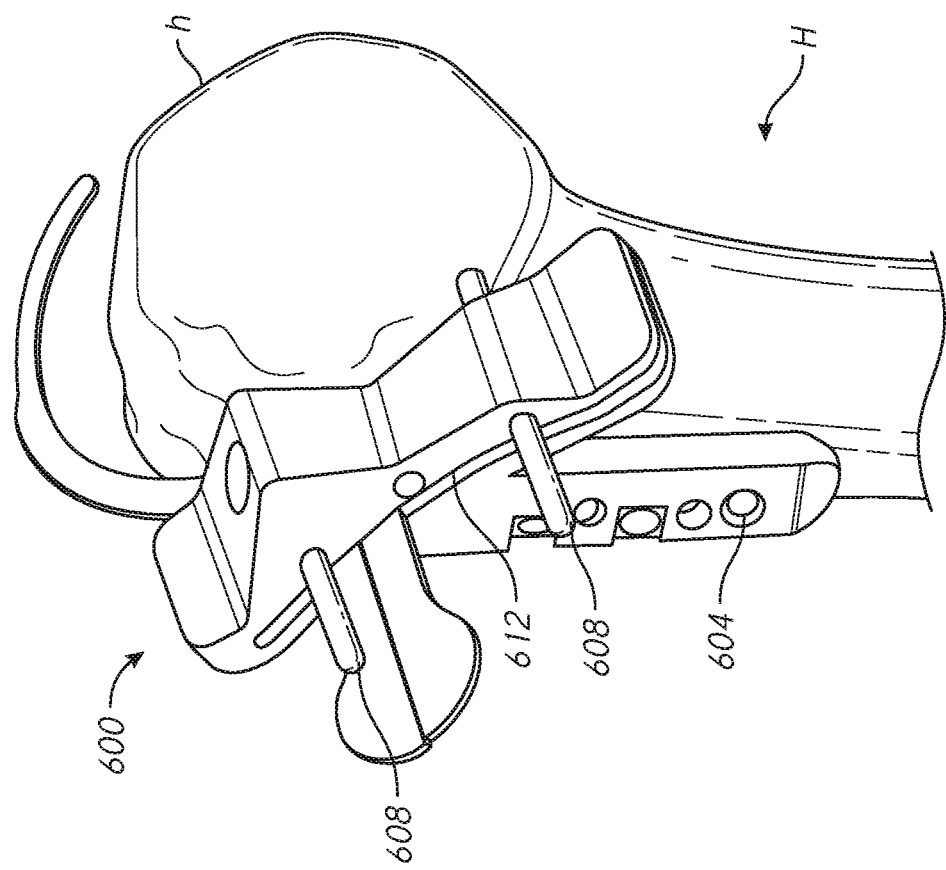

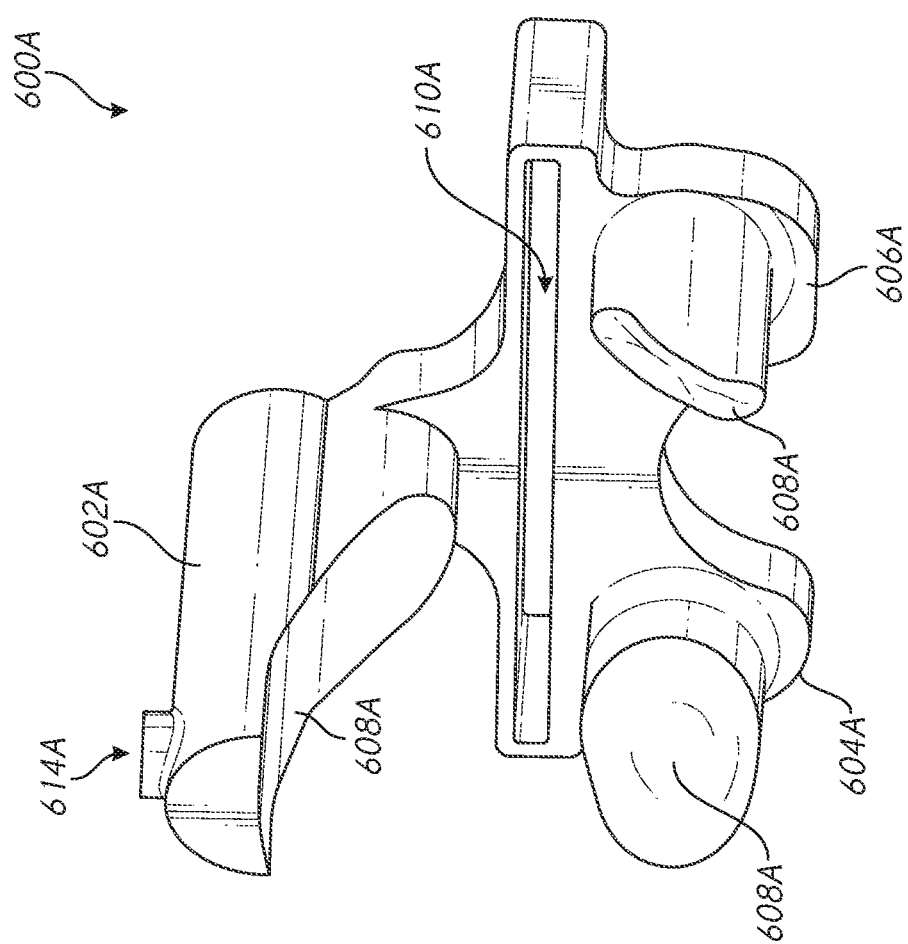

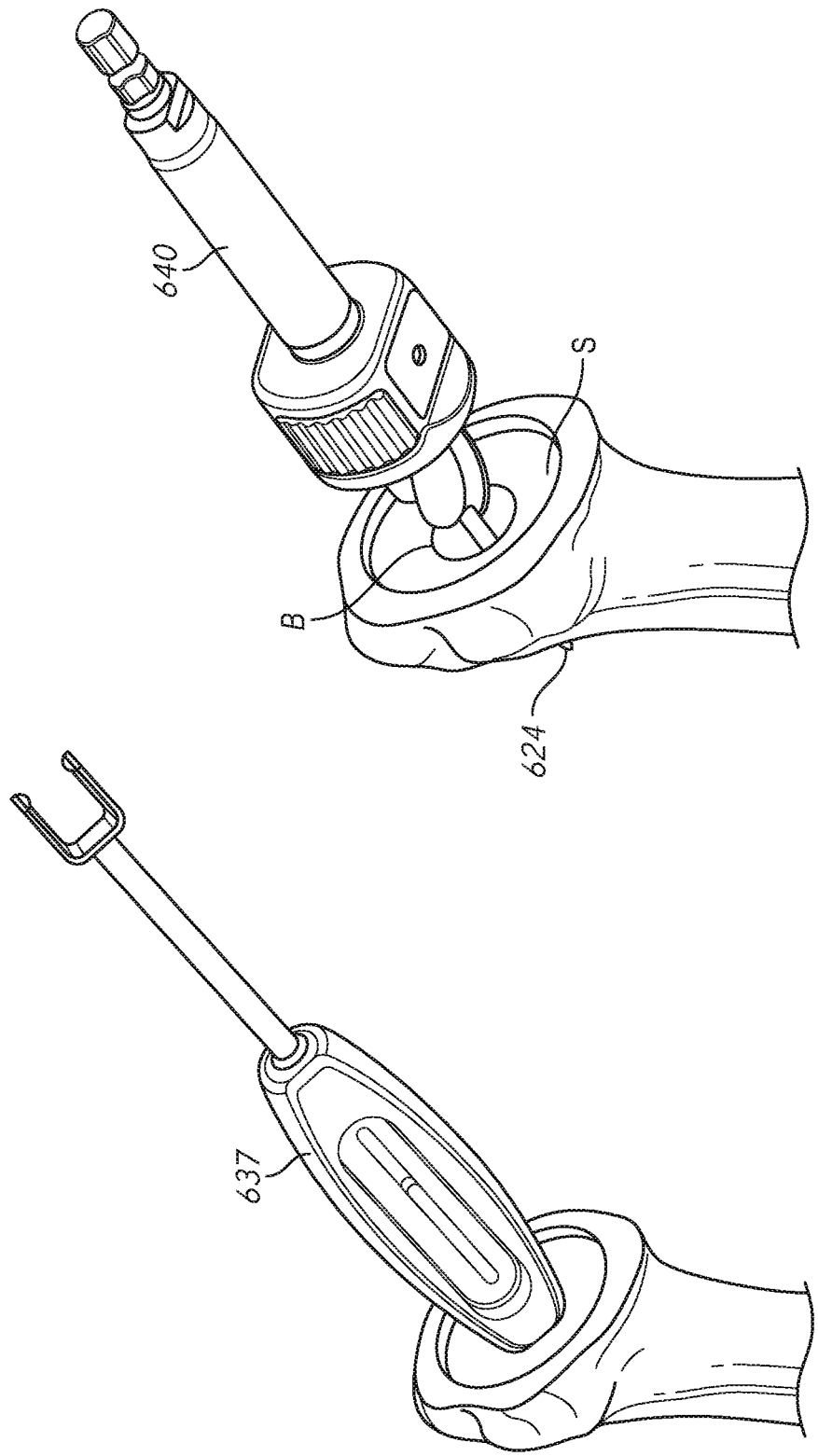

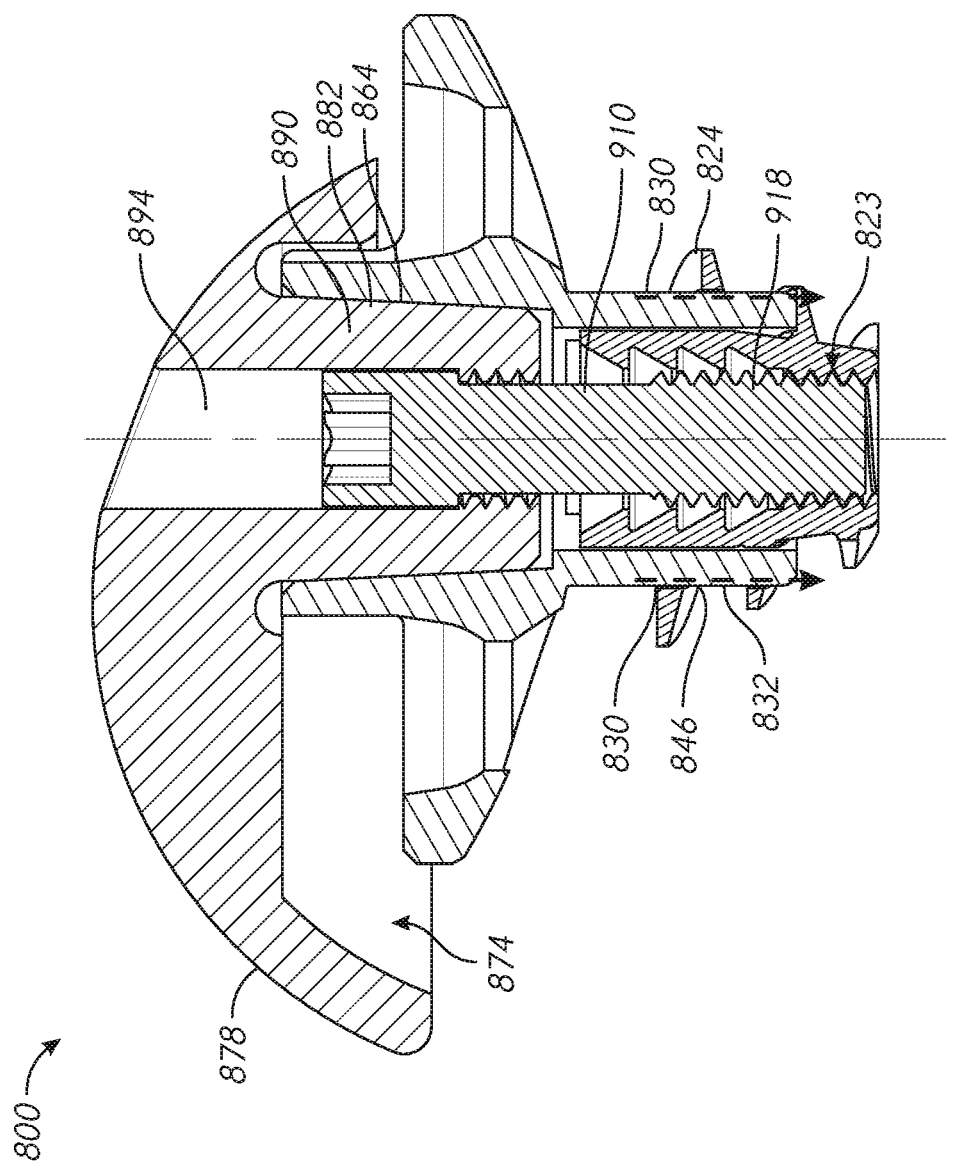

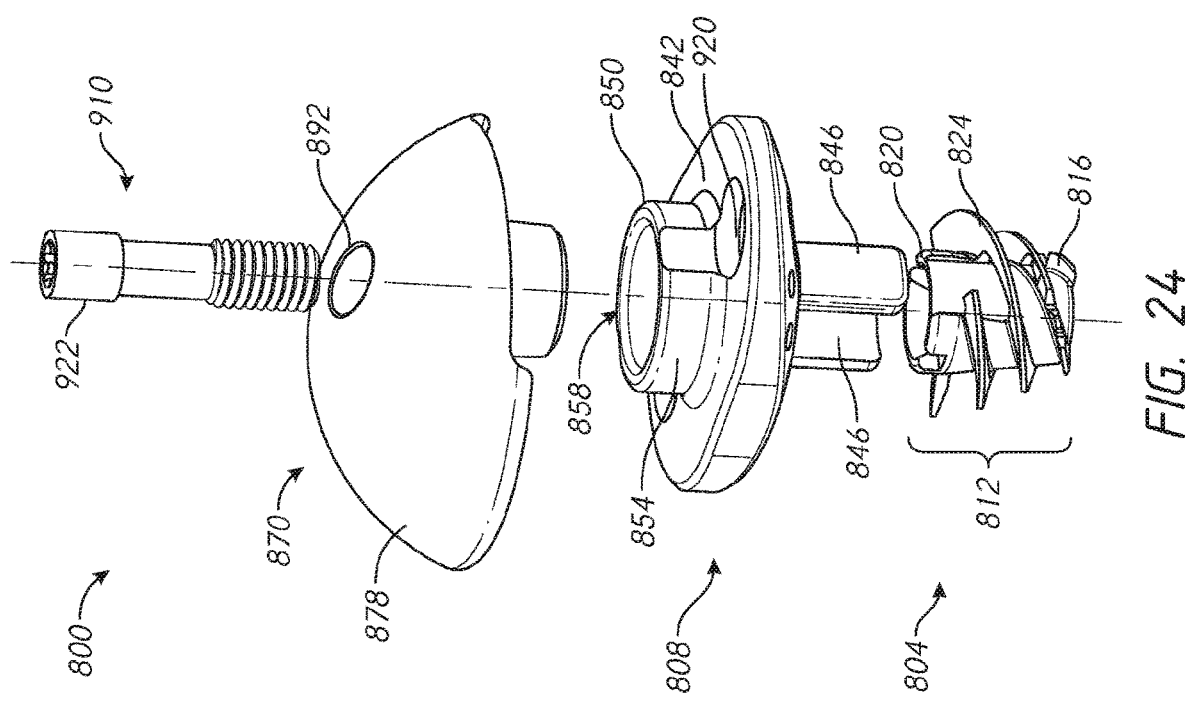

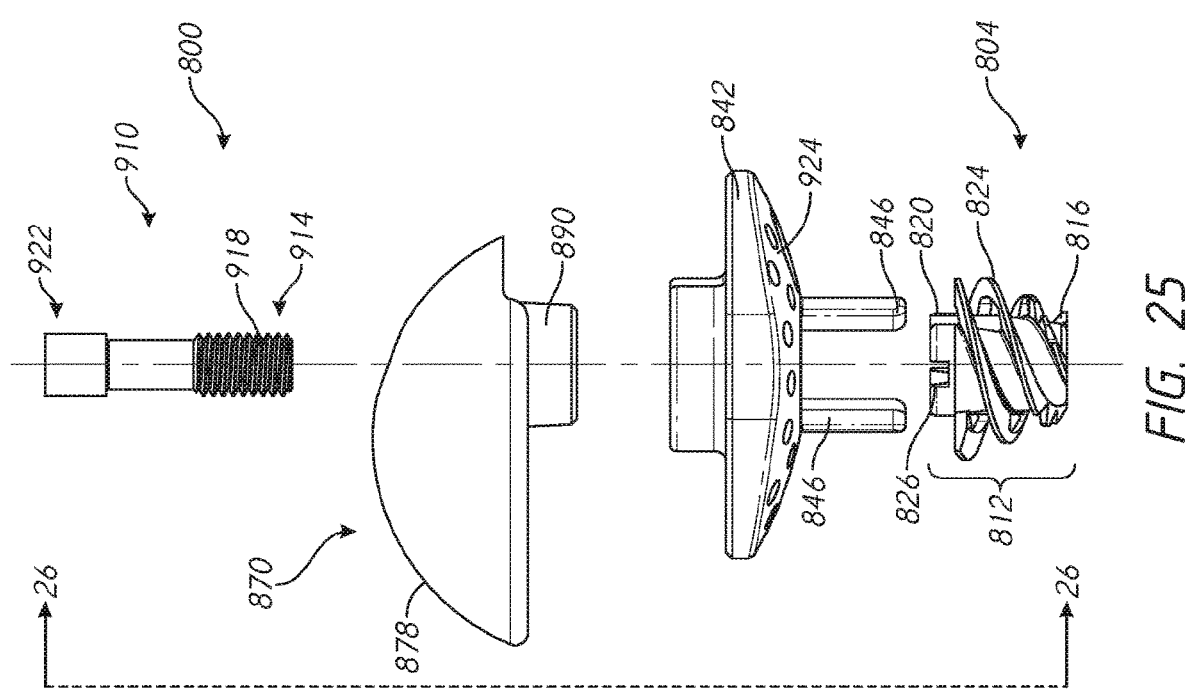

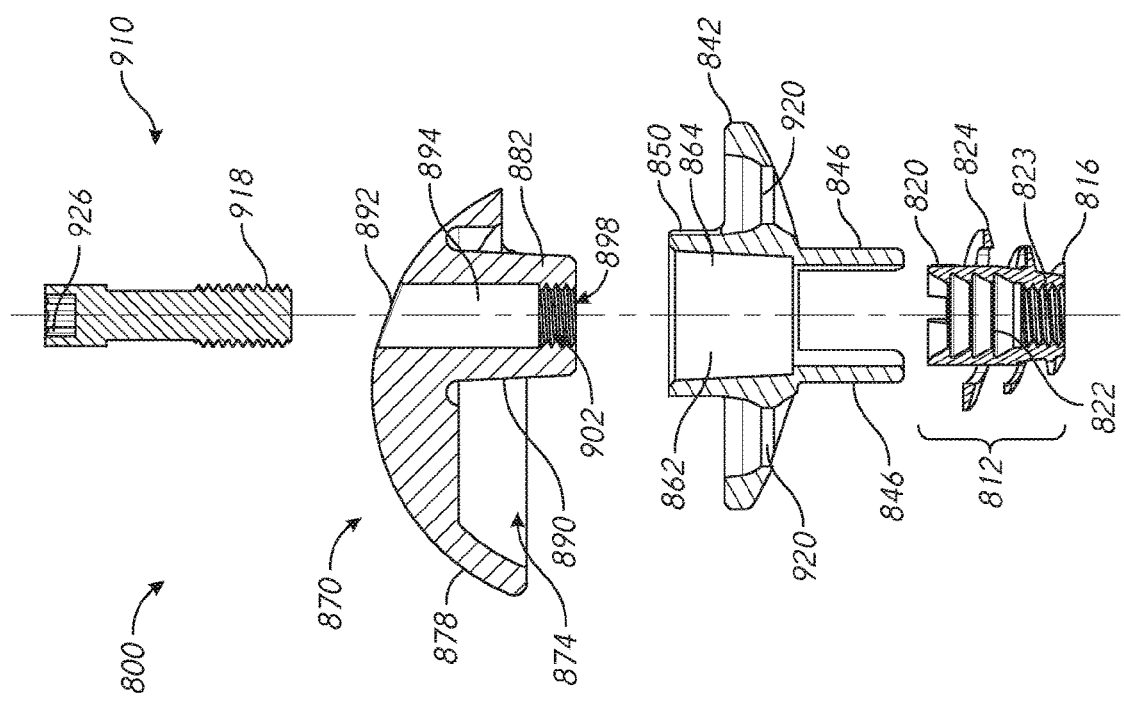

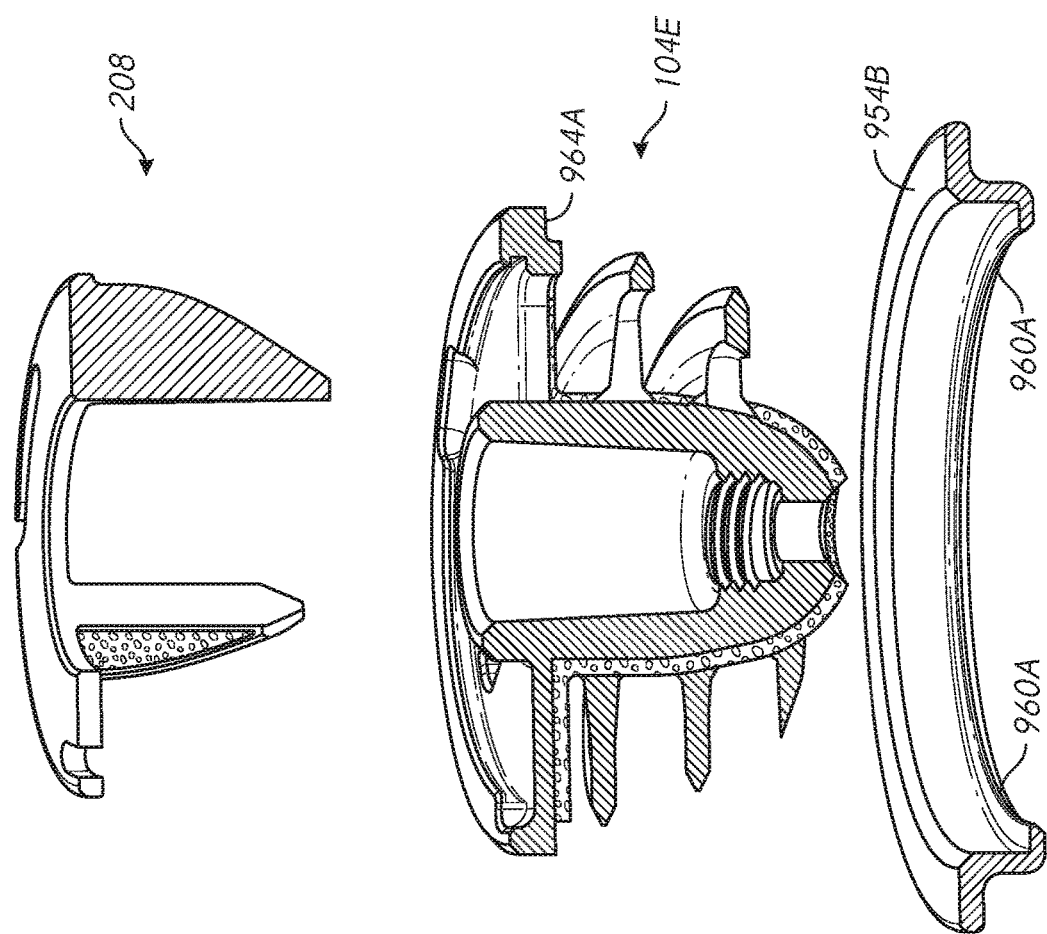

PATIENT SPECIFIC STEMLESS PROSTHESIS ANCHOR COMPONENTS

INCORPORATION BY REFERENCE TO ANY PRIORITY APPLICATIONS

This application is a National Phase Application of PCT Appl. No. PCT/US2018/052294, filed Sep. 21, 2018, which claims the priority benefit of U.S. Appl. No. 62/562,966, filed Sep. 25, 2017. Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

The present disclosure relates to a stemless prosthesis anchor component of a joint prosthesis.

Description of the Related Art

Skeletal joints have a variety of configurations providing for a wide range of smooth movement of two or more bones relative to each other. For example, in a shoulder joint, the head of the humerus interacts with the glenoid cavity of the scapula in a manner similar to a "ball and socket" joint. Over time, it may become necessary to replace a joint, such as the shoulder joint, with a prosthetic joint. The prosthetic joint can include components mounted to one, two or more than two bones at the joint. For example, the prosthetic joint can include a humeral component, a glenoid component or both a humeral and a glenoid component.

Conventional humeral components include a humeral head jointed to a stem. The stem is configured to be inserted into a medullary canal of the humerus. In certain cases, insertion of the stem disadvantageously requires bone to be removed to fit the stem to the medullary canal due to patient-to-patient anatomical variation. Another disadvantage of this approach is that integration of the stem into the bone through a natural process of bone ingrowth can make it difficult to remove the humeral component if it becomes necessary to replace the humeral component with another device.

A stemless humeral component may be used to address some of the disadvantages of conventional humeral components. Stemless humeral components can decrease the amount of bone loss in preparing the humerus to receive the component and decrease the complexity of the joint replacement procedure.

Stemless humeral component designs can be more challenging to secure to the humerus. Typically the humeral head is resected creating an exposed face. The exposed face may include cancellous bone that can degrade in certain circumstance.

SUMMARY OF THE INVENTION

Accordingly, there is a need for additional stemless components or prostheses designed to reduce bone erosion or degradation due to stress shielding and in some cases to preserve bone in initial implantation while enhancing initial pull-out and back-out resistance. The reduction of bone erosion and the enhanced pull-out and back-out resistance can be augmented in patient specific embodiments. Preferably enhanced initial dislodgement resistance will also provide excellent long term fixation.

In one embodiment, a shoulder assembly is provided that includes a base member and a locking device. The base member includes a collar, a helical structure, and a first pathway projecting distally of the collar. The helical structure extends from the collar in a distal direction. The first pathway projects distally of the collar and through the helical structure. The first pathway is disposed adjacent to an inner periphery of the helical structure. The first pathway is generally transverse to the helical structure and extending in a space between successive portions of the helical structure. The locking device has a proximal support and a first arm that projects distally of the proximal support. The first arm is configured to be disposed in the first pathway that projects distally of the collar when the proximal support is disposed adjacent to the collar. The first arm is disposed through bone in the space between successive portions of the helical structure when the shoulder assembly is implanted. At least a portion of the shoulder assembly, e.g., a portion of the collar or the helical structure, can be adapted for a specific patient based upon imaging, e.g., pre-operative or intra-operative imaging In some embodiments, a kit can be provided that includes a shoulder assembly as described above, an anatomic articular component, and a reverse articular component. The anatomic articular component is mateable with the shoulder assembly. The anatomic articular component has a convex articular surface adapted to articulate with a concave surface of or on a scapula of a patient. The reverse articular component is mateable with the shoulder assembly. The reverse articular component comprises a concave articular surface adapted to articulate with a convex surface on a scapula of a patient. The reverse articular component can include a separate tray component for mating an articular surface to the base member.

In another embodiment, a prosthesis assembly is provided that includes a base member that has a helical structure and a first pathway. The base member has a first end and a second end. The helical structure extends between the first end and the second end. The first end comprises a distal or medial end in some applications. The second end comprises a proximal end or a lateral end in some applications. The first pathway is accessible from the second end and is directed toward the first end through the helical structure. The first pathway is located inward of an outer periphery of the helical structure, e.g., adjacent to an inner periphery of the helical structure. The first pathway is generally transverse to the helical structure. The first pathway extends in a space between successive portions of the helical structure. The prosthesis assembly includes a locking device that has a support member and a first arm that projects away from the support member. The first arm is configured to be disposed in the first pathway when the support member is disposed adjacent to the second end of the base member. The first arm is disposed through bone in the space between successive portions of the helical structure when the prosthesis assembly is implanted. At least a portion of the prosthesis assembly, e.g., a portion of the base such as the helical structure, can be adapted for a specific patient based upon imaging, e.g., pre-operative or intra-operative imaging The prosthesis assembly discussed above can be mated with a proximal humerus. The prosthesis assembly discussed above can be mated with other anatomy as well, such as a glenoid of a scapula. The prosthesis assembly discussed above can be mated with a bone adjacent to an elbow joint, such as a distal humerus or a proximal radius. The prosthesis assembly discussed above can be mated with a bone adjacent to a wrist joint, such as a distal radius. The prosthesis assembly discussed above can be mated with a bone adjacent to the hip, such as a proximal femur. The prosthesis assembly discussed above can be mated with a bone adjacent to a knee joint, such as a distal femur or a proximal tibia. The prosthesis assembly discussed above can be mated with a bone adjacent to an ankle joint, such as a distal tibia or a proximal talus If the prosthesis assembly has a portion that is adapted for a specific patient based upon imaging, e.g., pre-operative or intra-operative imaging that portion can reflect the underlying anatomy of the bone portion to which they are to be attached, including for example the glenoid, the scapula, the distal humerus, the proximal or distal radius, the proximal or distal femur, the proximal or distal tibia or talus, among others.

In another embodiment, a method of implanting a prosthesis is provided. The method includes advancing by rotation a base member into a bone adjacent to a joint. The bone can include an epiphysis of a humerus of a patient. The bone can include a glenoid of a scapula of a patient. The bone can include a distal portion of a humerus adjacent to an elbow joint. The bone can include a proximal portion of a radius adjacent to an elbow joint. The bone can include a distal portion of a radius adjacent to a wrist joint. The bone can include a proximal portion of a femur adjacent to a hip joint. The bone can include a distal portion of a femur adjacent to a knee joint. The bone can include a proximal portion of a tibia adjacent to a knee joint. The bone can include a distal portion of a tibia adjacent to an ankle joint. The bone can include a proximal portion of a talus adjacent to an ankle joint. The base member comprising a helical structure configured to engage cancellous bone of the epiphysis or other portion of any of the bones set forth above. In some embodiments the method can involve placing and/or positioning a collar and/or a trunnion relative to specific anatomy to be covered thereby. For example, a patient specific trunnion can be placed over an exposed face of the bone and can be aligned with a portion potentially subject to stress shielding, such as a medial calcar of the specific patient being treated. A locking device is advanced by linear translation into the base member. The locking device has at least one arm adapted to span a gap between adjacent portions of the helical structure. The locking device contacts the cancellous bone in the gap.

In another embodiment, a glenoid assembly is provided. The glenoid assembly includes a base member and a plate member. The base member has a medial end and a lateral end. The base member has a helical structure that extends between the medial end and the lateral end and a first pathway. The first pathway is accessible from the lateral end and is directed toward the medial end. The first pathway can extend through the helical structure and can be located inward of an outer periphery of the helical structure, e.g., adjacent to an inner periphery of the helical structure. The first pathway can be generally transverse to the helical structure and can extend in a space between successive portions of the helical structure. The plate member has a flange and a first arm that projects away from the flange. The first arm is configured to be disposed in the first pathway when the plate member is disposed adjacent to the lateral end of the base member. The first arm is disposed through bone in the space between successive portions of the helical structure when the prosthesis assembly is implanted. At least a portion of the glenoid assembly, e.g., a portion of the plate member or flange or the helical structure, can be adapted for a specific patient based upon imaging, e.g., pre-operative or intra-operative imaging of the scapula.

In another embodiment, a stemless humeral anchor is provided that includes a first end, a second end, a mating portion, a collar and a rotation control feature. The first end is configured to be embedded in a proximal portion of a humerus. The second end is disposed opposite the first end. The mating portion has a central recess that extends from the second end toward the first end. The collar is disposed at the second end. The collar is disposed around the mating portion. The collar extends generally transverse to a longitudinal axis of the recess. The rotation control feature can be disposed between the collar and the first end. The rotation control feature can be configure to resist rotation of the stemless humeral anchor when the stemless humeral anchor is implanted. At least a portion of the stemless humeral anchor is adapted for a specific patient based upon imaging, e.g., pre-operative or intra-operative imaging.

The collar of the stemless humeral anchor is configured to rest on an exposed face of a humerus following resection of the humerus in one embodiment. The collar is configured to be inset in the exposed face of the humerus in one application.

The rotation control feature can include one or a plurality of arms. The arm or an arm of a plurality of arms can project from the mating portion and/or from the collar distally of the collar. The rotation control feature can include one or a plurality of fins. The rotation control feature can include one or a plurality of flanges.

In another embodiment a shoulder assembly is provided that includes a base member and a locking device. The base member has a first end, a second end, a mating portion, and a helical structure. The second end is spaced away from the first end. The mating portion has a central recess that extends from the second end toward the first end. The helical structure extends from the second end toward the first end. The locking device has a support and an arm that projects away from the support. The arm is configured to project from the second end toward the first end to be disposed within the helical structure when the support is coupled with the base member. The arm is disposed through bone in the space between successive portions of the helical structure when the shoulder assembly is implanted. At least a portion of the base member or the locking device is adapted for a specific patient based upon imaging, e.g., pre-operative or intra-operative imaging.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments. The following is a brief description of each of the drawings.

FIG. 6A-1 is a side view of a first patient specific variation of the base member of FIG. 6;

FIG. 6A-2 is a side view of a second patient specific variation of the base member of FIG. 6;

FIG. 6A-3 is a side view of a second patient specific variation of the base member of FIG. 6;

FIGS. 11-19 illustrate various methods for implanting a prosthesis assemblies of FIGS. 4-10 into a portion of a bone;

FIG. 23 is a cross-sectional view of the reverse shoulder prosthesis assembly shown in FIG. 22 taken at section plane 20-20;

FIG. 24 is an exploded perspective view of the reverse shoulder prosthesis assembly illustrated in FIG. 23 showing features of the articular surface of a glenoid sphere;

FIG. 25 is an exploded view of the reverse shoulder prosthesis assembly illustrated in FIG. 23 showing features of a bone engaging side of a plate member;

FIG. 26 is a cross-sectional view of the reverse shoulder prosthesis assembly of FIG. 23 taken at section plane 23-23 shown in FIG. 25;

DETAILED DESCRIPTION OF THE PREFERRED EMBODIMENT

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Section I (FIGS. 1-1A) of this application discusses the problem of stress shielding in the context of a humeral implant. In Section II (FIG. 4), a kit that includes both anatomic and reverse shoulder implant assemblies for treating shoulder conditions that can be, patient specific at least in part, are discussed. Section III (FIGS. 2-3) is directed to a variety of press-fit anchors that can be included in the kits discussed in Section II. Section IV (FIGS. 5-10) discusses a variety of multipart anchors that can provide advantageous bone retention even immediately following implantation. Section V (FIG. 11-21B) is directed to various methods of implanting anchors disclosed herein. Section VI (FIGS. 21-30) discusses additional apparatuses and methods that can be used for the glenoid and other bones. Section VII (FIG. 31) discusses the retention performance of embodiments disclosed herein. Section VIII (FIGS. 32-32J) discuss multi-part implants configured to reduce, minimize or eliminate stress shielding.

I. Stress Shielding and Bone Erosion at Resection Surface

Figure 1A:
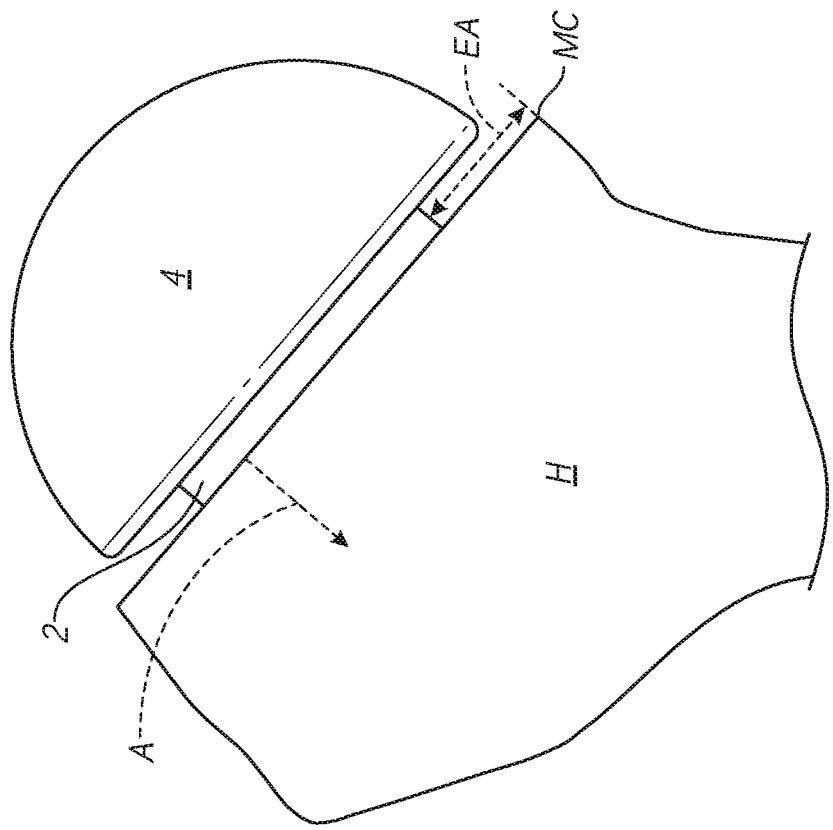
FIG. 1A shows the stemless humeral assembly implanted on an exposed face of a humerus.
Figure 1:
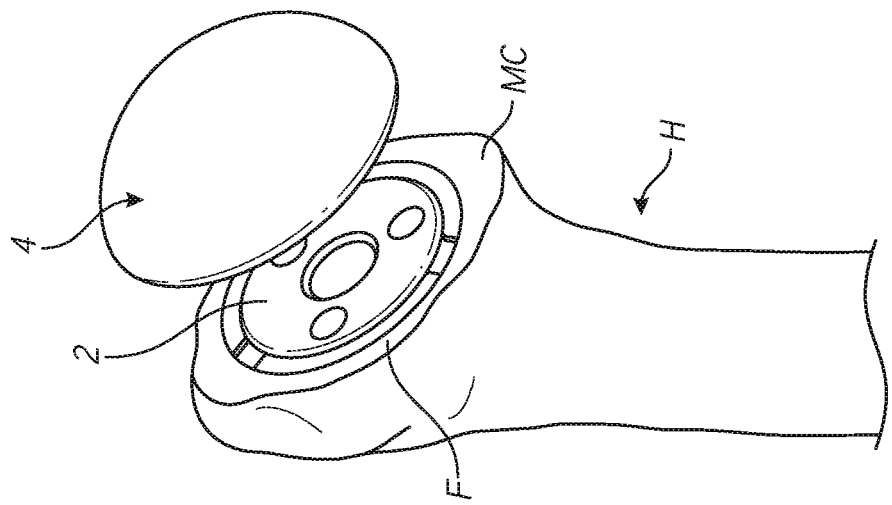
FIG. 1 is a schematic perspective view of a portion of a procedure for implanting a stemless humeral assembly.
Figure 2:
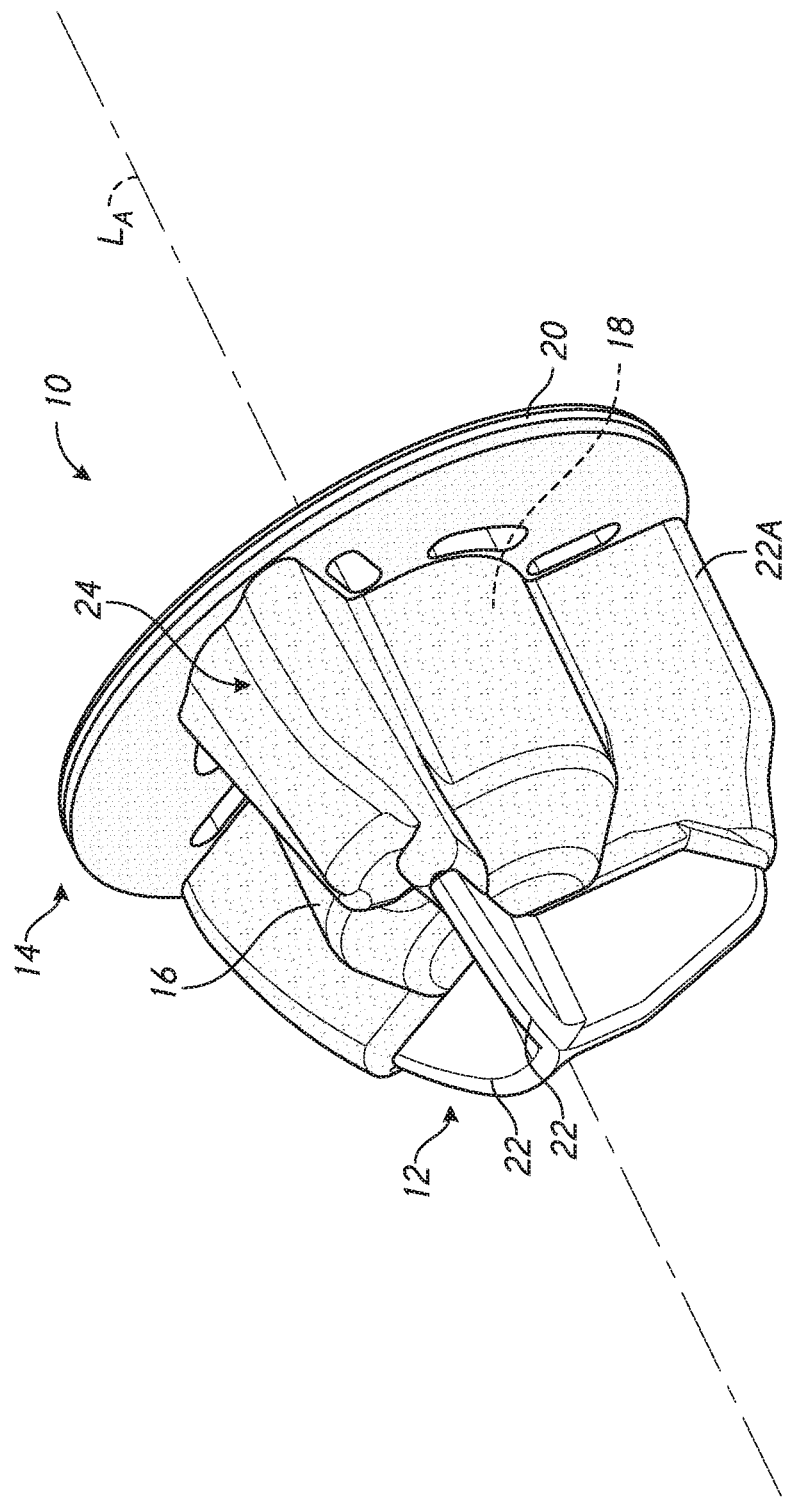
FIG. 2 is a perspective view of one embodiment of a press-fit stemless anchor with a patient specific augmentation of an embedded member.
Figure 3:
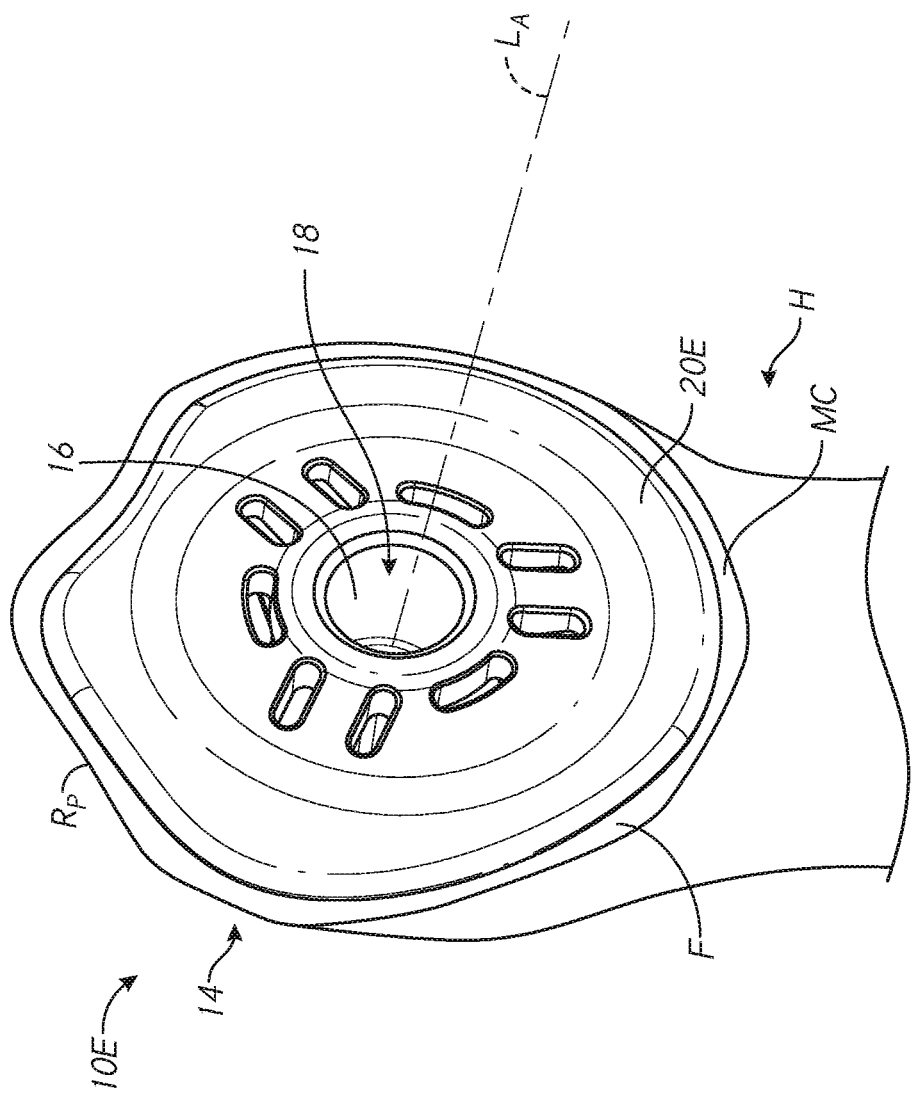
FIG. 3 is perspective view of another embodiment of a press-fit stemless anchor with a patient specific collar configured to match a peripheral shape of the resected humerus of the specific patient.

FIGS. 1 and 1A illustrate a problem that can arise from excessive stress shielding following implanting of a stemless humeral assembly. As will be discussed in greater detail below, a humeral anchor 2 and an articular component 4 can be implanted in a proximal humerus H following the resection of the humeral head. The humeral anchor 2 may be a stemmed or stemless anchor. FIGS. 2-3 illustrate various press-fit stemless configurations and FIGS. 4-32I illustrate various two part stemless anchors.

FIGS. 1 and 1A show that the resection typically creates an exposed face F. If the humeral anchor 2 has a lateral outer periphery that is much smaller than the periphery of the humeral head at the exposed face F, at least a peripheral portion of the face F can continue to be exposed after the anchor 2 is placed. For example, FIG. 1 shows that an annulus of the exposed face F that continues to be exposed following implantation of the anchor 2. The annulus is seen between the outer periphery of the anchor 2 and the outer periphery of the face F. FIG. 1A shows that the annulus can have a dimension EA at any rotational position about the anchor 2. The stemless humeral assembly may be designed to be implanted so that the lateral side of the articular component 4 does not come into direct contact with or has minimal direct contact with the face F when the component 4 is secured to the anchor 2. If the outer periphery of the articular component 4 is larger than that of the anchor 2 there can be an overhang where neither the anchor 2 nor the articular component 4 contacts the exposed face F. The overhang prevents any loads from being applied to the exposed face F in the annulus, e.g., over the dimension EA. It has been seen that when the dimension EA is too large the medial calcar region MC of the humerus can be subject to bone resorption which can compromise the integrity of the humerus following implantation of the stemless shoulder assembly.

FIG. 1A also shows the form of one head of the humerus H. As with other traits of individuals, the form of the head of the humerus H can vary for specific patients. That is, the transverse perimeter or surface area of planes parallel to the exposed face F in the direction of the arrow A may range from increasing to gradually decreasing and in some cases to rapidly decreasing in perimeter of surface area. Accordingly, the closeness in one or more of shape and radial, axial, lateral, anterior, posterior, distal, and circumferential extent of the portion of the anchor 2 below (e.g., lateral of) the exposed face F to the outside wall of the humeral head can vary by patient and if too small can compromise the integrity of the bone and/or the integrity of the fixation of the anchor 2 to the bone. If the portion of the anchor 2 below the exposed face F is spaced too far from the outside wall of the humeral head the opportunity for improved fixation in a patient with a larger humeral head is lost.

This application discusses new orthopedic assemblies that employ patient specific features to reduce stress shielding and to otherwise provide for better fit and retention of the assemblies in bone. Of particular interest is such an orthopedic assembly for use in shoulder arthroplasty, e.g., to humeral and glenoid assemblies.

II. Kits for Shoulder Arthroplasty

Figure 4:
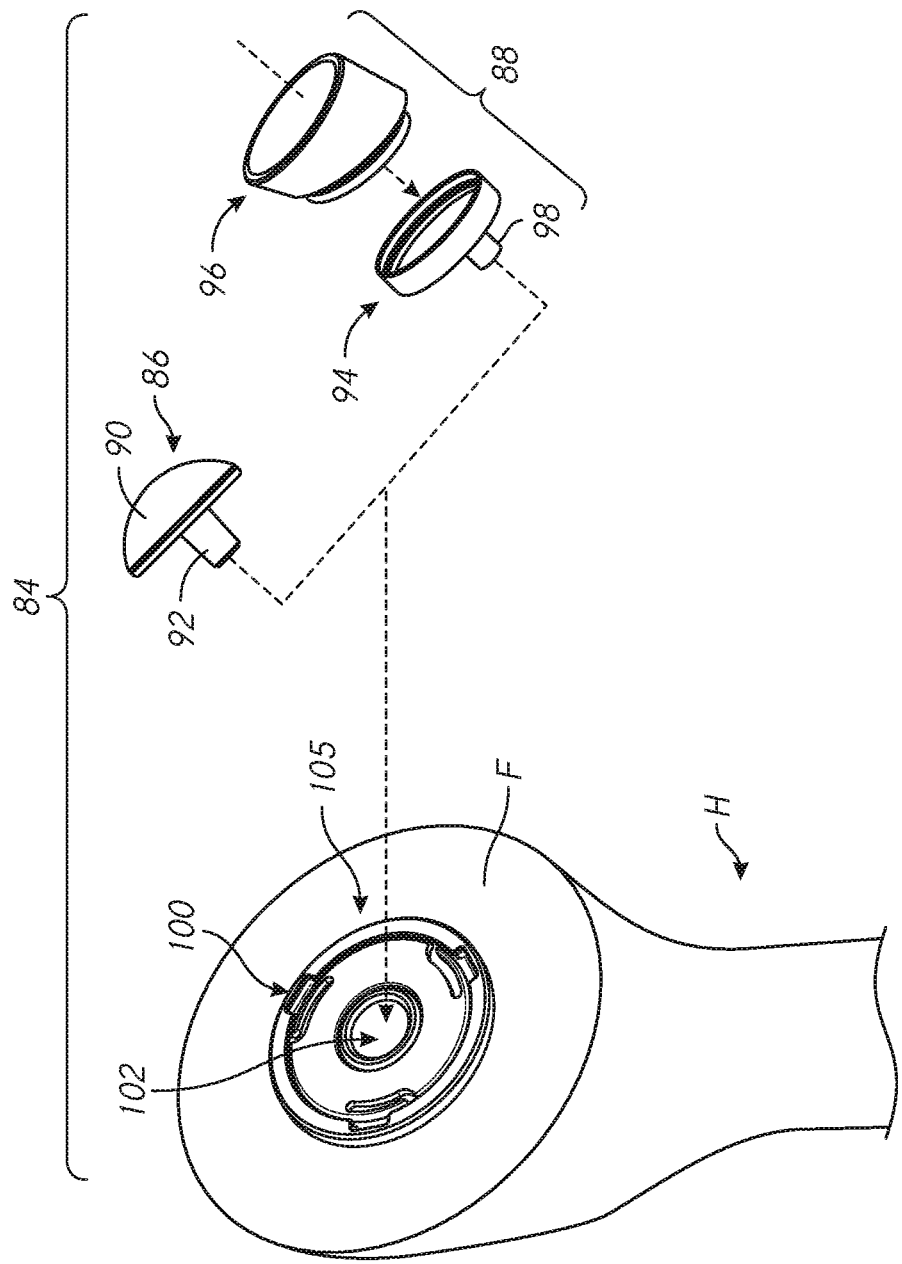
FIG. 4 is a perspective view of one embodiment of a stemless shoulder assembly shown mounted in a humerus, and further illustrating a kit including anatomic and reverse shoulder articular components.
Figure 21B:
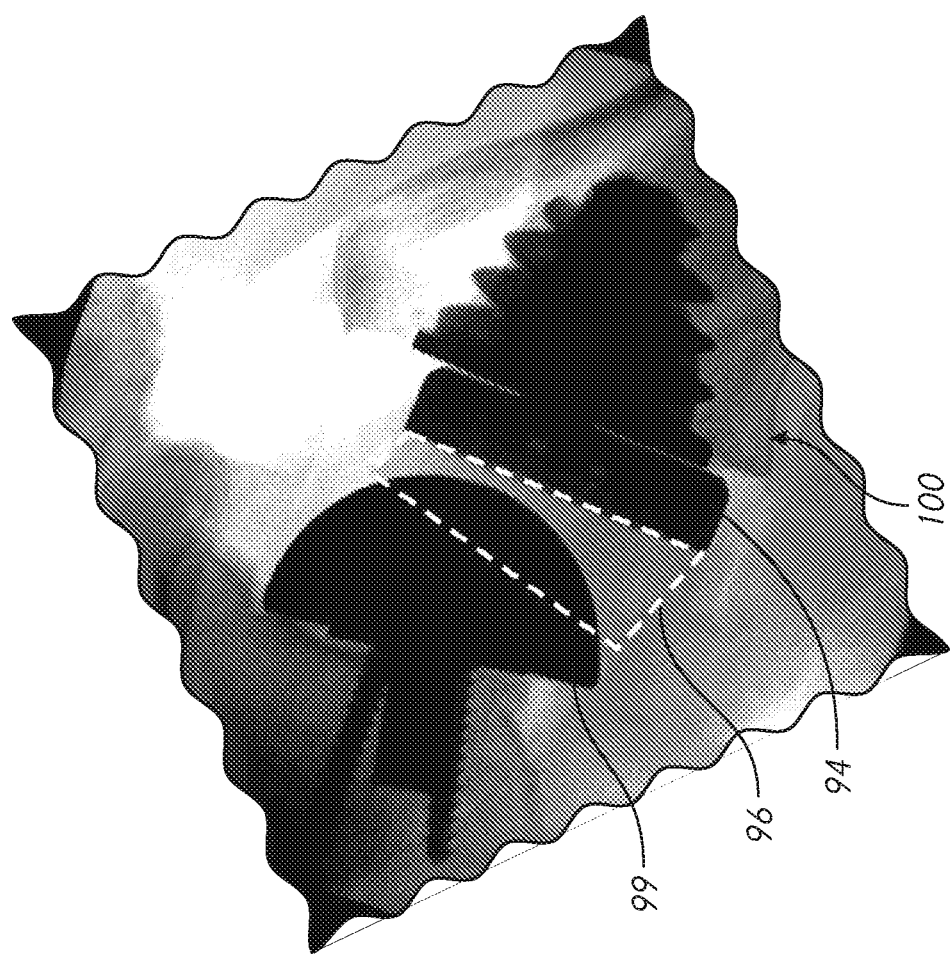
FIG. 21B shows a reverse shoulder prosthesis including a reverse articular component coupled with the humerus and a convex glenoid component, sometimes referred to as a glenoid sphere, coupled with the scapula.

FIG. 4 shows a kit 84 that includes a press-fit anchor 10 or any of the press-fit anchors 10A-10E or a shoulder assembly 100 including a base 104 or any of the bases 104A-104E. The kit can include a trunnion 954A (see FIGS. 32A and 32B) or other component that can be configured to couple with one or more of the bases 104A-104E and can be patient specific, for example having an outer periphery that reduces, minimizes or eliminate the exposed portion of the exposed face F disposed radially outward of the base. The trunnion 954A can reduces, minimizes or eliminate the dimension EA (see FIG. 1A) in the vicinity of the medial calcar MC or any other bone portion subject to erosion from stress shielding or entirely around the outer periphery of the base to which the trunnion is coupled. The kit 84 can include one or both of an anatomic articular component 86 and a reverse articular component 88. The anatomic articular component 86 can comprise a one-piece structure including a convex articular surface 90 disposed on a proximal or lateral side and a tapered projection 92 disposed on a distal side thereof. The reverse articular component 88 can comprise a two-piece structure including a tray 94 and an insert 96. In other embodiments, the articular component 88 has a one-piece configuration. In other embodiments, the articular component 88 has a monolithic configuration. Monolithic embodiments can comprise a one material configuration. Monolithic embodiments can comprise two or more material. The insert 96 can mate with the tray 94 in any suitable manner, such as by interference fit or snap fit. The tray 94 can include a tapered projection 98. FIG. 21B shows that the kit 84 also can include a glenoid sphere 99 and corresponding components for anchoring the glenoid sphere in a glenoid. The insert 96 is shown in just one embodiment in which the tray is angled, such that a plane intersecting the medial side of the insert 96 is at an angle to the side that faces the shoulder assembly 100 providing a thicker superior portion. In other embodiments the insert 96 is angled, such that a plane intersecting the medial side of the insert 96 is at an angle to the side that faces the shoulder assembly 100 providing a thicker inferior portion. In other embodiments the insert 96 is not angled, such that the plane intersecting the medial side of the insert 96 is substantially parallel to the side that faces the shoulder assembly 100.

Figure 9A:
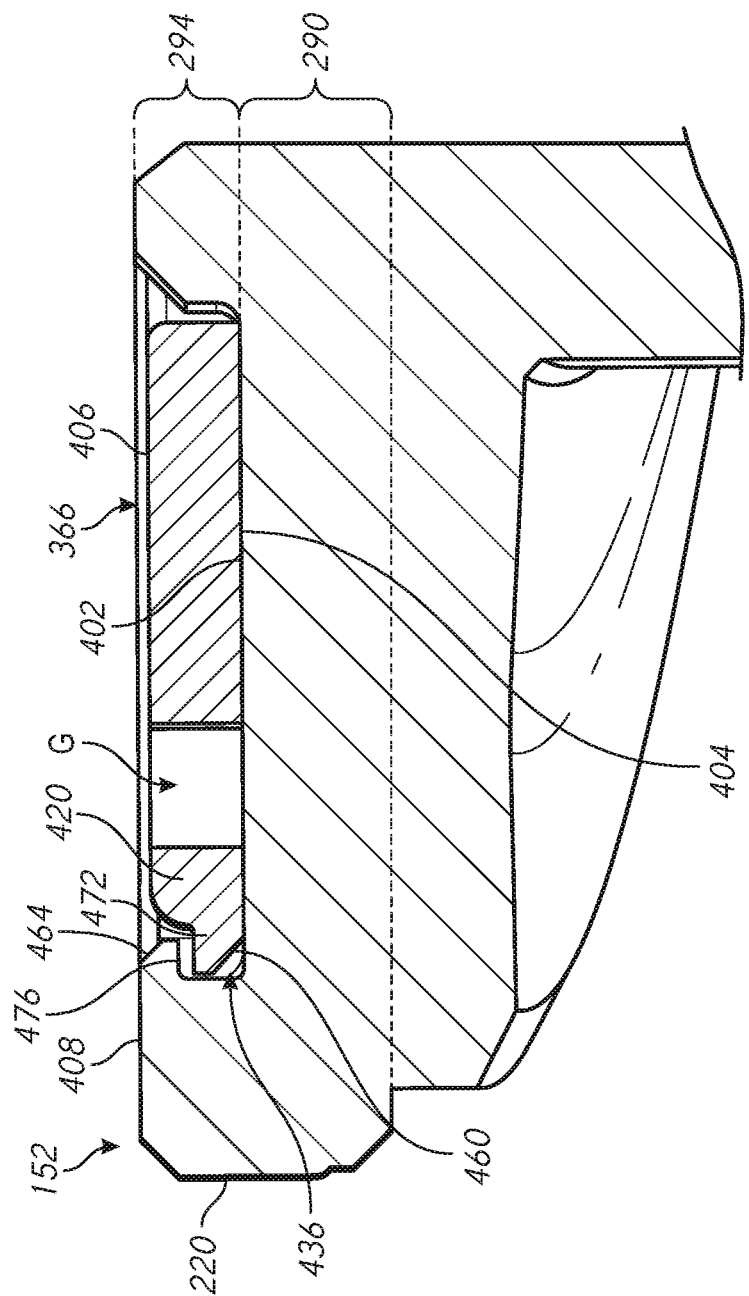
FIG. 9A is a detail view of one embodiment of an engagement feature that causes the locking component of FIG. 7 and the base member of FIGS. 6A and 6B to be engaged.
Figure 9B:
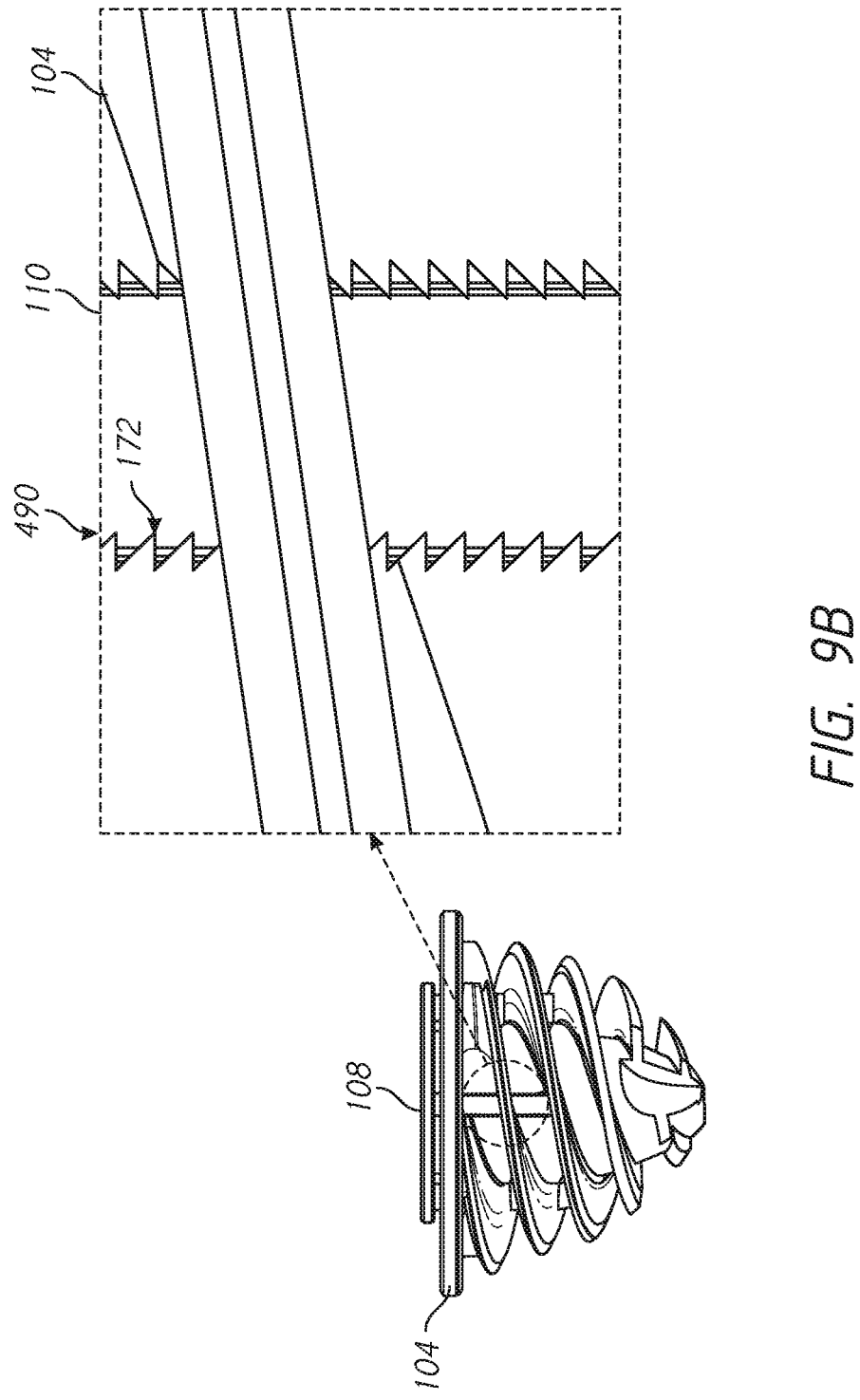
FIG. 9B is a detail view of another embodiment of an engagement feature that causes the locking component and the base member to be engaged at a location within the helical structure.
Figure 10:
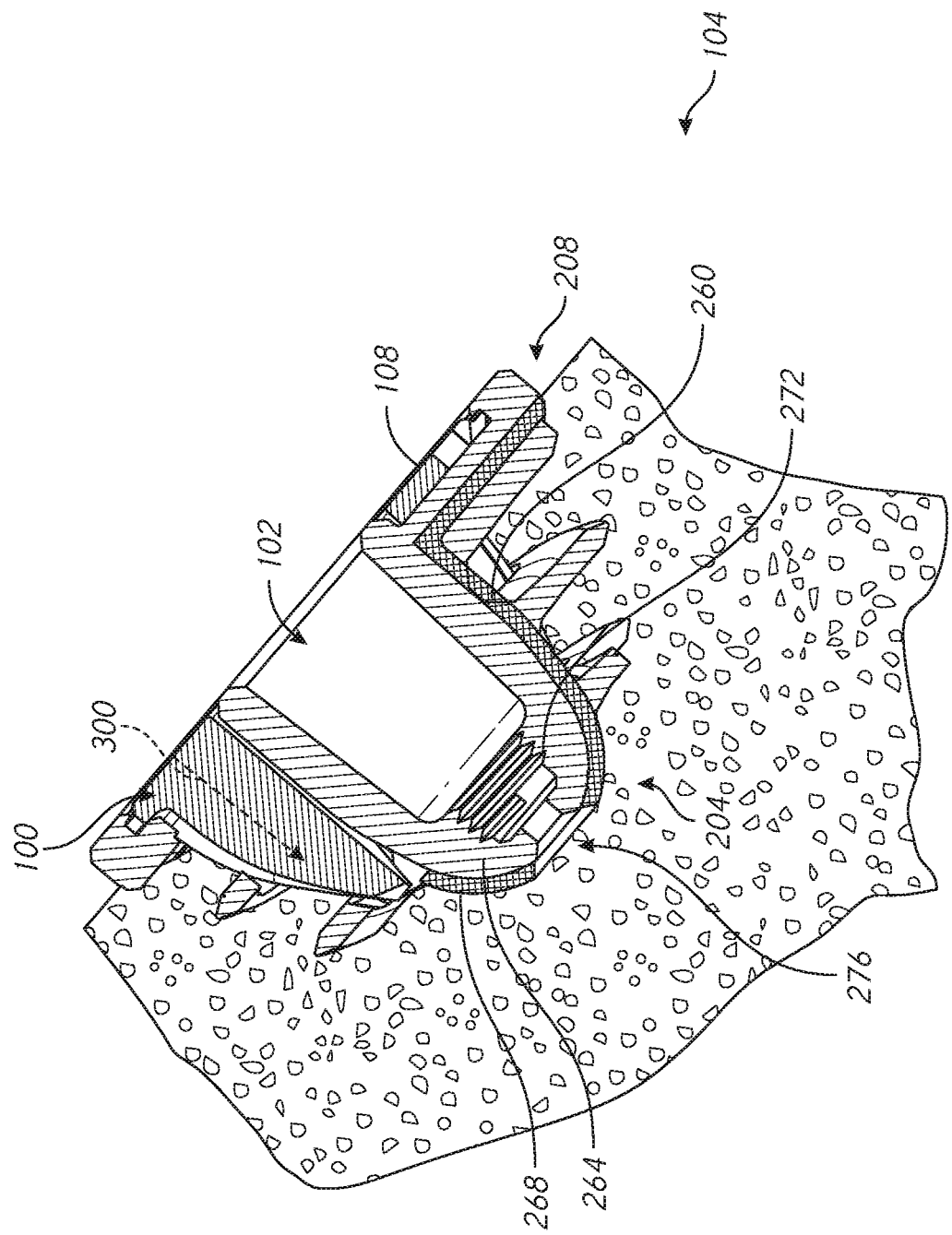
FIG. 10 is a cross-sectional view of the stemless shoulder assembly of FIG. 5 with the assembly disposed in the humeral head.
Figure 32:
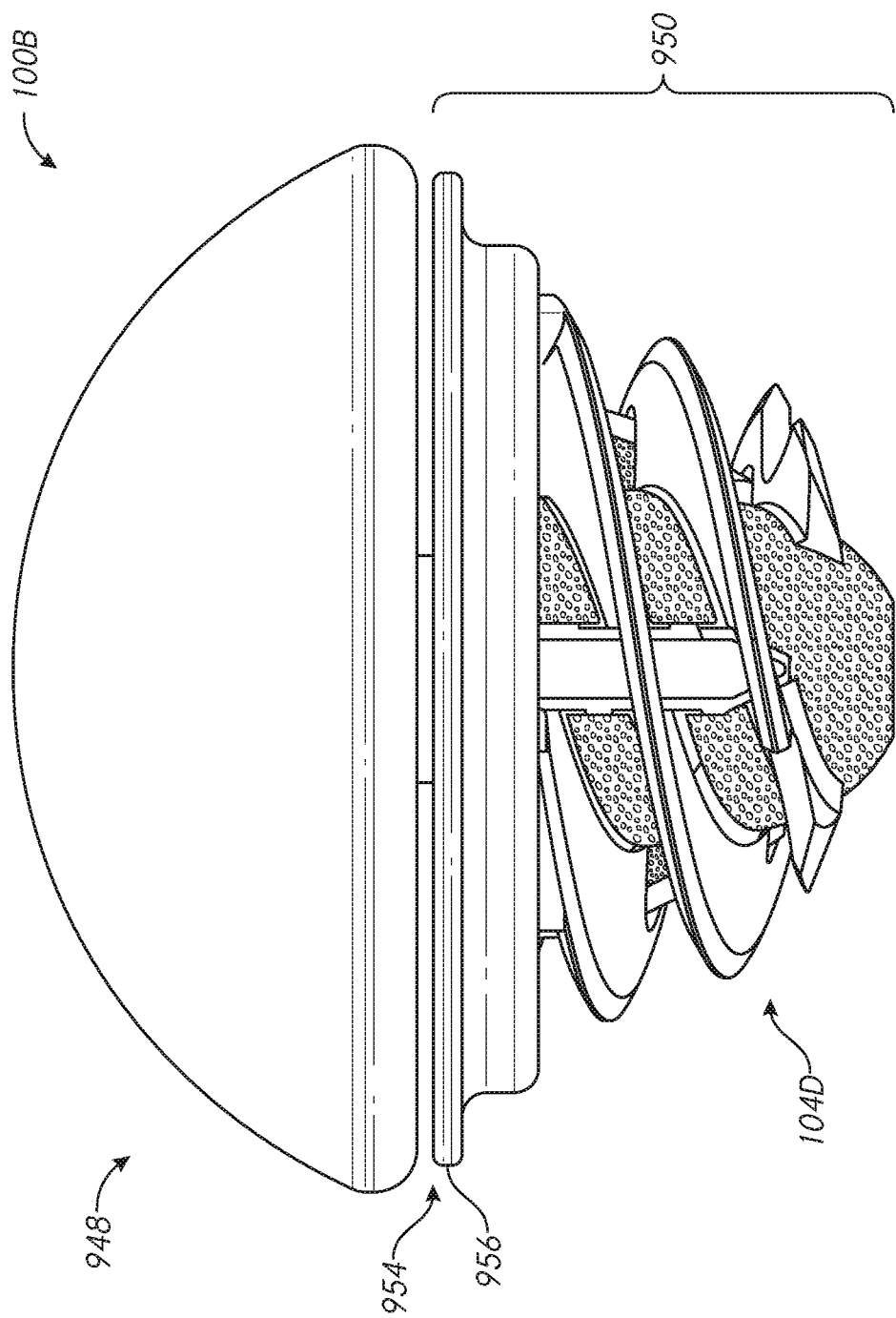
FIGS. 32-32H illustrate various features of an embodiment of a shoulder assembly configured to reduce or eliminate stress shielding in a resected humerus.

FIGS. 4 and 10 shows the shoulder assembly 100 implanted in an exposed face F of a humerus H. Various embodiments of components of the assembly 100 are shown in exploded form and separately in FIGS. 5-9B. The assembly 100 has a recess 102 in which further components of a prosthetic shoulder joint can be secured. The assembly 100 and the recess 102 enable the humerus H to be fitted with either an anatomical shoulder by receiving the anatomic articular component 86, more particularly, the projection 92 or a reverse shoulder component 88 by receiving the projection 98 either initially or as part of a revision procedure. Methods of using the kit 84 to implant the shoulder assembly 100 as part of a shoulder prosthesis are discussed below in connection with FIGS. 11-21B. FIGS. 22-30 show that embodiments of the kit can be used in orthopedic applications other than in humeral and shoulder joint procedures. FIGS. 32-32J illustrate various embodiments embodying multi-component humeral anchors some components that can be combined in a similar kit. Some of the components of various embodiments and kits can be adapted for a specific patient based upon pre-operative or intra-operative analysis of that patient's bone, e.g., CT scan, MRI, or X-ray imaging, including in some cases providing a separate flange member configured for a specific patient to extend outward an in certain applications cover the annular region of the exposed face F that in the prior art was left uncovered and subject to stress shielding. While incremental differences in these embodiments and methods are discussed below, it is to be understood that features of each embodiment can be combined with features of the other embodiments, as appropriate.

III. Patient Specific Press-Fit Humeral Anchor

FIGS. 2-3 illustrate examples of shoulder assemblies that can employ a press-fit humeral anchor 10 wherein at least a portion of the anchor 10 is adapted for a specific patient based upon pre-operative or intra-operative analysis of that patient's bone, e.g., CT scan, MRI, or X-ray imaging.

FIG. 2 shows a stemless humeral anchor 10 that can be press-fit into the humerus H. As discussed in greater detail below at least a portion of the stemless humeral anchor 10 is adapted for a specific patient following imaging, e.g., pre-operative or intra-operative imaging. The stemless humeral anchor 10 includes a first end 12 and a second end 14. The first end 12 is adapted to be embedded in the humerus H. The second end 14 is opposite the first end 12. The second end 14 is adapted to be placed at the resection plane covering at least a portion of the face F. The stemless humeral anchor 10 also includes a mating portion 16. The mating portion 16 can include a recess 18 configured to receive a corresponding mating portion of an articular component of a humeral assembly as discussed further below. The mating portion 16 can include a generally cylindrical form. In some embodiments a portion of the mating portion 16 spaced away from the second end 14 includes a tapered form.

The stemless humeral anchor 10 includes a collar 20 disposed at the second end 14. The collar 20 extends around the mating portion 16. The collar 20 extends transversely to and in some cases laterally of a longitudinal axis LA of the mating portion 16. The collar 20 is configured to rest on the exposed face F following resection of the humerus H.

The stemless humeral anchor 10 includes a plurality of arms 22. The arms 22 are examples of rotation control features that can be provided on the anchor 10. Other arms herein are also examples of rotation control features that can be provided on the anchor with which such arms are described. The arms 22 are examples of rotation control features that are fixed relative to the mating portion 16 of the anchor 10. The arms 22 are examples of rotation control features that are fixed relative to the recess 18. The arms 22 are examples of rotation control features that can extend radially away from a periphery of the anchor 10 be disposed below the resection of the humerus when implanted. The arms 22 are examples of rotation control features that can extend axially away from a distal surface of the anchor 10 to be disposed below the resection of the humerus when implanted. The arms 22 are examples of rotation control features that are unitary with the collar 20, the mating portion, and the recess 18 such that, in use, such rotation control features are inserted simultaneously into the prepared humerus as discussed further below. The arms 22 project from the mating portion 16 in some embodiments. The arms 22 extend toward the first end 12 from the collar 20 in some embodiments. The arms 22 extend toward the second end 14 from the first end 12 in some embodiments.

As noted above, at least a portion of the stemless humeral anchor 10 can be made for a specific patient following pre-operative imaging. FIG. 2 shows that the stemless humeral anchor 10 can include one or more arms 22A that has a different form or shape from one or more other arms 22. Specifically the arm 22A the can be seen to have a larger radial extent. In more detail the arms 22A can extend further away from the longitudinal axis LA than the other two arms 22 of the stemless humeral anchor 10. Also, the arms 22A can be seen to have any shape specific to pre-operative intraoperative or other imaging, including without limitation a generally straight side that extends from adjacent to the second end 14 of the stemless humeral anchor 10 toward the first end 12. The arms 22A can have a tapered edge at an end of the straight side closest to the first end 12. In contrast the other two arms 22 can be generally continuously curved from the second end 14 to the first end 12. The arms 22A can be configured to be received in a resected humerus H where additional bone mass or volume of bone is located at the position at which the arms 22A would be disposed when the stemless humeral anchor 10 is implanted. Also, the arms 22A would be accommodated in a humerus H where the outside wall thereof extends generally distally toward the shaft of the humerus H without curving rapidly inwardly. The arms 22A have a larger surface area from the mating portion 16 to the straight edge thereof than is provided in the arms 22. The arms 22A are thus able to provide greater surface area for bone ingrowth which provides a more secure connection with the cancellous bone of the humerus H. The arm or arms 22A being augmented, e.g., larger, or a different form or shape, having modified edges, provides an example of a structure configured to be disposed beneath the face F in the cancellous bone therebelow that can be enhanced for patient specific performance.

Figure 2A:
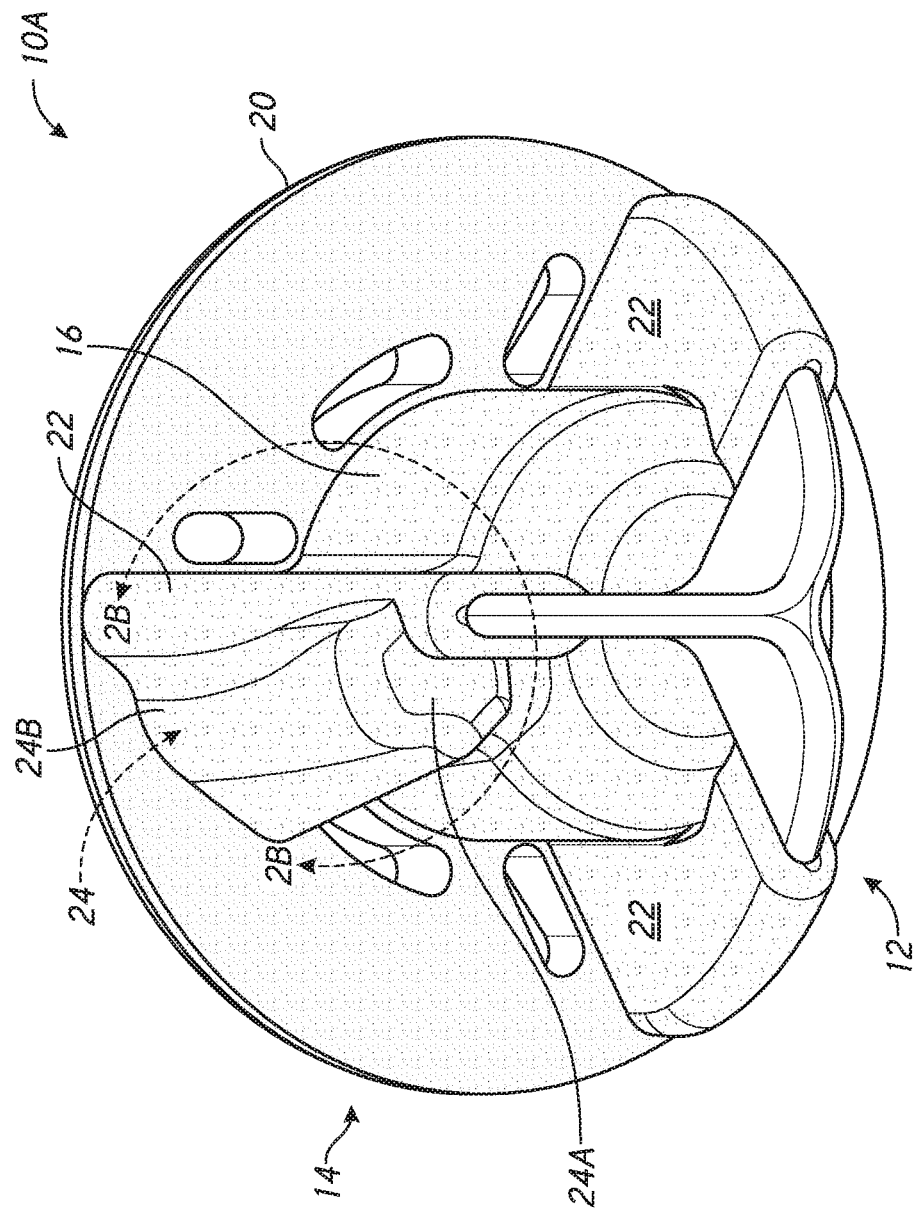
FIG. 2A is a perspective view of another embodiment of a press-fit stemless anchor with a patient specific void filling structure.

FIG. 2A shows another embodiment of a stemless humeral anchor 10A that also can be configured in a subsurface portion in a patient specific manner. The stemless humeral anchor 10A is similar to the stemless humeral anchor 10 except as described differently. The stemless humeral anchor 10A includes a void filling protrusion 24 that can be formed in a patient specific manner, utilizing, for example, 3-D printing technology. The void filling protrusion 24 can be formed with reference to pre-operative imaging such as CT scan, MRI scan, X-ray or other imaging. The void filling protrusion 24 can be used to fill a cancellous portion of bone located within the outer cortical bone layer of the humerus H. For example, prior to surgery a scan of the humerus H can be made using any suitable technology. In the scan a hollowed out area can be identified that is at distal of the resection plane forming the face F. Solidifying the cancellous bone can be confirmed as an appropriate medical objective. The three dimensional shape of the area to be solidified can be determined. That shape can be used to form the void filling protrusion 24 using any suitable technique. One approach is to use additive manufacturing, such as 3D printing or the like, to form the void filling protrusion 24 in a manner that fills the area to be solidified.

FIG. 2A shows that the void filling protrusion 24 can in one embodiment be contiguous with one of the arms 22. The void filing protrusion 24 can be contiguous with rotation control features, e.g., one of the arms 22 and extend circumferentially therefrom, e.g., toward another one of the arms 22. In other embodiments the void filling protrusion 24 can be spaced apart from the arms 22. For example, the void filling protrusion 24 can be configured as a radial protrusion from the mating portion 16. The void filling protrusion 24 can have a first end 24A and a second end 24B. The first end 24A can be located between the first end 12 and the second end 14. The second end 24B will normally be located at or adjacent to the second end 14. Extending the second end 24B to the second end 14 of the stemless humeral anchor 10A allows for some preparation of the void to be filled from the face F in a direction that is distal on the humerus H. Although FIG. 2A shows that there can be one void filling protrusion 24 on the stemless humeral anchor 10A, in other embodiments there can be more than one void filling protrusion 24. Where there are more than one void filling protrusion 24 the shape and configuration of the void filling protrusions 24 will generally be different. The void filling protrusion 24 need not extend straight from the second end 14 toward the first end 12. Instead, the void filling protrusion 24 can be curved to some extent between the second end 24B and the first end 24A. For example, the second end 24B can be spaced farther from the nearest arms 22 than is the first end 24A. The outermost radial extent of the void filling protrusion 24 between the second end 24B and the first end 24A can follow a curved contour.

Figure 2B:
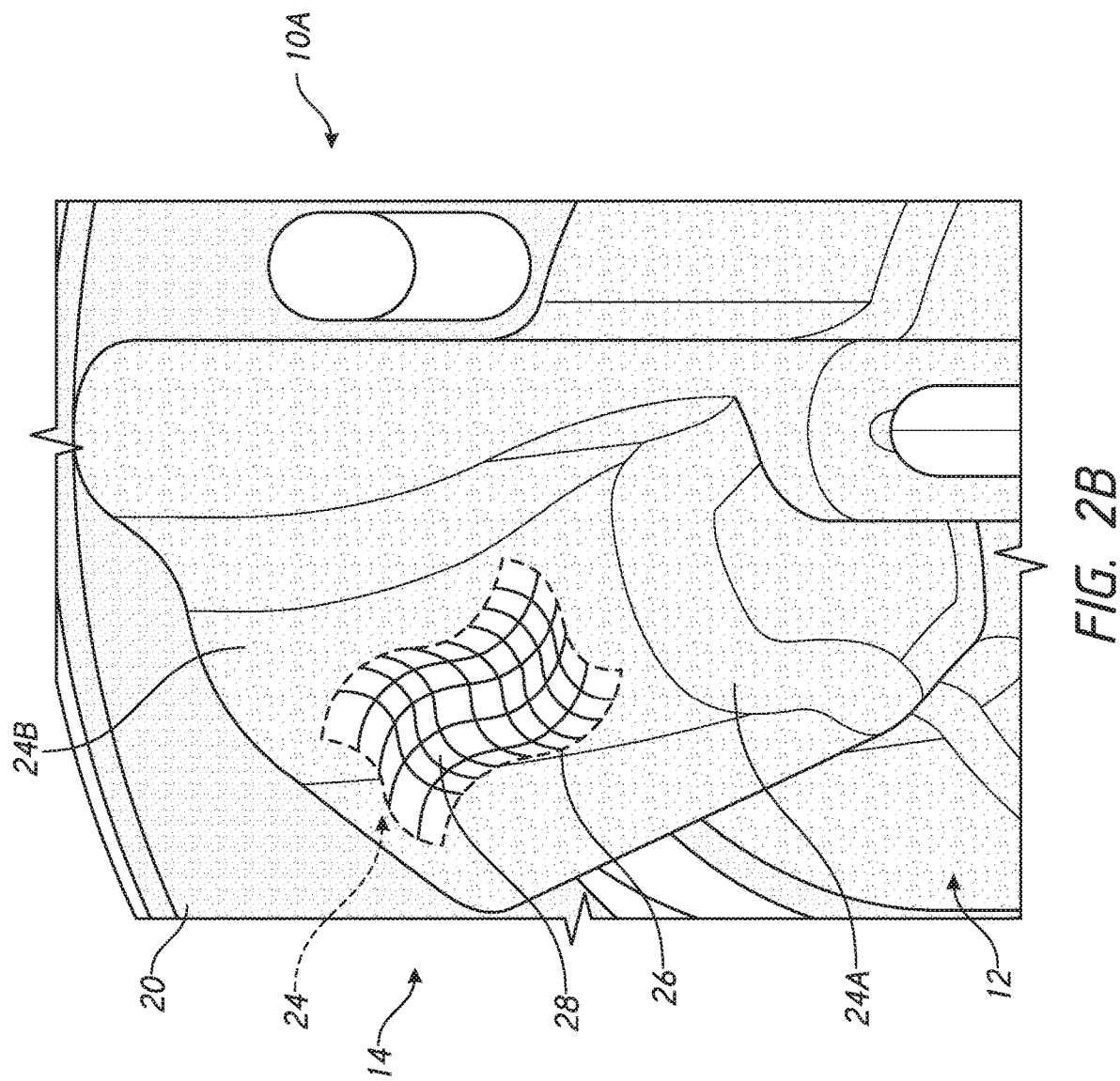
FIG. 2B is an enlarged schematic view of one embodiment of a void filling structure that can be incorporated into embodiments disclosed herein.

The void filling protrusion 24 can be configured to allow for bone ingrowth into the void filling protrusion 24. In some embodiments the void filling protrusion 24 can also be filled with matter to enhance or cause solidification of the bone matter outward of the stemless humeral anchor 10A and within the void filling protrusion 24. For example, the void filling protrusion 24 can include a porous shell 26. Although the overall structure of the bone filling protrusion 24 can be a three dimensional projection from one or more of the arms 22 or another part of the anchor 10A, at least a portion of thereof is mesh-like. FIG. 2B is a schematic representation of this mesh-like portion. The porous shell 26 can include a mesh of any suitable scale. The mesh-like structure enables the anchor 10A to retain the intended form of the protrusion 24 due to the construction there, but provides small gaps as illustrated in FIG. 2B that allow for a substance that will enhance integration with native bone by being disposed within the bone filling protrusion 24 but being able to be pressed out through the mesh-like portion into contact with the native bone or otherwise become in direct contact with the native bone. Generally the porous shell 26 is configured to retain a bone void filing component 28 but to allow the cancellous bone to extend across the porous shell 26. The porous shell 26 can be configured with a thickness in a range of 0.75 mm to 1 mm. The porous shell 26 can be configured with a thickness in a range 0.5 mm to 1.25 mm. The porous shell 26 can be configured with a thickness in a range 0.25 mm to 2.0 mm. Also, the pores that can be found in the porous shell 26 can be small enough to retain the porous shell 26 but large enough to permit bone growth across the porous shell 26.

FIG. 2B illustrates the bone void filing component 28 disposed within and contained by the porous shell 26. A kit can be provided to form the combination shown in FIG. 2B. The kit can include the stemless humeral anchor 10A (or other humeral anchor including void filling protrusion 24) and the bone void filing component 28. The bone void filing component 28 can be any suitable matter that either forms a sufficiently solid volume within, through, and/or around the stemless humeral anchor 10A (or other humeral anchor including the void filling protrusion 24). The bone void filing component 28 can include an autograft (prepared from the patient's own bone), an allograft, or any suitable synthetic biologic materials such as a sulfate-calcium phosphate composite or a combination of recombinant human platelet derived growth factor BB (rhPDGF-BB) and Beta tri-calcium phosphate (β-TCP) granules as non-limiting examples.

FIG. 2 shows that in some embodiments the stemless humeral anchor 10 can be patient specific through a variety of parameters. The stemless humeral anchor 10 is patient specific in providing at least one enlarged arm 22A. The stemless humeral anchor 10 also is patient specific in having a void filling protrusion 24 to make solid or otherwise enhance the bone mass beneath the face F. The stemless humeral anchor 10 can be further configured to be patient specific in other aspects, as are discussed herein.

Figure 2C:
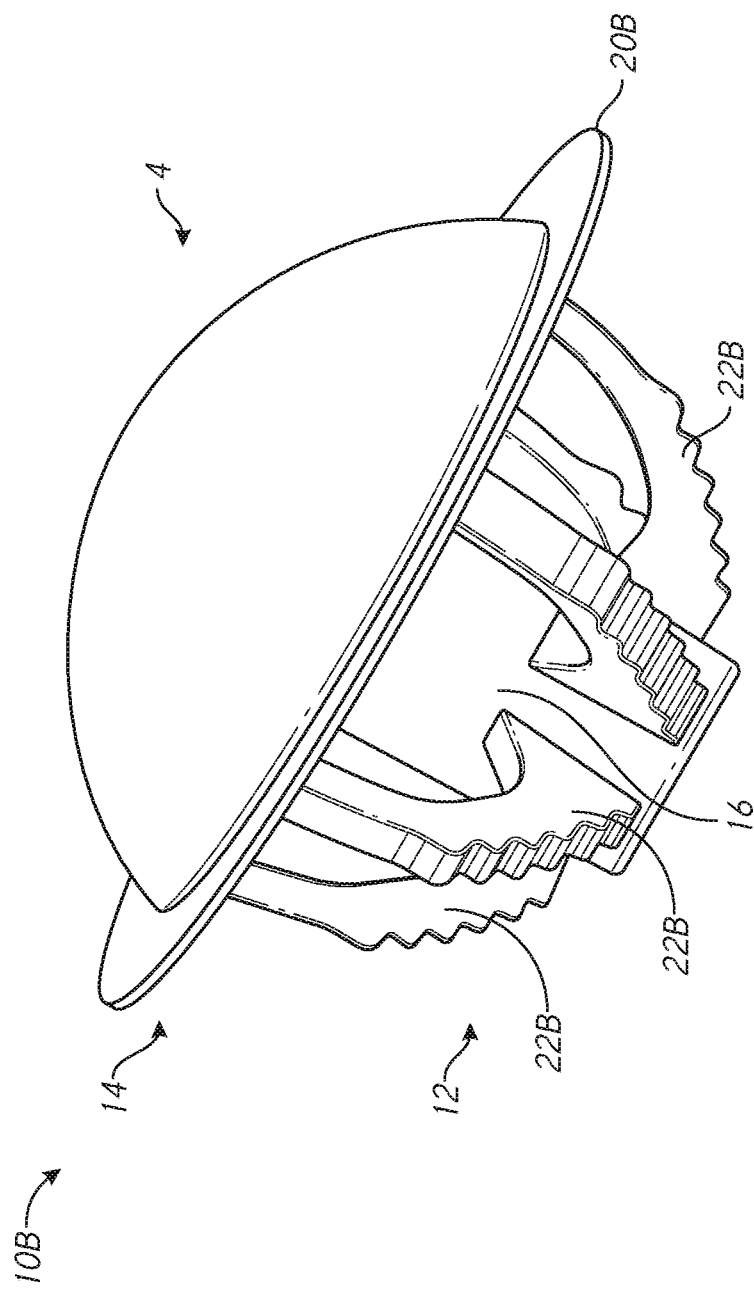
FIGS. 2C-2E illustrate various embodiments of press-fit stemless anchors with patient specific features.
Figure 2D:
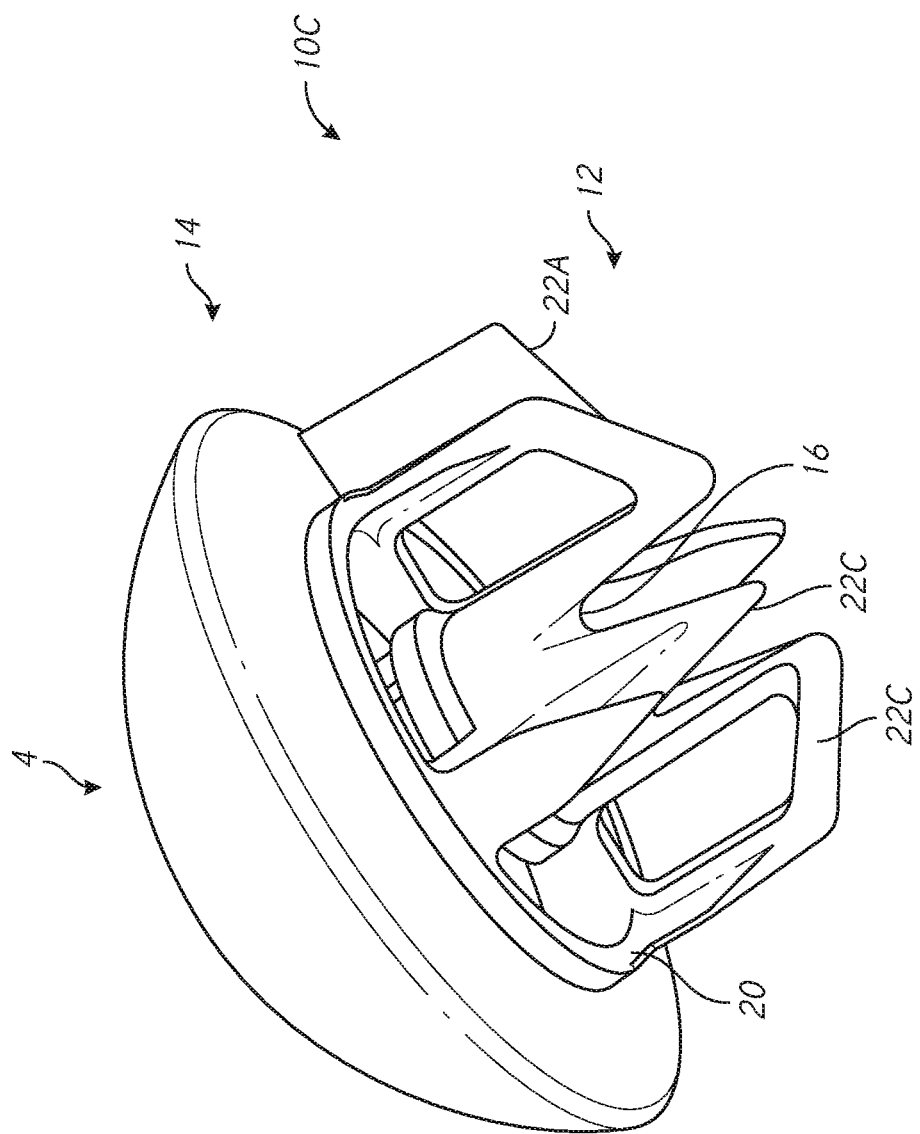
Figure 2E:
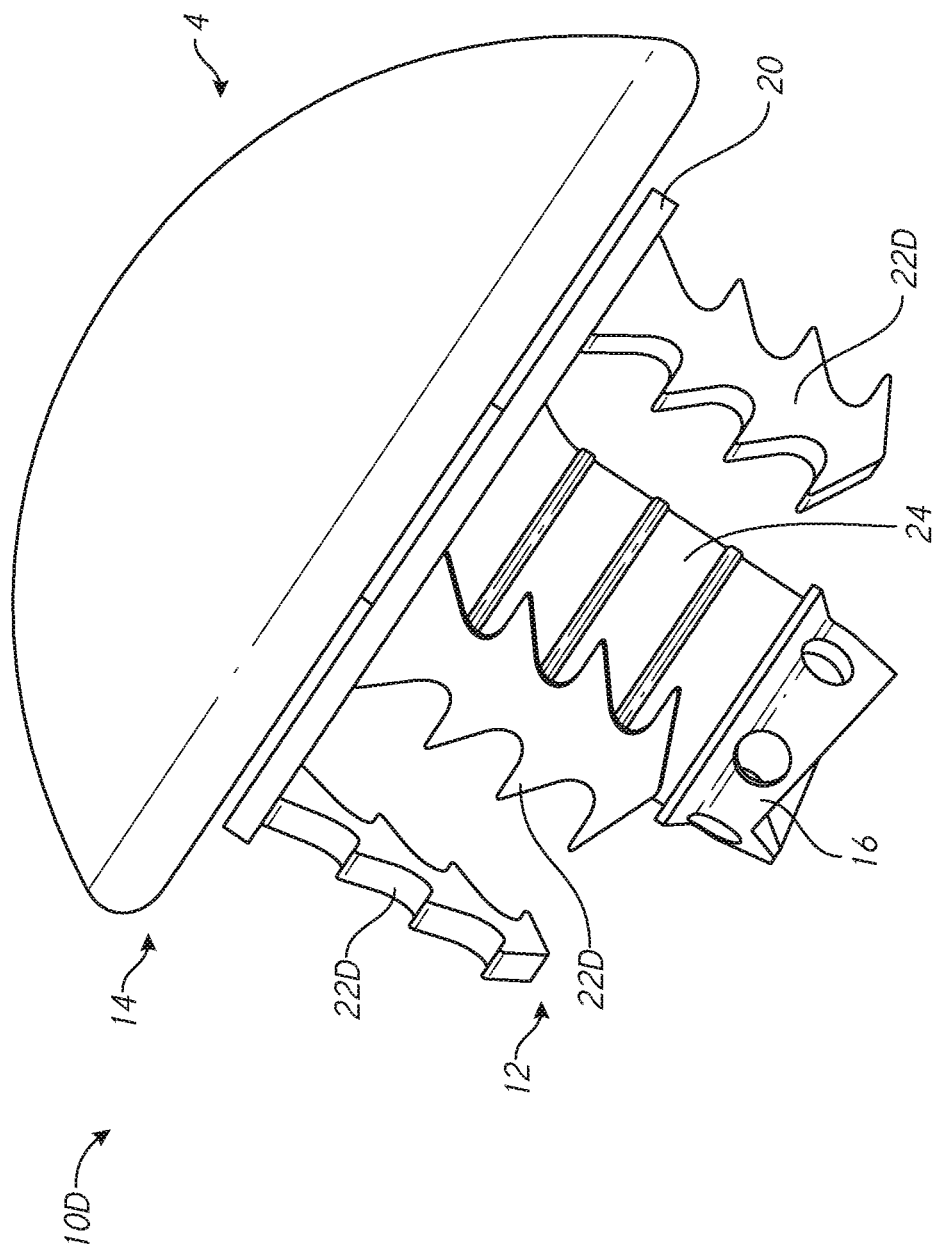

FIGS. 2C-2E show additional embodiments in which a stemless humeral anchor can be made patient specific. For example, FIG. 2C shows a stemless humeral anchor 10B that is similar to the stemless humeral anchor 10A except as described differently below. The stemless humeral anchor 10B includes a plurality of arms 22B that are coupled with a first end 12 of a mating portion 16 of the stemless humeral anchor 10B. The arms 22B each extend out from the first end 12 and curve toward the second end 14 of the stemless humeral anchor 10B. The arms 22B are different from the arms 22 in that they have a span adjacent to the second end 14 of the stemless humeral anchor 10B that is spaced apart from the mating portion 16 by a gap region. The stemless humeral anchor 10B includes a collar 20B that is patient specific in at least one manner. For example, the collar 20B can have a transverse or lateral extent that is based on the size of a perimeter RP at the resection plane. If the collar 20B has a circular outer periphery the transverse extent can include a radius that is tangential to the point of the perimeter RP closest to the center of the face F where the stemless humeral anchor 10B is to be implanted. In this manner, the most extensive coverage of the round collar 20B can be provided to the face F. As discussed more below in connection with FIG. 3 any of the collars described herein can be a shape other than round, such as an organic shape that follows the perimeter RP, e.g., maintaining a preferred annular space between the outer periphery of the collar and the perimeter RP. FIG. 2C shows the collar 20B extending radially outward of the articular component 4 for illustrative purposes. In many cases, the collar 20B will have a radius (or transverse size) that is equal to or somewhat less than the radius of the lateral side of the articular component 4.

FIG. 2D illustrates another embodiment of a stemless humeral anchor 10C that can include any of the features of other press-fit stemless implants discussed herein. The stemless humeral anchor 10C can include a plurality of arms 22C that can have a generally tapered frame profile. The arms 22C can be narrower toward the first end 12 and wider toward the second end 14 of the stemless humeral anchor 10C. The frame profile of the arms 22C can include a rigid outer periphery that surrounds an open central area. The stemless humeral anchor 10C can include one or more augmented arms 22A. The augmented arms 22A can be configured in a patient specific manner in which a dimension or portion of the arms 22A can be enlarged compared to the arms 22C. The arms 22A can extend a greater amount laterally, e.g., away from a mating portion 16 of the stemless humeral anchor 10C to engage a more voluminous portion of the humerus H distal of the face F (see FIG. 1). The stemless humeral anchor 10C can have a collar 20 that can be generic to all patients in some embodiments. In other embodiments the collar 20 can also be patient specific, e.g., enlarged for patients with larger humeral heads to reduce, minimize or eliminate stress shielding.

FIG. 2E shows another stemless humeral anchor 10D that is similar to those discussed above except as described differently. The stemless humeral anchor 10D has at least one portion that is adapted for a specific patient upon pre-operative imaging. The stemless humeral anchor 10D includes a void filling protrusion 24 that is coupled with a collar 20. The collar 20 is disposed at the second end 14 of the stemless humeral anchor 10D. The void filling protrusion 24 projects from the second end 14 toward the first end 12. The void filling protrusion 24 can be formed contiguously with a mating portion 16. The mating portion 16 can be formed in a central zone of the stemless humeral anchor 10D, e.g., projecting into the central zone of the portion of the stemless humeral anchor 10D to be disposed beneath the face F. The stemless humeral anchor 10D can include a plurality of arms 22D. The arms 22D can be of similar configuration to each other, e.g., can be generic to all or a class of patients. One or more of the arms 22D can be patient specific, e.g., having a greater extent in one or more directions than the other arms 22D to extend into more voluminous bone matter in a specific area. In some embodiments the arms 22D can have a fixed end coupled with the collar 20 and a free end spaced away from the fixed end. The free end can be sharp enough to be urged into cancellous bone. The length of the arms 22D can include one or more ribs, ridges, barbs, or other engagement features for coupling securely to the cancellous bone. The void filling protrusion 24 can be contiguous with one or more of the arms 22D or can be spaced apart from all of the arms 22D. The void filling protrusion 24 will be coupled directly or indirectly with the collar 20. The collar 20 can be enlarged to be the larger than, the same as, or nearly as large as the lateral sides of the articular component 4 to reduce, minimize or eliminate stress shielding at the face F.

FIG. 3 shows a stemless humeral anchor 10E that can include any of the features of any of the other anchors disclosed herein. The stemless humeral anchor 10E includes a second end 14 configured to be disposed at the face F. The stemless humeral anchor 10E includes a first end (not shown) but in FIG. 3 the stemless humeral anchor 10E is illustrated in the resected head of the humerus H so the first end is embedded in the bone and not shown. The first end can be similar to that of any of the foregoing anchors. The stemless humeral anchor 10E has a mating portion 16 that is accessible from the second end 14. A recess 18 is formed in the mating portion 16. The recess 18 is configured to receive a projection of an articular component to mate therewith. The recess 18 and the mating portion 16 extend along a longitudinal axis LA as shown. The stemless humeral anchor 10E includes a collar 20E that is adapted for a specific patient based upon pre-operative characterization, e.g., imaging as discussed above.

The collar 20E extends transverse to the longitudinal axis LA toward an outer periphery of the stemless humeral anchor 10E. The outer periphery of the collar 20E is configured to reduce stress shielding. For example the collar 20E can have a shape that closely matches the shape of the perimeter RP of the face F at the resection plane of the humerus H. In addition to matching the shape of the perimeter RP the collar 20E can match the size of the perimeter RP, e.g., can be large enough to extend to or nearly to the perimeter RP of the face F when the stemless humeral anchor 10E is coupled with the specific patient's humerus H. In one embodiment, the collar 20E is configured such that when properly applied to the patient a maximum gap threshold is not exceeded. In other words, the collar 20E can be configured to achieve a maximum gap below a specific amount. The maximum gap can be applied to a zone of the humerus H that is subject to erosion due to stress shielding as discussed in connection with FIG. 1A. In some cases, the maximum gap can be applied to the entire circumference of the stemless humeral anchor 10E. In other embodiments, the collar 20E can allow for lager gaps between the outer periphery thereof and the perimeter RP of the face F in zones not subject to stress shielding erosion but can be configured to assure a gap of less than 4 mm therebetween at the medial calcar MC or other zone that is subject to stress shielding erosion. In certain embodiments, the collar 20E is configured to assure a gap of less than 2 mm between the outer periphery thereof and the perimeter RP of the face F at the medial calcar MC or other zone that is subject to stress shielding erosion. In certain embodiments, the collar 20E is configured to assure a gap of less than 1 mm between the outer periphery thereof and the perimeter RP of the face F at the medial calcar MC or other zone that is subject to stress shielding erosion.

FIG. 3 shows that the perimeter RP can be rotationally asymmetric. That is, anterior and posterior halves of the perimeter RP need not match each other. Thus, the placement of the stemless humeral anchor 10E should be rotationally aligned for the specific patient. If proper rotational alignment is not provided, the eccentric shape of the collar 20E will not properly match that of the perimeter RP of the face F.

Accordingly, in methods of applying the stemless humeral anchor 10E care should be taken so that the rotational position of the collar 20E to the perimeter RP is properly provided.

IV. Humeral Shoulder Assemblies Having Rotation Control Locking Devices

FIGS. 4 and 10 show the shoulder assembly 100 applied to a shoulder joint. As discussed below in connection with FIG. 32-32J, at least a portion of the assembly 100B and various modified embodiment thereof can be adapted for a specific patient based upon pre-operative analysis of that patient's bone, e.g., CT scan, MRI, or X-ray. The assembly 100B can provide secure stemless connection to the humerus H. The shoulder assembly 100B provides for simple implantation because a base member thereof can be directly threaded into cancellous bone without being mated to another pre-placed base member. The shoulder assembly 100B can be fully retained within a head h of the humerus H. FIG. 10 shows that the distal-most portion of the assembly 100 preferably can be disposed in the humeral head h. The assembly 100 does not have a stem or other member that protrudes beyond the head h into a medullary canal of the humerus. This approach is less invasive and simpler than procedures involving placement of a stem in a medullary canal. In other embodiments illustrated in part in FIG. 13 by the creation of a recessed surface S having a depth accommodating a thickness of a proximal portion of the assembly 100, the assembly 100 may be recessed within the humeral head of the humerus H such that a proximal face 105 the assembly 100 is flush with respect to a cut surface of the bone. In other embodiments discussed herein a proximal portion of a humeral assembly can be configured to be assembled onto the resection surface following a patient specific resection as discussed in connection with FIGS. 11-11B.

Figure 5:
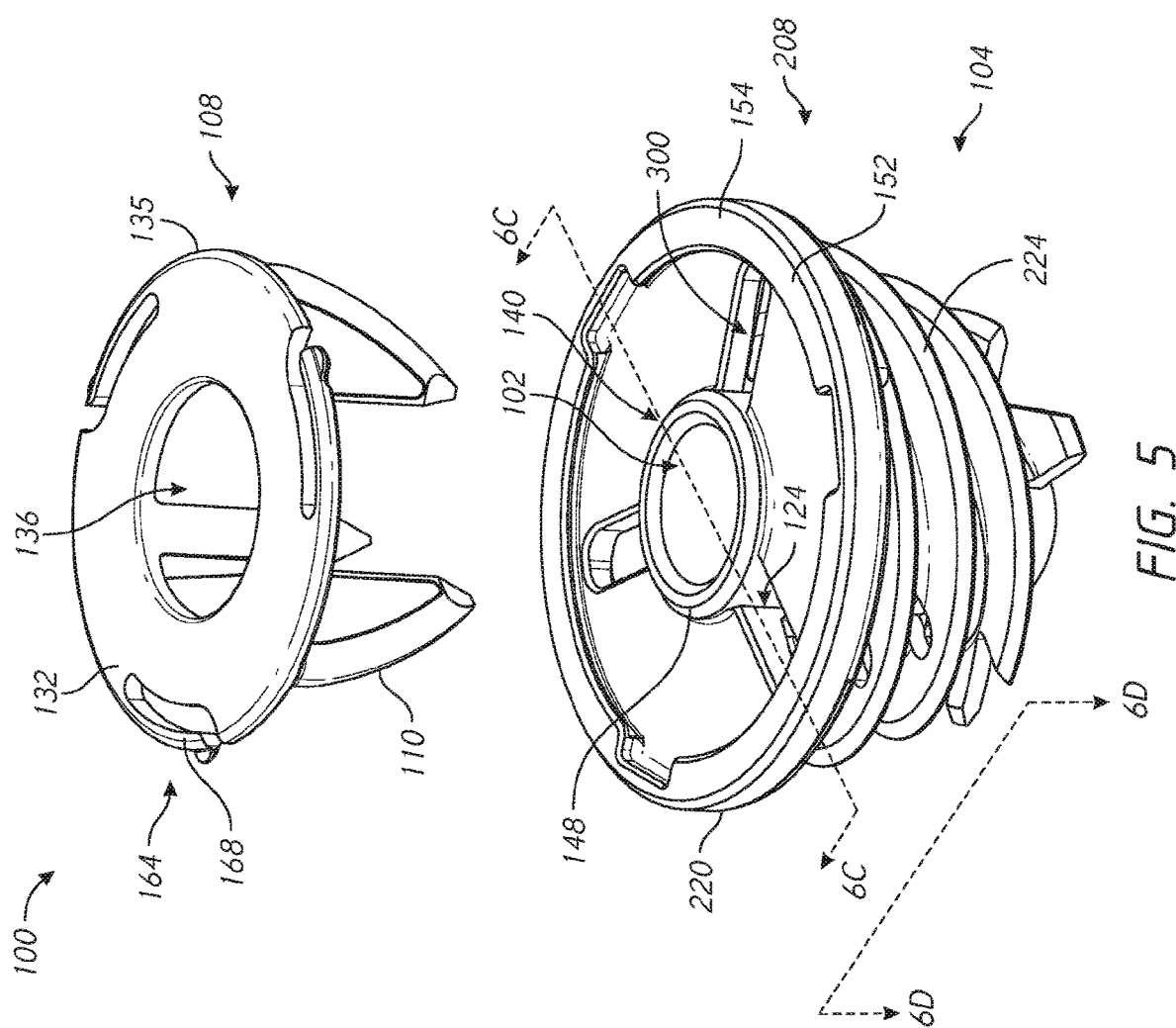
FIG. 5 is an exploded view of the stemless shoulder assembly shown in FIG. 4.

FIG. 5 shows that the assembly 100 includes a base member 104 and a locking device 108. The base member 104 is advanced into a bony structure such as cancellous bone in use. As discussed further below a bone surface may be exposed by resection or reaming, followed by threading of the base member 104 into a newly exposed bone surface. The assembly 100 also includes the locking device 108. The locking device 108 includes a plurality of arms 110. In particular, the arms 110 extend outward or distal from proximal support 132. The arms 110 can include a first arm, a second arm, and a third arm. The arms 110 can be circumferentially spaced equal distances from each other, e.g., about 120 degrees apart in one embodiment. In another variation, the arms 110 include three arms, with two of the three arms spaced 90 degrees from each other and a third arm spaced 135 degrees from one of the other two arms. The locking device 108 may include four or more arms 110. If the arms 110 include four arms, the arms can be circumferentially spaced 90 degrees apart. If the arms 110 include two arms, the arms can be circumferentially spaced 180 degrees apart. The arms 110 are advanced through apertures 124 in the base member 104. In one embodiment, it should be noted that the number of arms 110 corresponds to an equal number of apertures 124. When so advanced, the arms 110 are disposed within the base member 104 in a manner that the arms 110 cross a space between portions, e.g., successive portions, of the base member 100. When so positioned, the arms 110 are also disposed within bone. Thus, two zones of the arms 110 can cross successive or adjacent portions of the base 104 and an intervening portion of the arms 110 can cross bone in a space between the successive or adjacent portion of the base. In this position, the arms 110 control, e.g., resist, rotation of the base member 104 relative to the bone such that the shoulder assembly 100 is secured against backing out of the bone upon implantation.

FIG. 5 also shows that the locking device 108 also includes a proximal support 132. The proximal support 132 is coupled with the arms 110 in a manner discussed further below. The proximal support 132 has a central aperture 136 disposed within an inner periphery thereof and extends outward from the central aperture 136 to an outer periphery 135. The inner and outer periphery of the proximal support 132 are received in a recess 140 formed in the base member 104. In one configuration the recess 140 and the proximal support 132 are configured such that a flush connection is provided between the proximal support 132 and the proximal face of the base member 104. The proximal support 132 can be connected to the base member 104 in an at least partially recessed position in the proximal face of the base member as discussed further below in connection with FIG. 9A.

Figure 6:
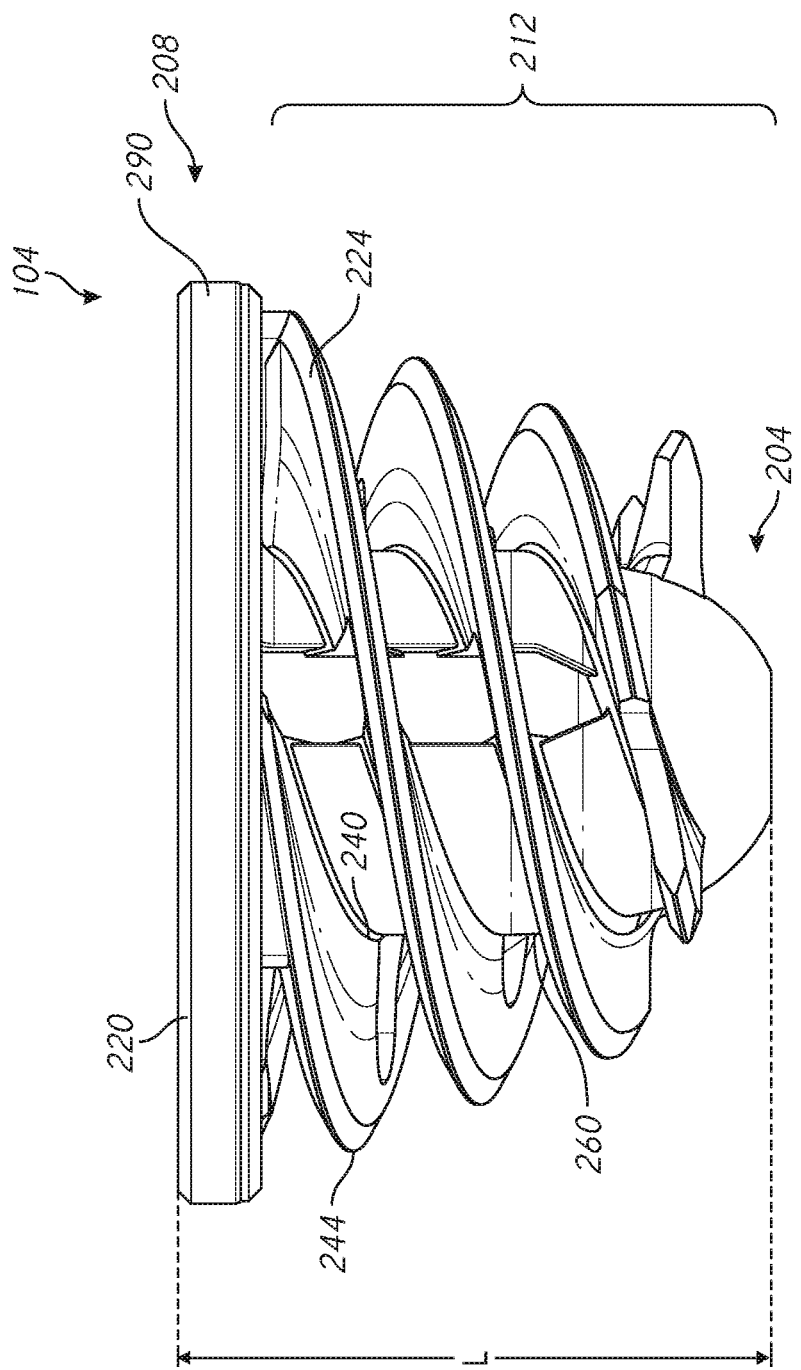
FIG. 6 is a side view of a base member of the stemless shoulder assembly of FIG. 5.
Figures 2, 6A:
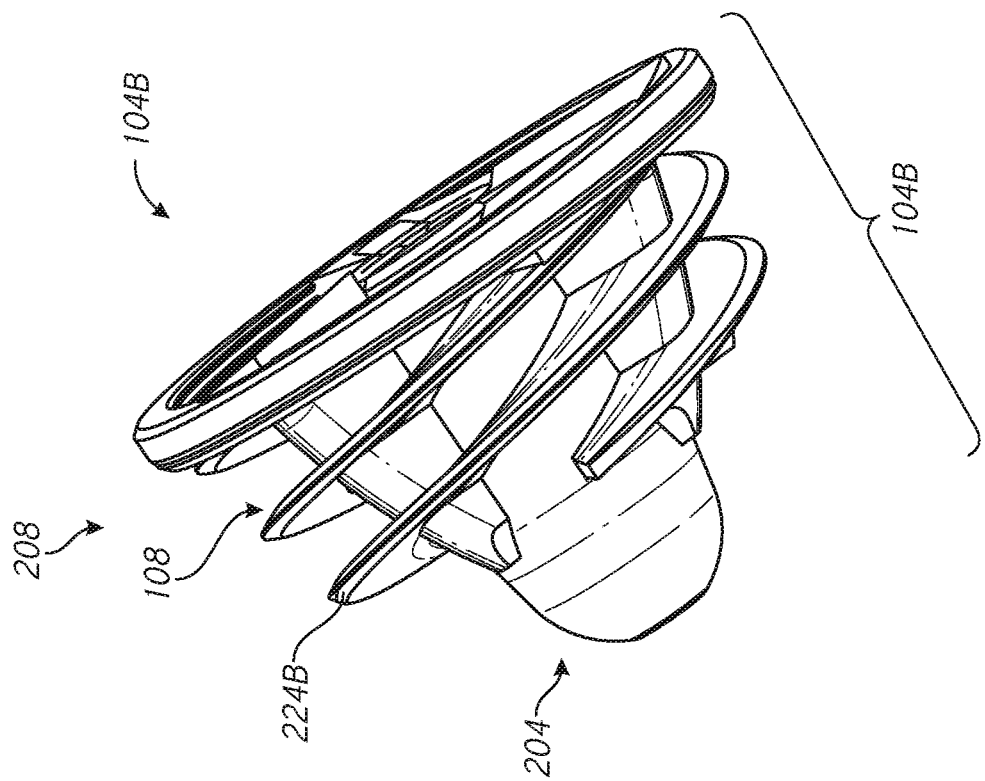
Figures 1, 6A:
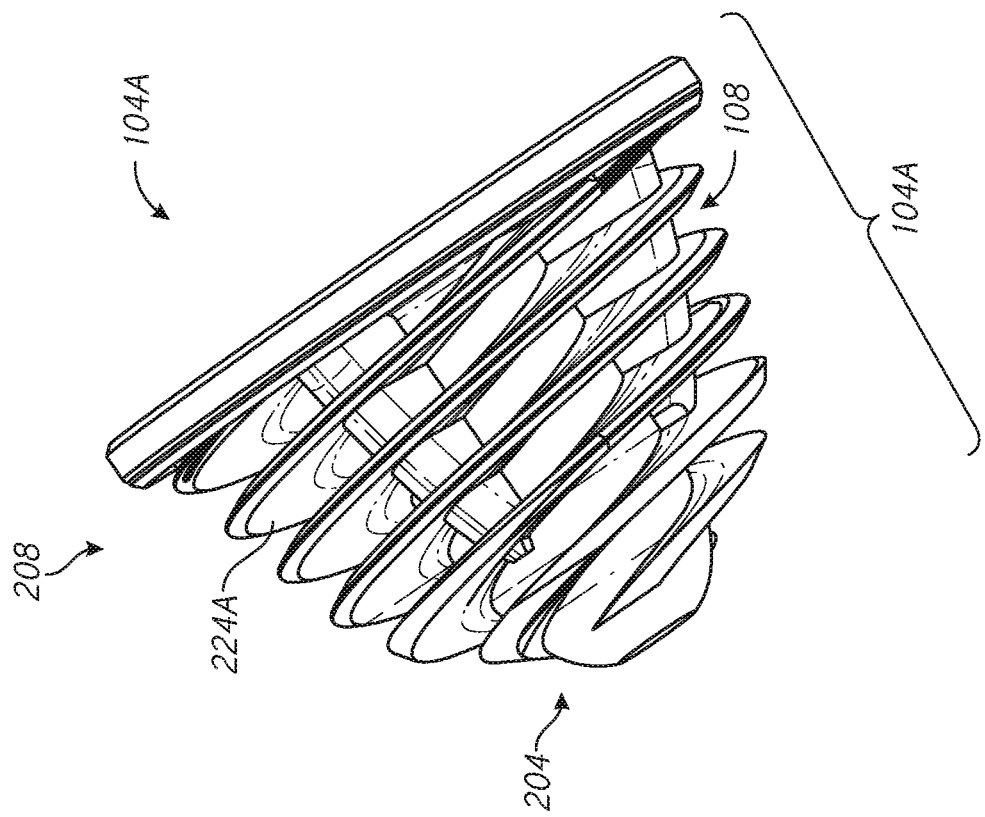
Figures 3, 6A:
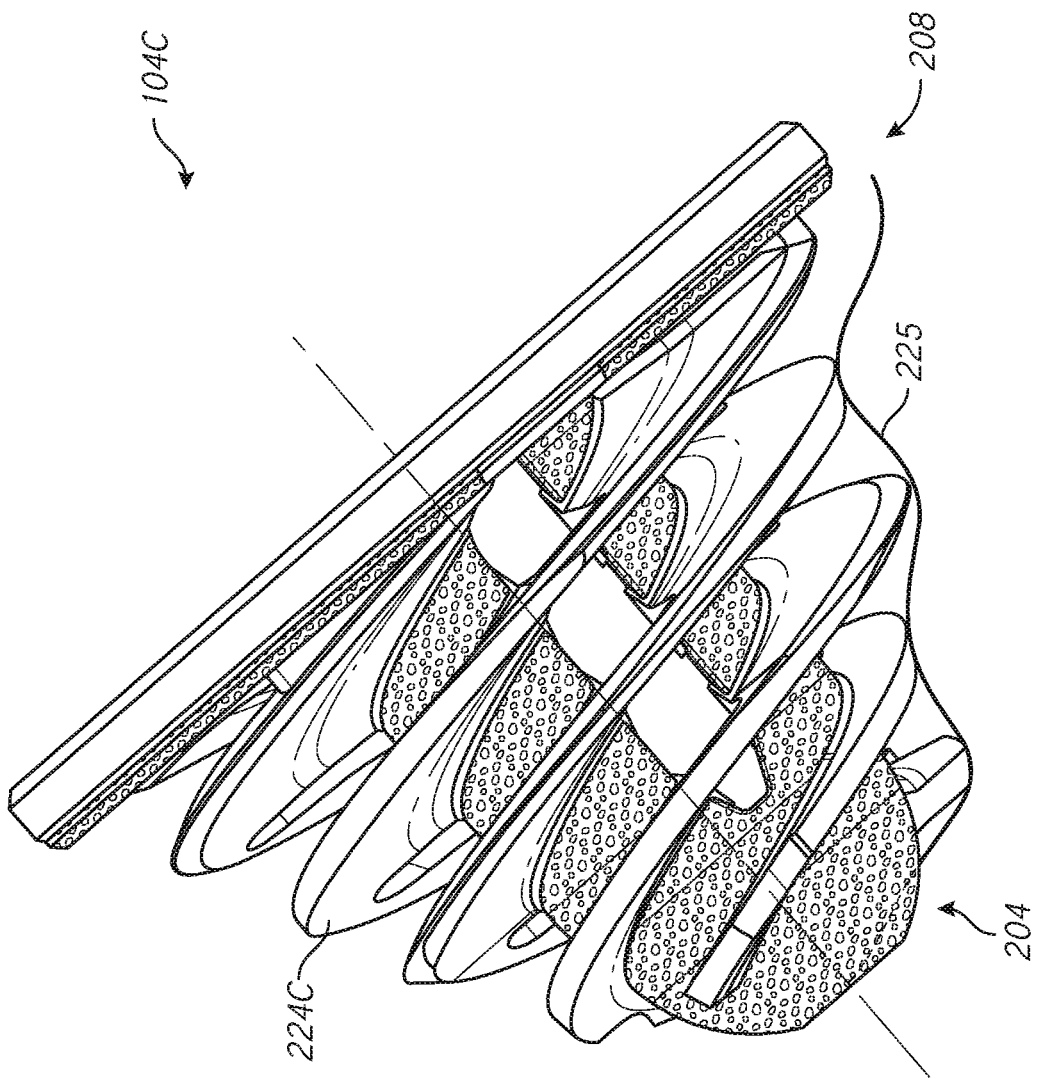
Figure 6B:
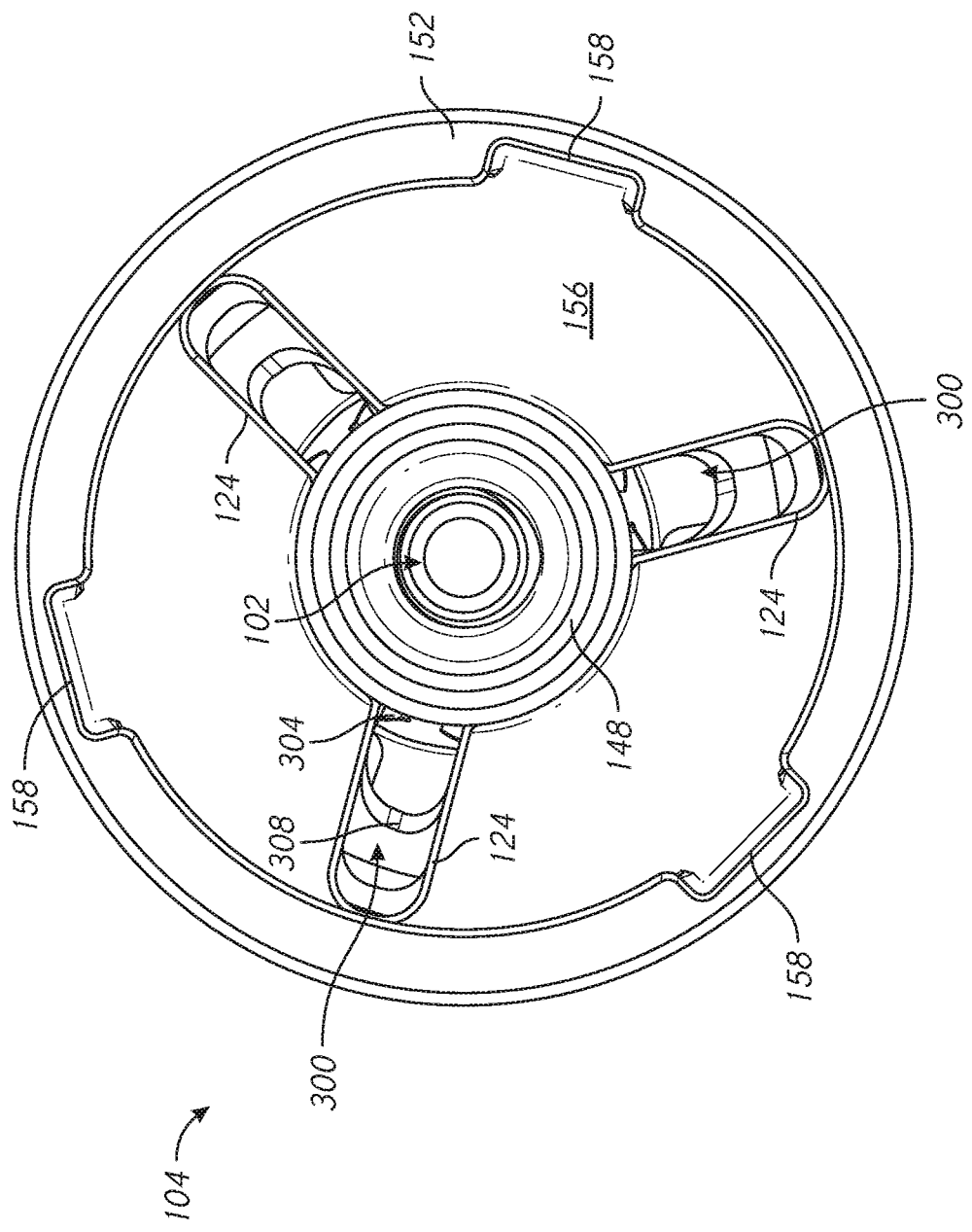
FIG. 6B is a top view of the base member of FIG. 5.

FIGS. 5 and 6B show that the proximal face of the base member 104 can include a raised inner portion 148 and a raised outer portion 152. The outer raised portion 152 extends around an outer periphery 154 of the base member 104. The raised portion 148, 152 are proximally oriented projections relative to a recessed surface 156. The recessed surface 156 can be disposed distally of one or both of the inner portion 148 and the outer portion 152. The raised inner portion 148 can define an aperture for access into the recess 102, which is configured for mating with articular components as discussed below. Each of the raised inner portion and the raised outer portion 148, 152 can comprises annular structures. The recessed surface 156 can comprise an annular portion. The apertures 124 can be formed in the recessed surface 156. In one embodiment the apertures 124 extend radially between the inner raised portion 148 and the outer raised portion 152. The apertures 124 can extend from the inner raised portion 148 to the outer raised portion 152.

The proximal face of the base member 104 also can include a tool interface 158 that enables the base member to be advanced by an inserter into bone, as discussed below in FIG. 17. The tool interface 158 includes three notches in an inward side of the outer raised portion 152. In other embodiments, the tool interface 158 can include apertures in the recessed surface 156, notches in the inner raised portion 148, projections from any surface of the proximal face of the base member 104 or any combination of these features. Also, the tool interface 158 can provide access for a removal tool to engage the locking device 108. As discussed below, the locking device 108 includes a spring arm 168 and a removal tool can be applied at the tool interface 158 to compress the arm 168 to disengage the locking device from the base member 104. In some cases, an inserter tool can engage one or more apertures 124 in the base member 104 upon insertion.

One or more structures for securing the locking device 108 to the base member 104 can be provided as discussed further below. For example the locking device can have an engagement feature 164 disposed on the proximal support 132 that is adapted to engage a corresponding feature on the proximal face of the base member 104. The engagement feature 164 can include an actuatable member that can move into a secure position relative to the recess 140 of the base member 104. As discussed below in connection with FIGS. 8 and 9A, the engagement features 164 can include a spring arm 168 to engage an overhang of the recess 140. As shown in FIG. 5, one embodiment comprises a plurality of actuatable members, e.g., a plurality of spring arms 168. The spring arms 168 can be spaced apart, e.g., providing equal angle separation between adjacent spring arms 168. In one embodiment, the number of spring arms 168 matches the number of arms 110. Each spring arm 168 can be spaced apart from each arm 110 as discussed further below.

In another embodiment, a serration 172 is provided between the arms 110 of the locking device 108 and the base member 104 as discussed in greater detail below in connection with FIG. 9B. The serration 172 is an example of a one-way connection that can be provided between the arms 110 and the base member 104. Other one-way connections can be provided in addition or in place of the serration 172, such as a ratchet, a barb, or one or more spring arms.

Figure 6C:
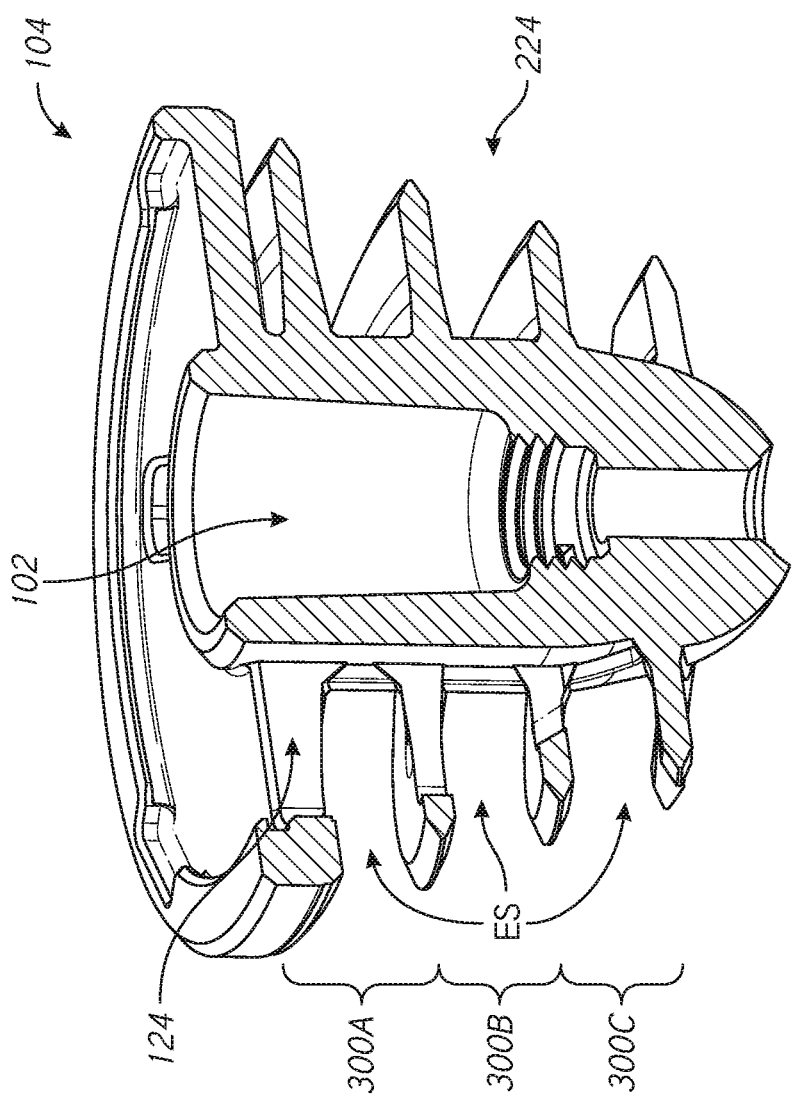
FIG. 6C is a cross-sectional view of the base member of FIG. 5 taken at section plane 6C-6C.
Figure 6D:
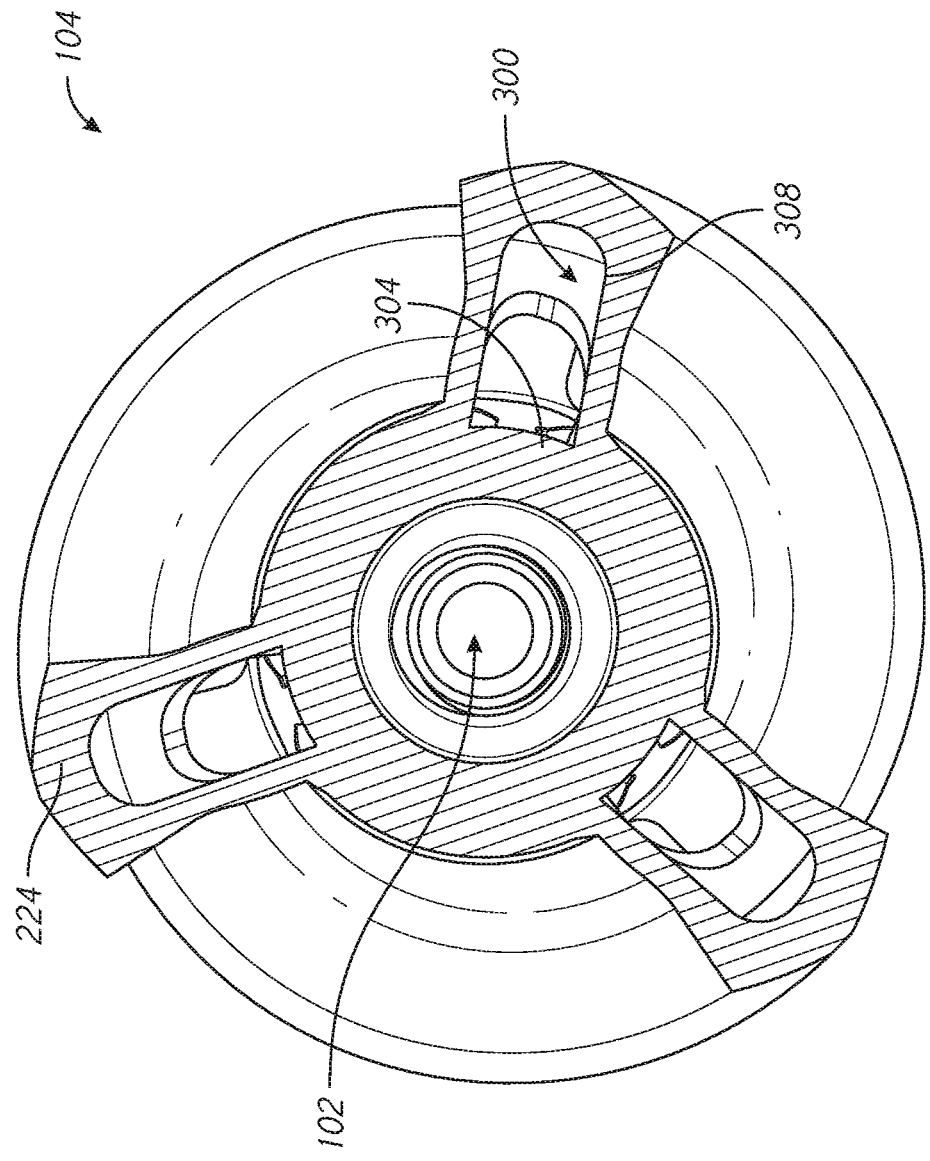
FIG. 6D is a cross-sectional view of the base member of FIG. 5 taken at section plane 6D-6D.

FIGS. 5-6D show further details of embodiments of the base member 104. In some embodiments, the base member 104 can include various features described in PCT publication WO2016/094739, the entirety of which is hereby incorporated by reference herein. The base member 104 has a first end 204, a second end 208 and a body 212 that extends between the first end 204 and the second end 208. The base member 104 can comprise a length L between the first end 204 and the second end 208 that is less than a dimension of an articular surface of typical epiphysis to a medullary canal of a typical humerus. As such, the first end 204 can be disposed within the epiphysis when the second end 208 is at a surface of the bone, as shown in FIG. 10. The second end 208 can be disposed at or on a superior medial resection plane of a humerus while the first end 204 is well within the epiphysis. This enables the first end 204 to stop short of a medullary canal of the humerus when the base 104 is fully implanted, which allows the bone between the first end 204 and the medullary canal to remain unaltered and also simplifies the procedure to the extent that any normal access to and preparation of the medullary canal is not needed. In various embodiments, the length L can be between about 15 mm and about 30 mm, between about 18 mm and about 25 mm, between about 18 mm and about 24 mm, between about 21 mm and about 27 mm, between about 24 mm and about 29 mm. The length L can be about 18 mm, about 21 mm about 23 mm, about 24, mm about 26 mm and about 29 mm. In one approach, at least a portion of the assembly 100 is patient specific. For example, the length L can be defined for a specific patient based on pre-operative planning, such as using two dimensional or three dimensional imaging. The base member 104 can thereafter be manufactured for that patient based on the determined dimension L.

The base member 104 can include a collar 220 and a helical structure 224. The helical structure 224 is disposed about a cylindrical portion 260 of the body 212 of the base member 104. In some embodiments, the helical structure 224 extends directly from the body 212 and may be considered threads of the body 212. The helical structure 224 can include one or a plurality of threads, e.g., two, three, four, or more threads, disposed between the first end 204 and the second end 208. The threads can start adjacent to the first end 204 and extend toward, e.g., entirely to the second end 208. FIG. 6 shows that the threads or other helical structure 224 can end at or adjacent to the collar 220. The threads or other helical structure 224 can have inner portions 240 disposed at or on the body 212 about the recess 102 and outer portions 244 disposed along the periphery of the base 104. FIG. 6 shows that the helical structure 224 has a width defined as the distance between the inner and outer portions 240, 244 that is large, e.g., comprising more than one-quarter of, e.g., about one-third of, the width of the base 104 at a given location. These large threads or other helical structure 224 ensure large purchase in the bone. Large purchase provides strong resistance to pullout even prior to any bone ingrowth into the surfaces of the shoulder assembly 100. Generally one or more surfaces of the shoulder assembly 100 that are in direct contact with bone may be textured e.g., coated or layered with a porous material in order to accelerate tissue ingrowth such as bony ingrowth Therefor good initial resistance to pull-out is advantageous for the patient. At least one turn of a thread or other helical structure 224 completely surrounds the recess 102, e.g., by completely surrounding the body 212, in some embodiments.

FIGS. 6A-1 and 6A-2 show that additional features of the base 104 can be made patient specific. FIG. 6A-1 shows a base 104A with a first end 204, a second end 208 and a body 212 that extends between the first end 204 and the second end 208, similar to the base 104 discussed above. The base 104A has a helical structure 224A that is made patient specific. That is, pre-operative information such as CT scan, MRI scan, X-ray or other assessment of the proximal humerus is conducted. That assessment can reveal patient specific characteristics of the portion of the proximal humerus to which the base 104A will be coupled. For example, that assessment can identify the location of a resection along the humerus H (see FIG. 1) or volume, density, or location of bone between the exposed face F and the medullary canal or the lateral side of the proximal humerus. Based on this information, the configuration of the body 212 can be altered. For instance the helical structure 224A can comprise threads that have a smaller thread pitch than is provided in the threads of the helical structure 224. Smaller thread pitch is suitable for a patient having denser than average bone matter disposed beneath the exposed face F. The thread pitch can be in the range of 3-10 mm depending on the bone quality. A thread pitch of 5 mm could be suitable for average bone density. A thread pitch of 3 mm could be suitable for high bone density. A thread pitch of around 10 mm could be suitable for lower bone density. The helical structure 224A can have a transverse extent (e.g., from the inner portions 240 to the outer portions 244 thereof that is larger than in the helical structure 224. In one form the maximum transverse extent in the helical structure 224A is greater than the maximum transverse extent in the helical structure 224. Larger transverse extent is suitable for a patient having poor bone quality, larger humeral heads, e.g., with larger surface area at the exposed face F and/or with greater volume of bone beneath the exposed face F. For example, the transverse extent could be in a range of between 5 mm and 15 mm depending on the patient. A patient with a smaller humeral head might have a transverse extent of about 5 mm. A patient with a larger humeral head might have a transverse extent of about 15 mm. FIG. 6A-3 shows a base 104C that also can be made for a specific patient based on pre-operative analysis of the patient's bone. A helical structure 224C can be formed or shaped in a patient specific manner. The helical structure 224C can extend from a first end 204 and to a second end 208 of the base 104C. The form of the helical structure 224C can change between the first end 204 and the second end 208. For example, the transverse extend of each successive turn can be selected based upon the patient's bone disposed laterally and inferiorly of the exposed face F to be formed by resection. If the perimeter of the humeral head in planes adjacent and parallel to the exposed face F in the direction of the arrow A in FIG. 1A rapidly reduces a profile 225 can be formed to match that rapid change. If the perimeter of the humeral head in planes parallel to the exposed face F in the direction of the arrow A in FIG. 1A more gradually reduces a profile 225 can be formed to match that more gradual change. Thus, the profile 225 of the helical structure 224C can be made patient specific to enhanced fixation to the bone and/or to avoid over-filling the humeral head with the helical structure.

The body 212 surrounds the recess 102, which is configured to mate with an articular component, such as humeral head or a glenoid sphere. In one embodiment, the body 212 includes a cylindrical portion 260 within which the recess 102 is disposed. The cylindrical portion 260 can have any suitable outside configuration, such as including a textured surface that is well suited to encourage bony ingrowth. The cylindrical portion 260 can include a generally tapered profile in which a portion at or adjacent to the first end 204 of the base member 100 has a first width and a portion at or adjacent to the second end 208 of the base member 100 can have a second width, the second width being greater than the first width. In some embodiments, the cylindrical portion 260 is generally rounded and formed a blunt but tapered profile. The cylindrical portion 260 can have a flat distal surface in some embodiments.

FIG. 10 shows that the cylindrical portion 260 can include a plurality of layers. For example, an inner layer 264 can be disposed adjacent to the recess 102. The inner layer 264 can include the surface surrounding the recess 102 and can extend away from that surface toward an outer surface of the cylindrical portion 260. In one embodiment an outer layer 268 can be disposed adjacent to the outer surface of cylindrical portion 260. The outer layer 268 can extend from the external surface of the cylindrical portion 260 toward the recess 102. In one embodiment, the outer layer 268 is formed directly on the inner layer 264 although other arrangements are possible as well. The outer layer 268 can be a porous structure that is suitable for bony ingrowth.

FIG. 10 also shows that a tool interface 272 can be disposed at or adjacent to the first end 204 of the base member 104. The tool interface 272 can include a threaded portion that can mate with a delivery tool, as discussed further below. A lumen 276 can be provided at the first end 204 such that access can be provided from the first end 204 through the wall of the cylindrical portion 212 into the recess 102. The lumen 276 and recess 102 together provide access for a K-wire or other guiding device such that implanting the base member 104 can be controlled in an appropriate manner.

The collar 220 can be disposed at or can comprise the second end 208 of the base member 104. The collar 220 can have a transverse width, e.g., a diameter that is suitable for a given condition. For example, the diameter of the collar 220 can be selected such that the entire outer periphery of the base 104 is within the bone exposed by resection and/or recessed into such an exposed bone portion, e.g., as illustrated in FIGS. 11-15. In some embodiments the collar 220 has a diameter of more than about 25 mm and less than about 60 mm. The collar 220 can have a diameter of between about 30 mm and about 45 mm. The collar 220 can have a diameter of about 33 mm in one embodiment. The collar 220 can have a diameter of about 42 mm in one embodiment. Making the collar 220 as large as possible within such bounds provides for better load transfer between the collar 220 and the humerus H. In one approach, the diameter of the collar 220 can be defined for a specific patient based on pre-operative planning, such as using two dimensional or three dimensional imaging. The base member 104 can thereafter be manufactured for that patient based on the determined diameter of the collar. For example, the diameter of the collar 220 can be selected such that the collar covers the cortical rim exposed by resection. The collar 220 can attach to or can be integrally formed with the cylindrical portion 260 of the body 212. In one embodiment the collar 220 comprises a transverse flange 290 that extends outward of the recess 102 that is also disposed at the second end 208. An inner portion of the flange 290 can be disposed adjacent to the recess 102 and can include the inner raised portion 148. An outer portion of the flange 290 can be disposed outward of the inner portion. The flange 290 can define the proximal face of the base member 104. The flange 290 can accommodate the proximal support 132 of the locking device 108. FIG. 9A shows that in some embodiments, the flange 290 can at least partially surround a space 294 disposed therein to receive a portion of the locking device 108. The space 294 can be an annular recess located proximal of the recessed surface 156 and between the inner portion 148 and the outer portion. The space 294 can be bounded by an inner edge of the outer portion 152 and an outer edge of the inner portion 148. The flange 290 can engage the spring arm 168 of the locking device 108 in the space 294 such that the locking device 108 will not be inadvertently disengaged from the base 104 and protrude from or be removed from the space 294.

FIGS. 5 and 10 show that in some embodiment, the shoulder assembly 100 includes a pathway 300 that projects distally of the collar 220. The pathway 300 can comprise a first pathway. The shoulder assembly 100 can include a plurality of pathways, 300 with each pathway corresponding to an arm 110 of the locking device 108. FIG. 6B shows that the base 104 can define a plurality of such pathways, e.g., two or three pathways configured to receive corresponding arms 110. There can be four or more than four pathways 300. The pathway 300 can have a first end located at the opening or apertures 124 in the collar 220. The pathway 300 can continue down through the base member 104. FIG. 6C shows that the pathway 300 can have one or more segments disposed through the helical structure 224. A first segment 300A of the pathway 300 extends from the aperture 124 to a first portion, e.g., a proximal-most turn or portion of the helical structure 224 immediately distal of the collar 220, e.g., immediately distal of one of the apertures 124. A second segment 300B of the pathway 300 extends from the first segment 300A to a second turn or portion of helical structure 224 immediately distal of the first portion of the helical structure. A third segment 300C of the pathway 300 can extend from the second segment to a third turn or portion of helical structure 224 immediately distal of the second portion of the helical structure 224.

FIGS. 6B and 6D illustrate that at specific locations along the length of the base 104 from the first end 204 to the second end 208, the pathway 300 can have a first boundary 304 corresponding to an outer surface or layer of the cylindrical portion 260, for example corresponding to a surface of the outer layer 268. The pathway 300 can have a second boundary 308 at a same location along the length of the base 104 from the first end 204 to the second end 208 formed by an adjacent portion of helical structure 224. The second boundary 308 can include a U-shaped opening in the inner portion 240 of the helical structure 224. The U-shaped opening in the inner portion 240 can extend across the width of the helical structure toward the outer portion 244 of the helical structure 224. The U-shaped opening can extend 25%, 35%, 45%, 50%, 60%, 70%, 75% or up to 90% of the distance across the width of the helical structure 224 from the inner portion 240 toward the outer portion 244. In one embodiment, the helical structure 224 has a tapered configuration in which transverse distance between opposite sides of the helical structure 224 is decreased in the direction of the first end 204 compared to the same dimension toward the second end 208. The length of the U-shaped opening in successive portions of the helical structure 224 in the direction toward the first end 204 is progressively less in some embodiments. As a result the width bounded by a turn of the helical structure 224 and the cylindrical portion 260 in the first segment 300A of the pathway 300 can be greater than the width bounded by a turn of the helical structure 224 and the cylindrical portion 260 in the second segment 300B. The width in the second segment 300B can be greater than the width in the third segment 300C bounded by a turn of the helical structure 224 and the cylindrical portion 260. This configuration is advantageous in accommodating embodiments of the locking device 108 having arms 110 that are tapered as discussed further below.

The pathway 300 can extend through one or more spaces between adjacent threads of the helical structure 224. The pathway 300 can comprise two or more segments surrounded by portions of the base member 104 and at least one exposed segment ES. The exposed segments comprise portions of the first and second segments 300A, 300B and between the second and third segments 300B, 300C in some embodiment. The exposed segments ES are exposed in that, unlike the segments 300A, 300B, 300C, the exposed segments of the pathway 300 are not enclosed circumferentially and thus bone disposed within the helical portion 224 can directly contact the arms 110 in the exposed segment. As such the pathway 300 is bounded by bone matter in the exposed segments.

Figure 7:
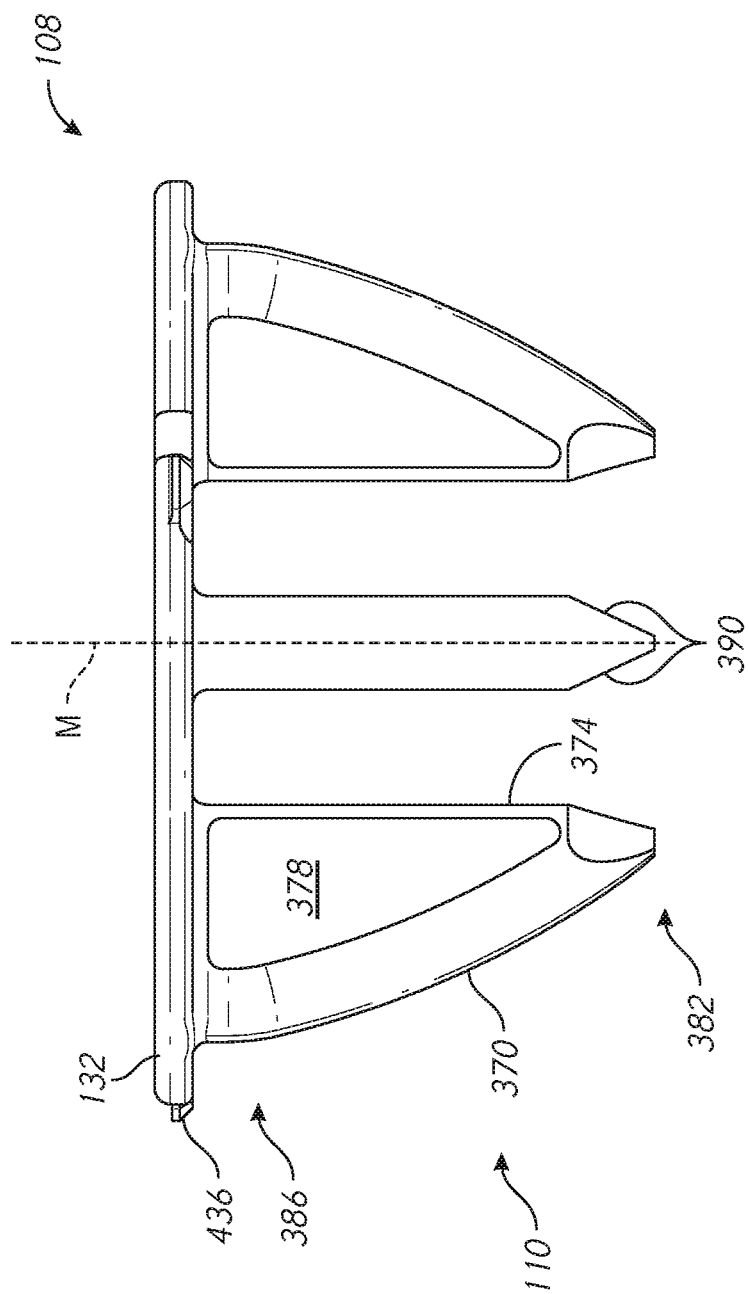
FIG. 7 is a side view of one embodiment of a locking component, which is a component configured to control, e.g., reduce or eliminate and/or control rotation of a base member or of a helical structure of a prosthesis assembly.
Figure 8:
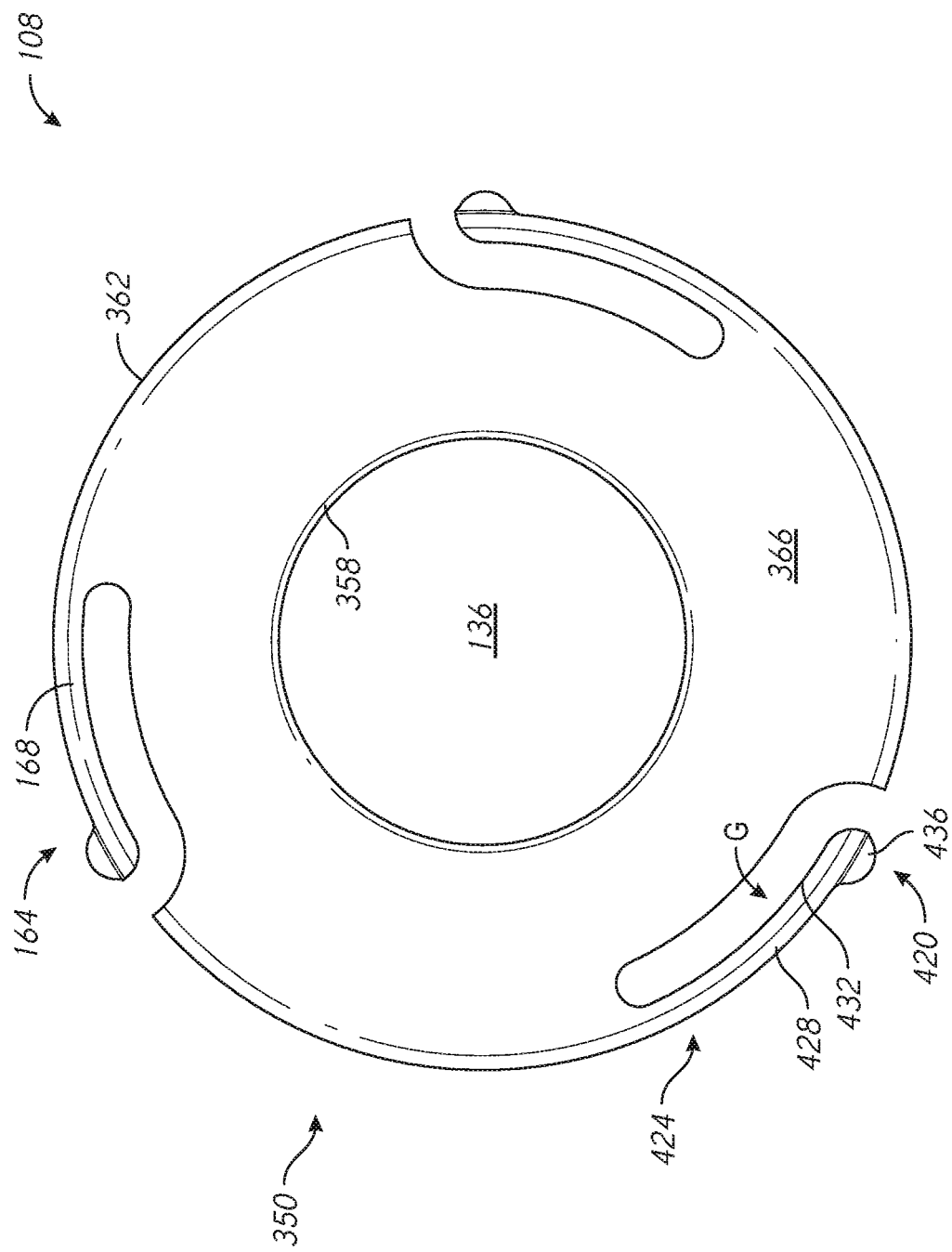
FIG. 8 is a top, proximal side, or medial side view of the locking component of the FIG. 7.

FIGS. 5, 7 and 8 show the locking device 108 in detail. As discussed above, the locking device 108 has a proximal support 132 and a first arm 110 that projects distally of the proximal support 132. The proximal support 132 includes an inner periphery 358, an outer periphery 362 and an annular member 366 disposed therebetween. The inner periphery 358 surrounds the central opening 136, which is sized to receive the inner raised portion 148 of the base member 104 if present. The annular member 366 is configured to be received in the recess 140, as discussed above.

The first arm 110 is configured to be disposed in the first pathway 300. The pathway 300 projects distally of the collar 220. The first arm 110 is disposed distal of the collar 220 when the proximal support 132 is disposed adjacent to a proximal side of the collar 220 and the first arm 110 is in the first pathway 300.

The first arm 110 includes an outer edge 370, an inner edge 374 and a span 378 disposed therebetween. The first arm 110 includes a first end 382 disposed away from the support 132 and a second end 386 disposed adjacent to and in some cases directly coupled to the support 132. The first arm 110 can be tapered, for example with the outer edge 370 approaching the inner edge 374 in the direction toward the first end 382 and/or with the outer edge 370 diverging away from the inner edge 374 in the direction toward the second end 386. In one embodiment, opposite faces 390 of the span 378 are also tapered with at least one of, e.g., both of, the opposite faces 390 approaching a longitudinal mid-plane M of an arm 110. The tapering of the arms between the edges 370, 374 facilitates providing a tapered profile in the base member 104. The tapering of the arms between the edges 370, 374, sometimes referred to herein as a radial taper, facilitates insertion of the first end 382 into the aperture 124 because the first end 382 is much narrower in the dimension between the edges 370, 374 than the aperture 124 is in the radial direction. The tapering of the arms 110 between the faces 390, sometimes referred to herein as a circumferential taper, facilitates insertion of the first end 382 into the aperture 124 because the first end 382 is much narrower in the dimension between the faces 390 than the aperture 124 is in the circumferential direction.

At least one of the circumferential and radial tapers of the arms 110 enables the locking device 108 to easily be advanced through bone matter that is disposed along the pathway 300.

As discussed above, the first arm 110 is disposed through bone in the space between successive portions of the helical structure 224, e.g., in the first segment of the path 300 and in the second segment of the path 300, when the humeral shoulder assembly is implanted. The span 378 and/or other parts of the arms 110 can be porous to enhance bony ingrown when the assembly 100 is implanted. The porous properties can be provided by a porous metal surface or structure or by other porous layers disposed on an underlying layer of metal or another material. At least the widening of the arms 110 toward the second end 386 increases the purchase of bone in the widened area, e.g., in the first segment of the path 300 and also in the second segment of the path 300 compared to an arm that is not tapered.

In some embodiments, the arms 110 are not tapered in the radial direction. For example the arms 110 can have a constant radial dimension between the edges 370 and 374 at a length between, e.g., along the entire length between, the first end 382 and the second end 386. In some embodiments, the arms 110 are not tapered in the circumferential direction. For example the arms 110 can have a constant circumferential dimension between the first end 382 and the second end 386.

As discussed above, the locking device 108 facilitates retaining the base member 104 in the bone at least by opposing, and in some cases completely preventing, rotation of the base member that would cause the base member to back out of the bone into which it has been advanced. Additionally, in some embodiments, it is beneficial to oppose, and in some cases completely prevent, axial movement of the locking device 108 away from the base member 104. At the extreme, such movement could result in the arms 110 of the locking device 108 completely coming out of the pathways 300 and, indeed, out of the base member 104 completely. It also may be desirable to prevent even lesser movements of the locking device 108 relative to the base member 104. As shown in FIG. 9A, a distal face 402 of the annular member 366 may be positioned in direct contact with a proximal face 404 of the transverse flange 290. Such contact can correspond to a proximal face 406 of the annular member 366 being distal of a proximal face 408 of the raised outer portion 152. By recessing the annular member 366, the interaction of the assembly 100 with the articular member of the kit 84 of FIG. 4 is controlled. For example, the annular member 366 will not impede advancement of the articular members into secure engagement with the recess 102.

FIGS. 8 and 9A illustrate various embodiments of axial locking configuration that can be provided in the shoulder assembly 100. An axial locking configuration can include the engagement feature 164 disposed on the proximal support 132. The spring arm 168 of the engagement feature can include a first end 420 disposed away from the annular member 366 and a second end 424 coupled with the annular member 366. The spring arm 168 also has an elongate portion 428 that extends between the first end 420 and the second end 424. The elongate portion 428 preferably has an arcuate form and can, in some embodiments, have the same curvature as a portion of the annular member 366 adjacent to the second end 424. The elongate portion 428 can be separated from the annular member 366 along a radially inner edge 432 of the elongate portion 428 by a gap G. The gap G and the length of the elongate portion 428 can be such that the first end 420 can be moved sufficiently to allow for a snap-fit connection as discussed further below. In one embodiment, the first end 420 of the spring arm 168 has a deflector 436 that facilitates movement of the elongate portion 428 and specifically movement of the first end 420. FIG. 9A shows that the deflector 436 can include an angled surface 460 that initially engages a corresponding angled surface 464 on the base member 104, e.g., on the raised outer portion 152 at the proximal face of the base member. As the arms 110 of the locking device 108 are advanced into the paths 300, the annular member 366 eventually is received in the space 294. At that time, the angled surfaces 460, 464 engage each other, which engagement causes the deflection of the first end 420 of the spring arm 168. The first end 420 is deflected radially inwardly such that the gap G is reduced at least at the first end 420. This allows a proximal facing surface 472 to move to a position distal of a distal facing surface 476. After the proximal facing surface 472 is at a position distal of the distal facing surface 476, the spring arm 168 resiliently moves the deflector 436 back to the configuration shown in FIG. 8. At this point, the proximal facing surface 472 is distal of and aligned with, e.g., positioned under, the distal facing surface 476, as shown in FIG. 9A. In this configuration, the proximal facing surface 472 blocks the distal facing surface 476 from moving proximally. Thus the surfaces 472, 476 prevent the locking device 108 from disengaging from the base member 104.

Another advantageous aspect of the assembly 100 is that the locking device 108 can be quickly and easily disengaged from the base 104. The tooling interface 158 allows an extraction tool to be disposed between the raised outer portion 152 and the spring arm 168. The extraction tool can apply a radially inward force on an outer periphery of the elongate portion 428 of the spring arm 168. Compression of the spring arm 168 decreases the gap G as the proximal facing surface 472 is moved radially inward of the distal facing surface 476. Once the first end 420 is entirely radially inward of the distal facing surface 476, the engagement feature 164 is disengaged from the base 104. If more than one spring arm 168 is provided some or all of the spring arms can be compressed to allow the locking device 108 to be withdrawn from the base 104.

FIG. 9B shows additional axial locking configurations that can be provided in the shoulder assembly 100. In these embodiments, axial locking can occur at an interface 490 between one or more of the arms 110 and one or more of the pathways 300. For example, the serrations 172 discussed above can be provided at the interface. In one variation, serrations 172 are disposed along the pathway, e.g., on a surface of the cylindrical member 212 and/or on a surface of the helical structure 224. The serrations 172 can be placed at both the surface of the cylindrical member 212 and at the helical structure 224. In another embodiment, the serrations 172 could be provided on a surface of the arm 110, e.g., on one of the outer edge 370, the inner edge 374, and/or on one of the faces 390. The serrations 172 allow for relatively easy insertion of the arms 110 but bite into and oppose withdrawal of the locking device 108 to oppose axial disengagement of the locking device 108 from the base member 104.

The serrations 172 can be disposed along the entire length of the interface between the arms 110 and the base member 104 or just at a position where the base member 104 and the locking device 108 are fully engaged.

V. Method of Application to an End Portion of a Long Bone

FIGS. 11-19 illustrate various techniques for implanting the shoulder assembly 100 in a humerus H. The method illustrates placement in a proximal end of the humerus H, e.g., in the humeral head h.

FIG. 11 illustrates an early step of one embodiment of a method including resecting the head h of the humerus H. Prior to resecting the head h of the humerus H a guide 600 is applied to the humerus H. The guide 600 includes structure for mating with the humerus H and the head h, for example, a plate 604 to mate with the humerus H and pins 608 to mate with the head h. The guide 600 also has a slot 612 to guide a saw to cut the humerus H to expose cancellous bone of the head h. FIG. 12 shows that after resecting the head h of the humerus H the size of the head is evaluated with a template 620. To obtain a quick and accurate sizing, a guide pin 624 is first placed in the resected head h. The template 620 is advanced over the guide pin 624 into contact with the resected head. The size of the resected head h is determined from the template 620. The guide 600 can be a reusable guide that is not specific to any particular patients. In other embodiments, the guide 600 is formed with reference to a specific patient. That is, the guide 600 can be formed to mate with the patient, such as by conforming in whole in part on a bone facing side to the shape of the bone as observed or measured using imaging or other devices prior to surgery.

Figure 11A:
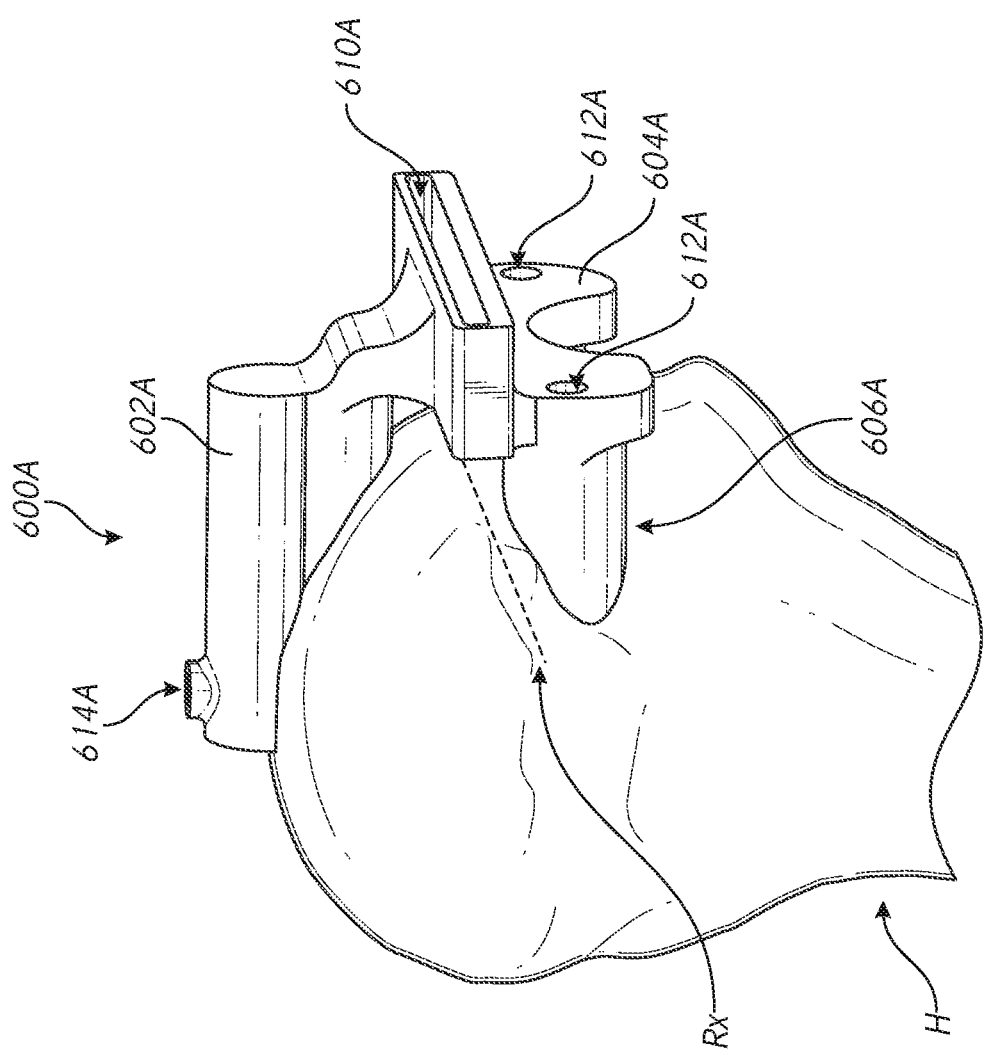
Figure 12:
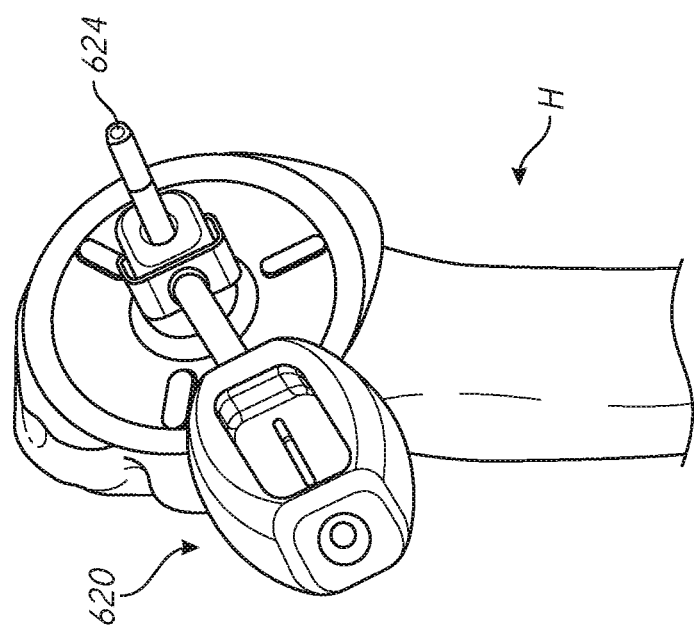

FIGS. 11A-11B show that in some cases, a resection surface RX can be formed in a patient specific manner using a patient specific humeral cutting guide 600A. The humeral cutting guide 600A includes a first portion 602A, a second portion 604A, and a third portion 606A. One or more, e.g., all, of the first portion 602A, the second portion 604A, and the third portion 606A can be configured to contact specific parts of the humerus H. For example, each of these portions can have a substantial negative surface 608A. The surfaces 608A can be formed with reference to a pre-operative imaging of the patient's humerus, e.g., using CT scans, MRI, or X-ray information. The surfaces 608A can be configured such that the cutting guide 608A fits only in a specific location and orientation on the humerus H. The guide 600A also includes a cutting plane 610A. The cutting plane 610A is disposed at a specific location and orientation such that the resection Rx of the humerus H is at a pre-planned location and orientation. The resection Rx when formed using the cutting plane 610A will have a pre-planned peripheral shape. The pre-planned shape of the periphery of the resection Rx can be accounted for in forming portions of humeral assemblies and implants that engage the resection Rx. The guide 600A can have one or a plurality of apertures 612A to secure the guide 600A to the humerus H. The guide can have one or a plurality of apertures 614A that can be used to place guide pins or other members to facilitate one or more subsequent steps of preparing the humerus H or implanting components.

Figure 13:
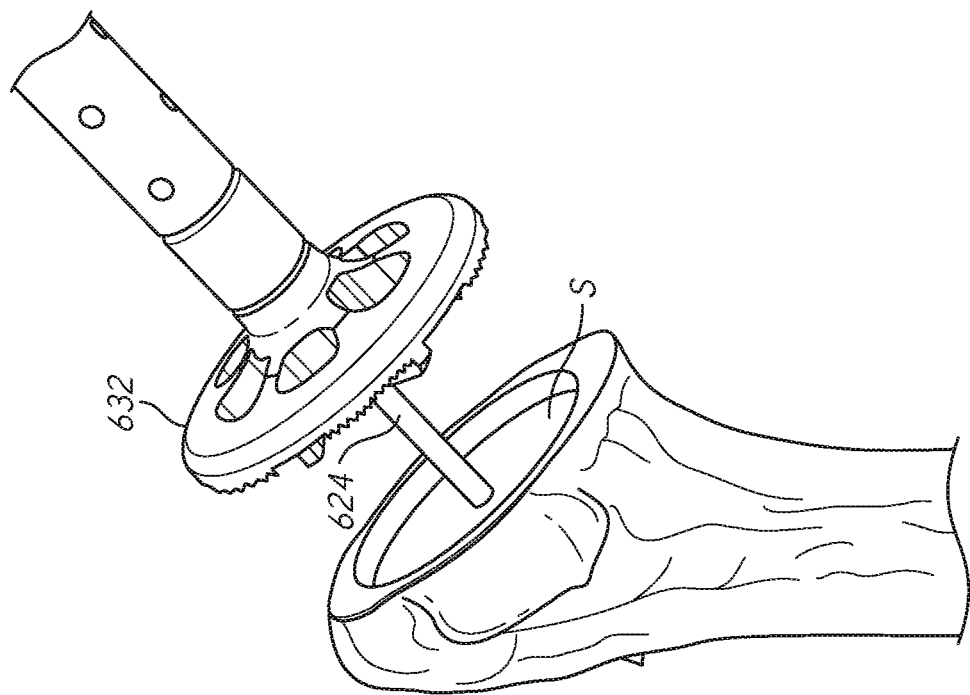

FIG. 13 shows that the resected surface of the head h can be prepared, such as by using a planar or a reamer 632. The reamer 632 also can be guided by the guide pin 624. The reamer 632 can be used to form a recessed surface S to which the assembly 100 will be applied after further preparation.

FIG. 14 shows a step of measuring depth of the recessed surface S. The purpose of this step is to provide a secondary confirmation that the assembly 100 will fit into the metaphysis without striking the lateral cortex. While the analysis of FIG. 12 indicates a diameter of base member 104 that could be used, the depth gauge 637 of FIG. 14 provides a depth sizing that confirms a maximum length, e.g., depth, that would fit in the recessed surface S surgeon is instructed to take the smaller of the two sizes determined.

Figure 16:
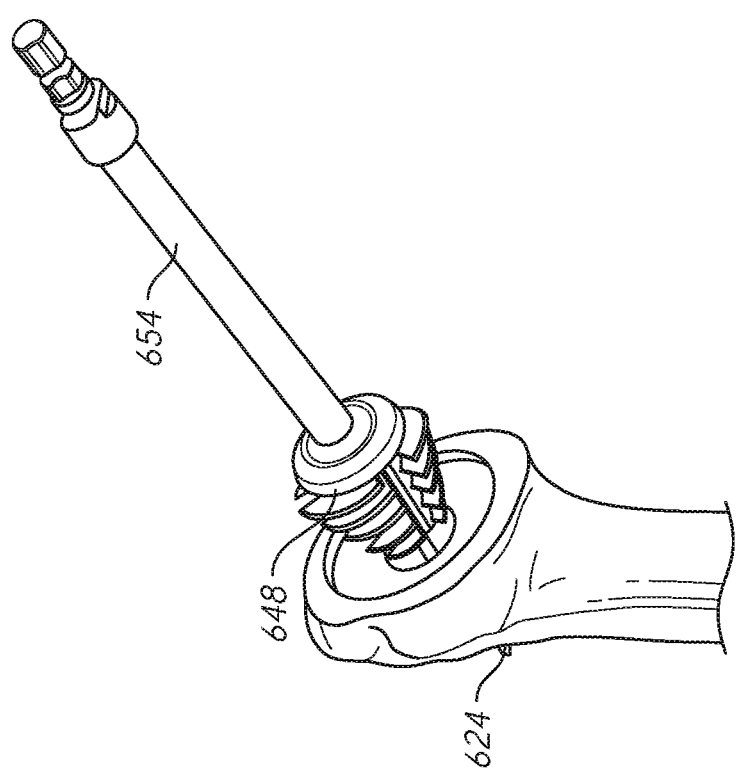

FIG. 15 illustrates that following depth measurement, a bore B is formed in the surface S in initial preparation of the surface S to receive the shoulder assembly 100. The bore B is formed using a drill 640. The drill 640 can be a convention cannulated design configured to be advanced over the guide pin 624. The drill 640 can be configured as a universal drill with a modular stop to obtain variable lengths. The drill 640 can be one of a plurality of drills, each drill of the plurality having a different size as appropriate. In certain methods, the process of forming the bore B and reaming the surface S as discussed above in connection with FIG. 13 can be combined. For example, a drill 640 can have a reaming feature disposed proximally of the bore forming features such that a continuous motion toward the surface formed using the guide 600 can initially form the bore B and subsequently form the surface S. Once the bore B is formed the humerus H may be prepared to receive the press-fit embodiments disclosed herein, e.g., in FIGS. 2-3. FIG. 16 shows that once the bore B has been formed, the bore B can optionally be tapped to be prepared to receive the base member 104 of the shoulder assembly 100. The tapping process can be achieved by using a helical tap component 648 that is advanced over the guide pin 624. The helical tap 648 can follow the form of the helical structure 224 of the base member 104 such that the base member 104 can be easily advanced into the bore. The helical tap 648 can be secured to a shaft 654 that can be mounted to a motor driven drill or to a hand tool.

Figure 17:
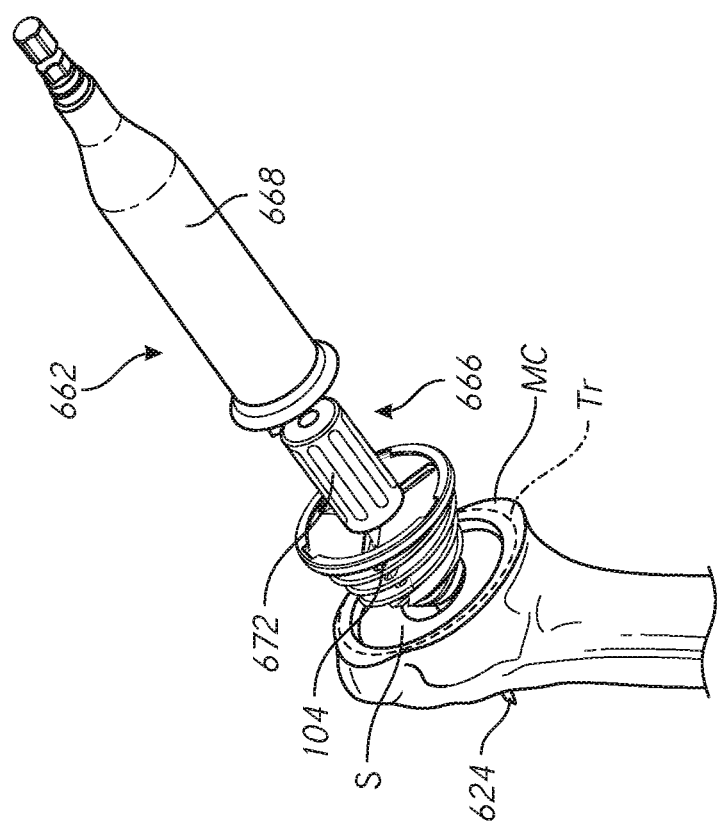

FIG. 17 shows that in some embodiments discussed herein a trunnion or other transverse extender can be coupled with the face F of the humerus H at the resection plane. The trunnion is illustrated by a dashed line labeled Tr. The trunnion can be applied after the bore B and/or the recessed surface S is or are formed and, optionally, after the tapping process. The trunnion can be applied by gentle pressure laterally against the face F or against the face F and the recessed surface S by hand or using a dedicated tool. The trunnion can be placed prior to inserting the base member 104 (or any of the other base members disclosed herein that can be mated to the trunnion).

FIG. 17 shows a step of inserting the base member 104. The base member 104 is secured to a distal end of an inerter 662. The inserter 662 has a stem 666 that is threaded at a distal end thereof. The threads of the stem 666 can be mated with the tool interface 272 (see FIG. 10), e.g., with threads of the tool interface. Preferably the stem 666 is enlarged at a mid-section thereof providing at least a shoulder that can mate with the inner raised portion 148 of the base member 104. A separate member 668 of the inserter 662 is advanced over the stem 666 to the tool interface 158, and the force of advancing the base member 104 thus can be applied through the tool interface 272, through the inner raised portion 148, through the apertures 124 or through more than one of these (or other) features of the base member 104. Splines 672 provide for good grip by the surgeon so that the surgeon can easily engage the stem 666 to the tool interface 272. In another variation, a driver with a torqueing device at a proximal end couples at its distal end directly with the tool interface 272, through the inner raised portion 148, through the apertures 124 or through more than one of these (or other) features of the base member 104 to enable more direct transfer of torque to the base member. Preferably inserting the base member 104 into the bone includes placing the outer periphery 154 in the recessed surface S, e.g., at least partially recessed into the resected bone of the humerus H. The dashed line Tr shows the outer periphery of a trunnion that can optionally be placed between the face F and the base member 104 (or other base members described herein). The line Tr shows that the trunnion where provided cover all or substantially all of the face F between the base 104 and the perimeter RP of the humerus H.

Figure 18:
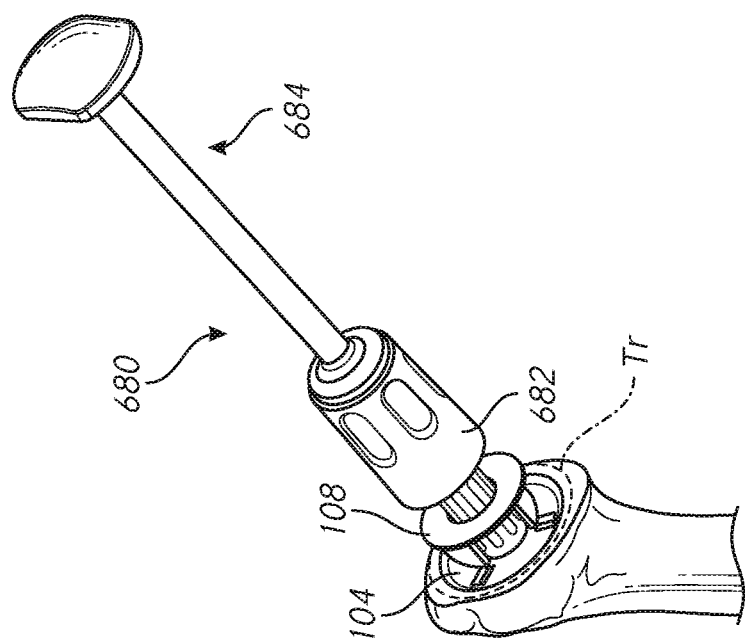
Figure 20:
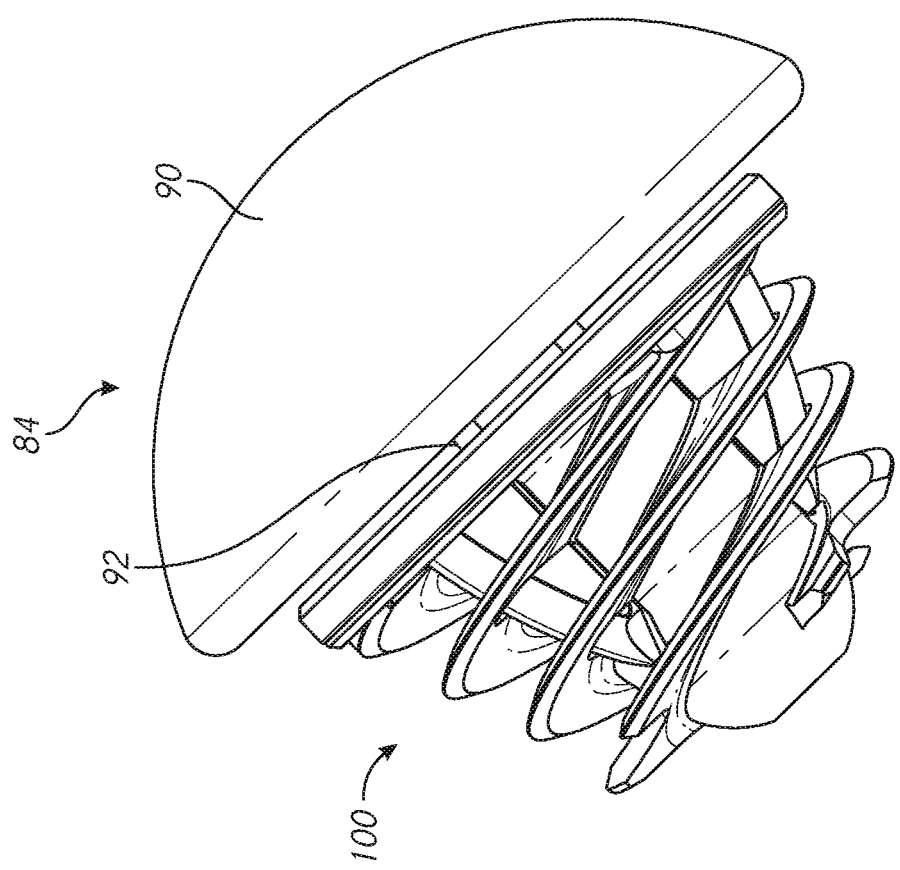
FIG. 20 is a side view of the stemless shoulder assembly of FIG. 5 coupled with an anatomic articular component of the kit illustrated in FIG. 4.

FIG. 18 shows that after the base member 104 has been inserted, the locking device 108 can be inserted. The base member 104 is inserted by a rotation of the member by rotation of the inserter which is directly connected to the base member as discussed above in connection with FIG. 17. The locking device 108 is inserted along the pathway by linear translation, e.g., by a movement along a generally straight axis without rotation. An inserter 680 is provided that has an enlarged head 682 that can be secured to or can just rest upon the proximal face of the annular member 366 of the proximal support 132. The head 682 is then advanced over the splines 672 of the stem 666, with the stem 666 acting as an axial guide. In order to implant the locking device 108 the first end 382 of the arm 110 or arms is aligned with the aperture 124 or apertures if more than one. The arms 110 are radially and circumferentially tapered and the apertures 124 are sized for the wider proximal end of the arms. This configuration helps guide the locking device 108 into the base member 104. The proximal end 684 of the inserter 680 in configured for impacting the locking device 108 into the base member 104. Once the locking device 108 is in place the base member 104 is fixed and will not back-out by subsequent rotation. The locking device 108 assures that the level of compression by the trunnion or by an enlarged flange, transverse plate or collar configured to reduce stress shielding initially provided by full advancement of the base 104 against the trunnion, flange, transverse plate or collar will be maintained such that stress shielding will be reduced, minimized, or eliminated.

Figure 19:
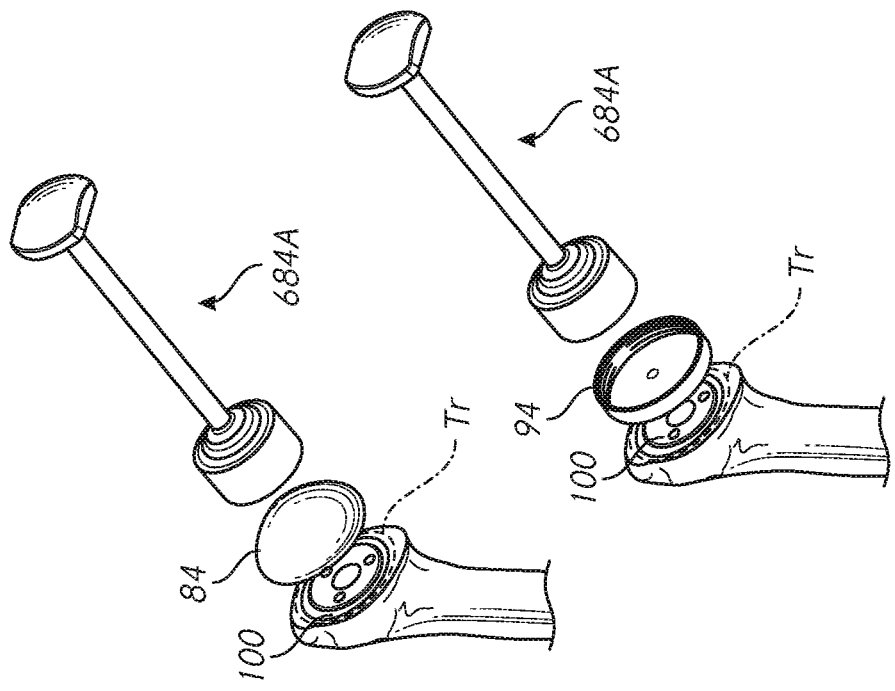
Figure 21A:
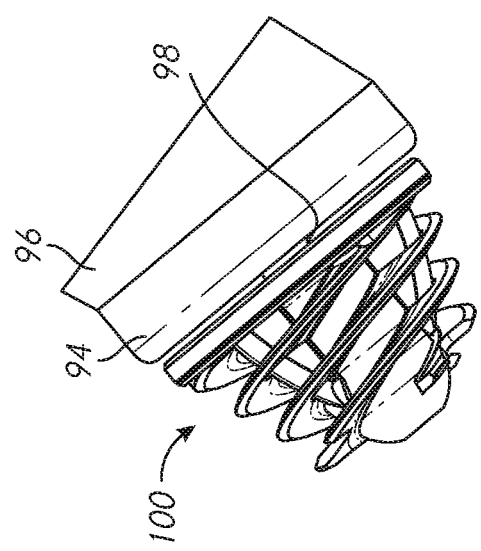
FIG. 21A is a side view of the stemless shoulder assembly of FIG. 5 coupled with a reverse articular component of the kit illustrated in FIG. 4.

FIG. 19 shows later steps of a method of implanting an anatomic shoulder prosthesis. After the base member 104 and the locking device 108 are placed, an anatomic articular component 86 can be coupled with the recess 102. The anatomic articular component 86 comprises a convex surface 90, analogous to the natural anatomy. The anatomic articular component 86 is placed with an impactor 684A. Although shown as a separate, dedicated device the insertion and impaction functions illustrated in FIGS. 18 and 19 could be carried out by the same device. For example a contoured face to contact the surface 84 could have a portion configured for inserting the locking device 108 and/or the tray 94. FIG. 19 shows an alternative step of a method of implanting a reverse shoulder prosthesis. After the base member 104 and the locking device 108 are placed, a reverse articular component 88 can be coupled with the recess 102. In one form, the reverse articular component 88 includes a tray 94. The tray 94 can be coupled with an articular component 96 comprising a concave surface for articulating with a glenoid sphere disposed on a glenoid of a scapula (discussed further below). The tray 94 is placed with an impactor 684A. The reverse shoulder prosthesis including the shoulder assembly 100, the tray 94 and the articular component 96 is shown in FIGS. 21A and 21B. A glenoid sphere 99 mated with a glenoid is shown in FIG. 21B. The shoulder joint provides movement of the patient's arm by articulating the component 96 over the glenoid sphere 99.

As discussed above, a trunnion illustrated by the line Tr can be provided between the appropriate articular component placed in the steps illustrated in FIGS. 18 and 19 to cover a portion of the resection Rx that is outlying relative to an outer periphery of the base 104 of the assembly 100. The trunnion shown in dashed line Tr to indicate that the trunnion Tr is optional. The trunnion can be made patient specific in various ways discussed further herein. The trunnion can be placed in compression against the resection Rx and can cover some or all of the portion of the resection Rx subject to erosion arising from stress shielding. For example, the trunnion can be configured for the specific patient to extend medially and inferiorly to cover a reduce, minimize or eliminate stress shielding, e.g., of the medial calcar MC, as discussed above.

In one variation of these methods, assemblies, and kits the locking device 108 is inserted at the same time as some or all of the reverse articular component 88 or at the same time as the anatomic articular component 86. The locking device 108 can be a separate component that is loaded onto an inserter or impacting tool that can be previously loaded with the reverse articular component 88 or the anatomic articular component 86. The locking device 108 can be a separate component that is loaded onto an inserter or impactor with, but relatively moveable to, the reverse articular component 88 or the anatomic articular component 86. The locking device 108 and the reverse articular component 88 can be formed as a monolithic structure that can be loaded together onto an inerter. The locking device 108 and the anatomic articular component 86 can be formed as a monolithic structure that can be loaded together onto an inerter.

VI. Additional Apparatuses and Methods

The foregoing embodiments, whether generic or patient specific, can be applied to bones other than the humerus. For example, the concepts can be applied to a glenoid implant and to other joint applications.

A. Glenoid Anchors and Methods

FIGS. 22-26 illustrate a shoulder assembly 800 that is adapted for securement to a glenoid. The shoulder assembly 800 is similar to the shoulder assembly 100 described above, except as described differently below. Any feature discussed above can be substituted in and supplement the features of the shoulder assembly 800. The features of the shoulder assembly 800 can be substituted in and supplement the features of the shoulder assembly 100.

Figure 22:
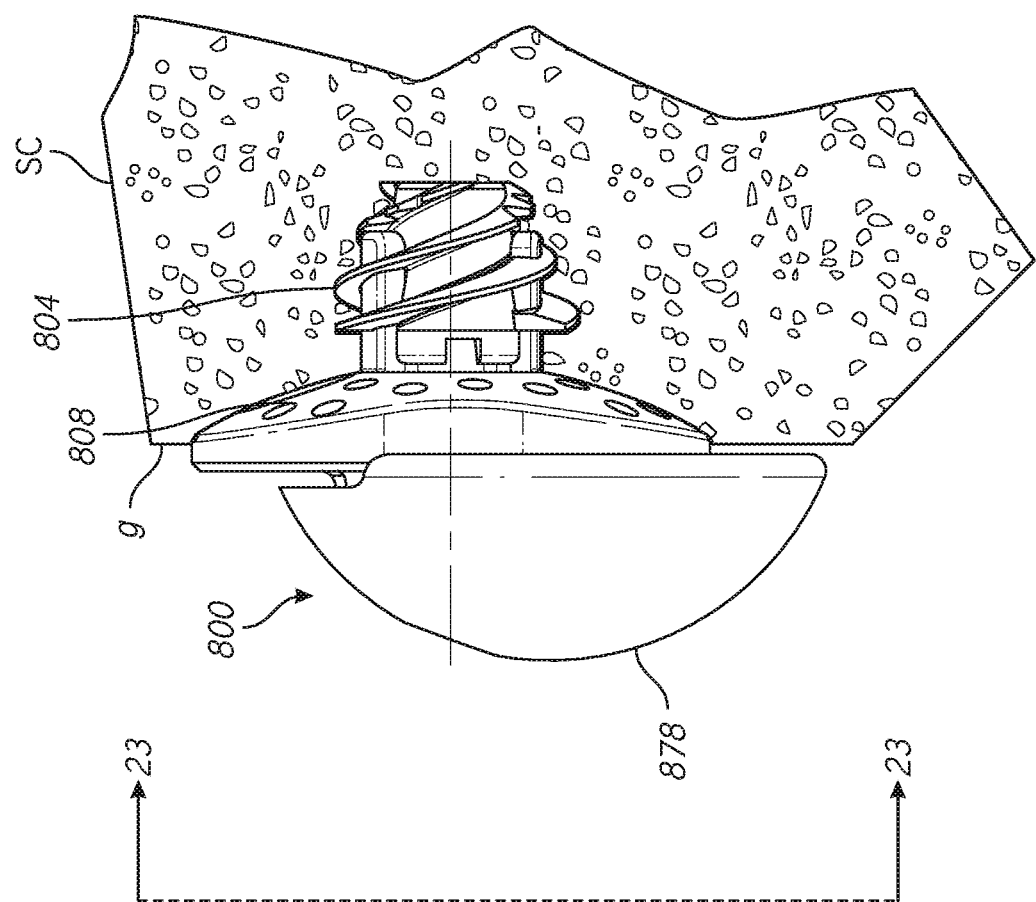
FIG. 22 is a schematic side view of a glenoid of a scapula of a shoulder of a patient with a reverse shoulder prosthesis assembly disposed therein.

FIG. 22 shows that the shoulder assembly 800 can be implanted into a glenoid region g of a scapula SC. The shoulder assembly 800 includes a base member 804 and a plate member 808. The base member 804 has a medial end 816 and a lateral end 820. FIGS. 24-26 show that the base member 804 includes a body 812 that extends between the medial end 816 and the lateral end 820. A lumen 822 extends in the body 812 from the lateral end 820 toward and in some cases entirely to the medial end 816. A distal portion of the lumen 822 includes a threaded zone 823, discussed below. The base member 804 includes a helical structure 824, which is disposed along the body 812 between the medial and lateral ends 816, 820, respectively. The helical structure 824 extends from the medial end 816 to the lateral end 820 in some embodiments. In some embodiments a tool interface 826 is disposed lateral of a lateral end of the helical structure 824.

Figure 26A:
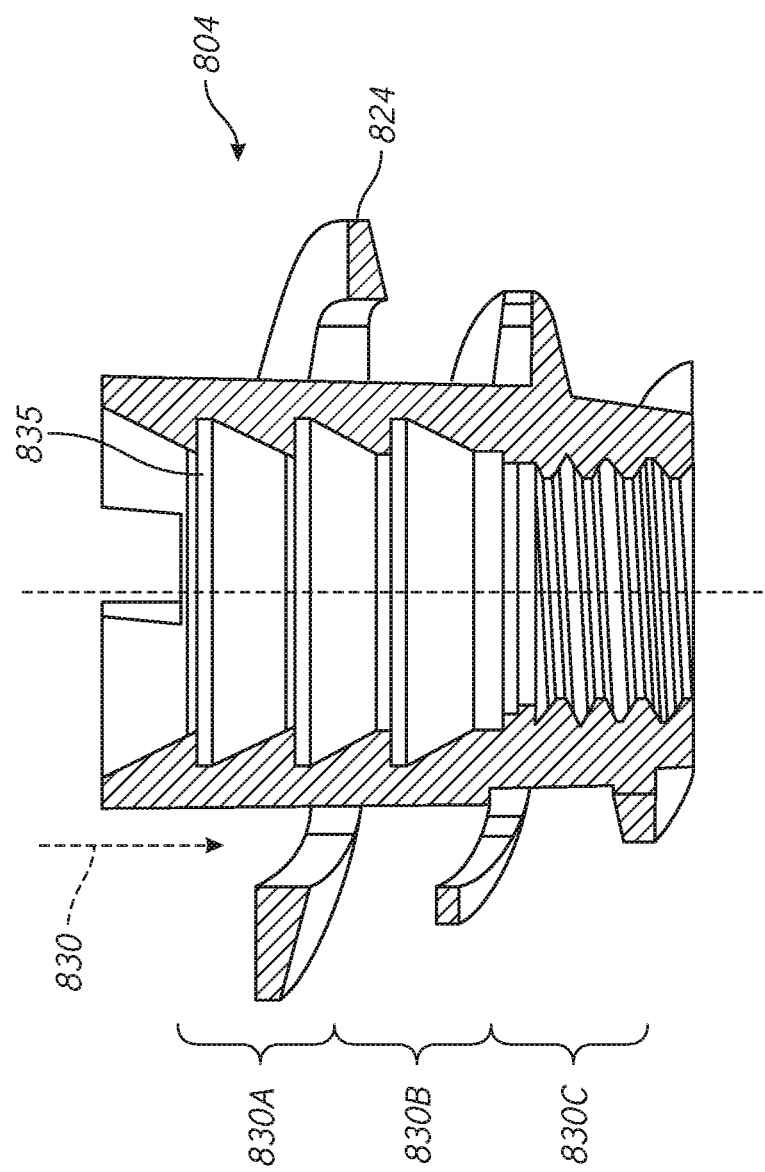
FIG. 26A shows aspects of a base member of the shoulder assembly of FIG. 22.

The base member 804 includes a first pathway 830 accessible from the lateral end 820 of the base member 804. The first pathway 830 is directed toward the medial end 816 through the helical structure 824. The first pathway 830 can be located adjacent to an inner periphery of the helical structure 824, as discussed above. The first pathway 830 can be partly defined by an outer surface of the body 812. The first pathway 830 can be disposed generally transverse to the helical structure 824. The first pathway 830 extends in a space 832 between successive portions of the helical structure 824. In one embodiment, a first segment 830A of the first pathway 830 is disposed through a proximal portion of the helical structure 824, a second segment 830B of the first path 830 is located medial of the first segment 830A, and a third segment 830C of the first path 830 is disposed medial of the second segment 830B. FIG. 26A shows the segments 830A, 830B, 830C of the path 830 in more detail.

FIG. 26A also shows that the base member 804 can include one or more barbs 835. The barbs 835 are configured to facilitate softer material attachment. In some embodiment the internal portion of the base member 804 couples with a structure made of a soft material, such as polyethylene. One example of such an assembly is an anatomic configuration where a convex articular surface may be coupled with the scapula using the base member 804. Another example is a reverse configuration with an inverse bearing surface (e.g. polyethylene glenoid sphere). The mode of connection between the base 804 and an articular or other component can include an interference fit between the barbs 835 and a projection of such component received in a space around which the barbs 835 are located, as described in connection with FIGS. 11A and 11B of WO2016/094739. In other embodiments the barbs 835 can be replaced with mating threads, mating threads and fins and/or mating fins, as described in connection with FIG. 5 of US20120221111. In other embodiments, the barbs 835 can be replaced by a groove and a C-ring or other deflectable member that spans between the base member 804 and an articular or other component as described in connection with FIGS. 4 and 5 of WO2014/067951. The entireties of each of WO2016/094739, US20120221111, and WO2014/067961, including the specific portions of each reference noted above are incorporated by reference herein.

The plate member 808 has a flange 842 and a first arm 846 that projects distally, medially away from or generally in a direction of implantation of the plate member 808 from the flange 842. The plate member 808 can have a second arm 846 that projects away from the flange 842. The first arm 846 is configured to be disposed in the first pathway 830 when the plate member 808 is disposed adjacent to the lateral end 820 of the base member 804. The first arm 846 is disposed through bone in the space 832 between successive portions of the helical structure 824 when the shoulder assembly 800 is implanted.

The plate member 808 also includes a boss 850 that extends laterally of the flange 842. The boss 850 comprises an arcuate outer periphery 854 and an aperture 858 that provides access to a lumen 862 through the aperture 858. The lumen 862 is defined by a tapered surface 864 that mates with a glenoid sphere 870, as discussed below. In another embodiment, the glenoid sphere 870 and the boss 850 are configured such that the glenoid sphere 870 coupled with the outer surface of the boss 850.

The glenoid sphere 870 comprises a recess 874 disposed on a medial side and a convex side 878 disposed opposite the recess 874. The glenoid sphere 870 has a tapered surface 882 disposed within the recess 874. The tapered surface 882 is partly disposed in the recess 874 and partly extends medially of the recess 874. The tapered surface 882 is disposed on a projection 890. The boss 850 receives the projection of the glenoid sphere 870 therein. The tapered surface 864 on the boss 850 mates with the tapered surface 882 on the medial side of the glenoid sphere 870 to form a connection between the glenoid sphere 870 and the plate member 808. The mating tapered surfaces 864, 882 can form a Morse taper connection between the glenoid sphere 870 and the plate member 808.

FIG. 26 illustrates further features of the shoulder assembly 800 that relate to connecting the components thereof together. The glenoid sphere 870 has a lateral opening 892 at the convex surface 878. The opening 892 extends to a lumen 894 that extends from the opening 892 to a medial opening 898. The lumen 894 includes a threaded zone 902 adjacent to the medial opening 898. The threaded zone 902 can be used to couple the glenoid sphere 870 with an inserter. That is the threaded zone 902 can be threaded onto a corresponding threaded tip of the inserter. While threads are shown, other couplers can be used, such as a bayonet coupling in place of or along with the threaded zone 902.

A fastener 910 is used to secure the glenoid sphere 870, the plate member 808, and the base member 804 together. The fastener 910 includes a medial end 914 with a threaded zone 918 and a lateral end 922. The lateral end 922 includes a tool interface 926.

The connection between the components of the shoulder assembly 900 is shown in FIG. 23. The base member 804 can be advanced into the glenoid g following preparations similar to that discussed in connection with of FIGS. 11-16. Once so placed, the plate member 808 can be advanced into the base member 804. The plate member 808 is advanced in a manner similar to the locking device 108. The arms 846 are advanced into the helical structure 824. Following placement of the plate member 808 into the base member 804, the glenoid sphere 870 can be mated to the plate member. The projection 890 can be advanced into the lumen 862 (see FIG. 26). Once the projection 890 is placed in the lumen 862 the fastener 910 can be advanced relative to the projection 890 and mated with the threaded zone 823. Further advancing of the fastener 910 into the threaded zone 823 induces a friction fit, e.g., a Morse taper, at the tapered surfaces 864, 882. In one embodiment, the threaded zone 918 of the fastener 910 engages first the threaded zone 902 of the glenoid sphere 870 and then mates with the threaded zone 823. In that embodiment, if the threaded zone 918 inadvertently disengage from the threaded zone 823 the back-out of the fastener 910 is limited such that the lateral end 922 of the fastener 910 does not protrude outside of the convex side 878 of the glenoid sphere 870. For example, even if the threaded zone 918 is disengaged form the threaded zone 834, lateral motion of the fastener 910 will be limited when a lateral end of the threaded zone 918 is disposed against a medial end of the threaded zone 902. When in this position, in one embodiment the distance between the lateral end of the threaded zone 918 and the lateral end 922 of the fastener 910 will be less than the distance within the lumen 894 from the lateral end of the threaded zone 902 to the convex side 878 of the glenoid sphere 870. Thus, the disengaged state of the fastener 910 will not result in the lateral end 922 protruding from the convex side 878.

The plate member 808 includes additional features for enhancing securement to the bone. The plate member 808 can includes one or more apertures 920. The apertures 920 can receive bone screws to enhance securement of the plate member 808 to the bone, e.g., to the scapula SC. Advantageously, the bone screw will lock into the apertures 920 by a thread engagement. In some embodiments, the locking mechanism will be multi-directional providing the possibility to lock the bone screws at a variable angle from the axis of the flange 842. Additionally, the medial side of the plate member 808 can includes a textured surface 924 e.g., coated or layered with a porous material in order to accelerate tissue ingrowth such as bony ingrowth. Advantageously, the plate member 808 could be manufactured by additive manufacturing to incorporate the porous surface 924.

Though shown in use to secure a hard material (e.g. ceramic, pyrocarbon, or metal) glenoid sphere 99 to a glenoid, the assembly 800 could be used to secure a soft-material (e.g. polyethylene, polyurethane, PEEK) glenoid sphere. Though shown in use to secure a glenoid sphere 99 to a glenoid, the assembly 800 could be used to secure an atomic glenoid. Though shown in use to secure a glenoid sphere 99 to a glenoid, the assembly 800 could be used in other anatomy to achieve very secure connection to relatively shallow layers of bone, which can include cancellous bone that is exposed during a procedure.

B. Applications to Other Boned & Joints

Figure 27:
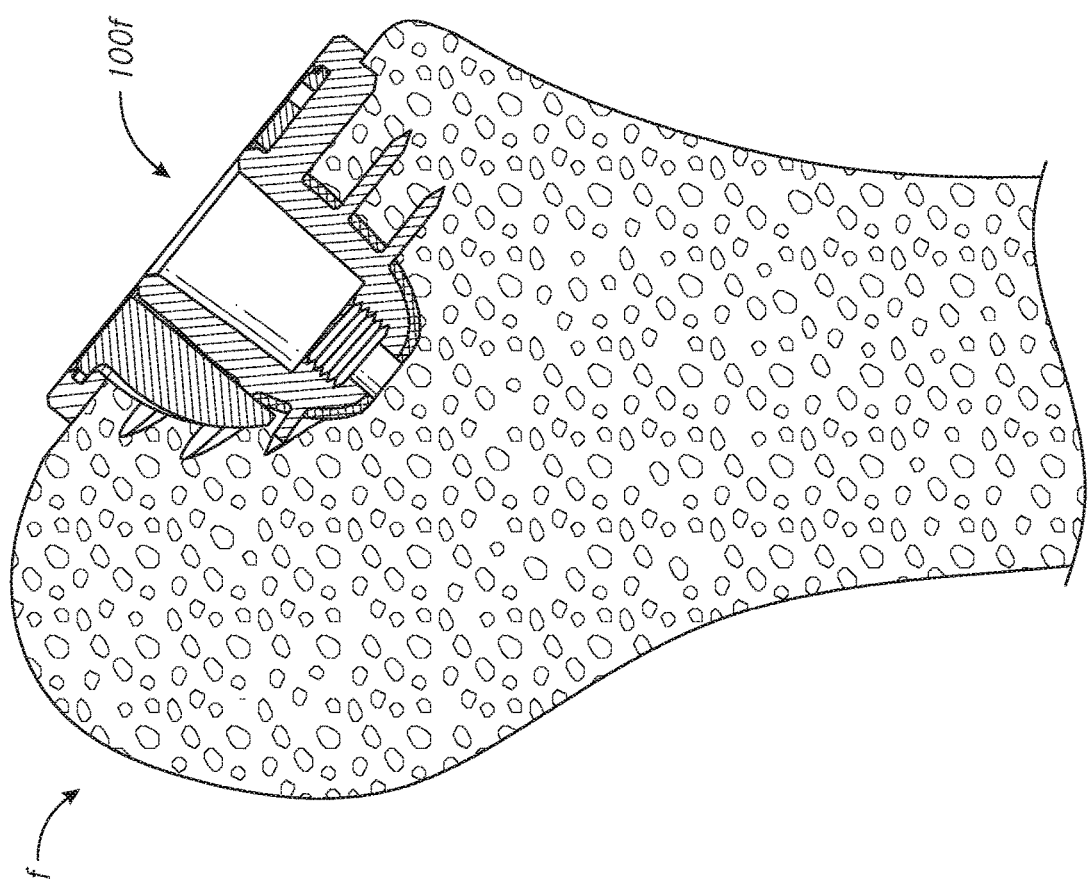
FIG. 27 is a schematic side view of a proximal femur having a prosthesis assembly similar to that of FIGS. 4-10 disposed therein in connection with a hip joint procedure.
Figure 28:
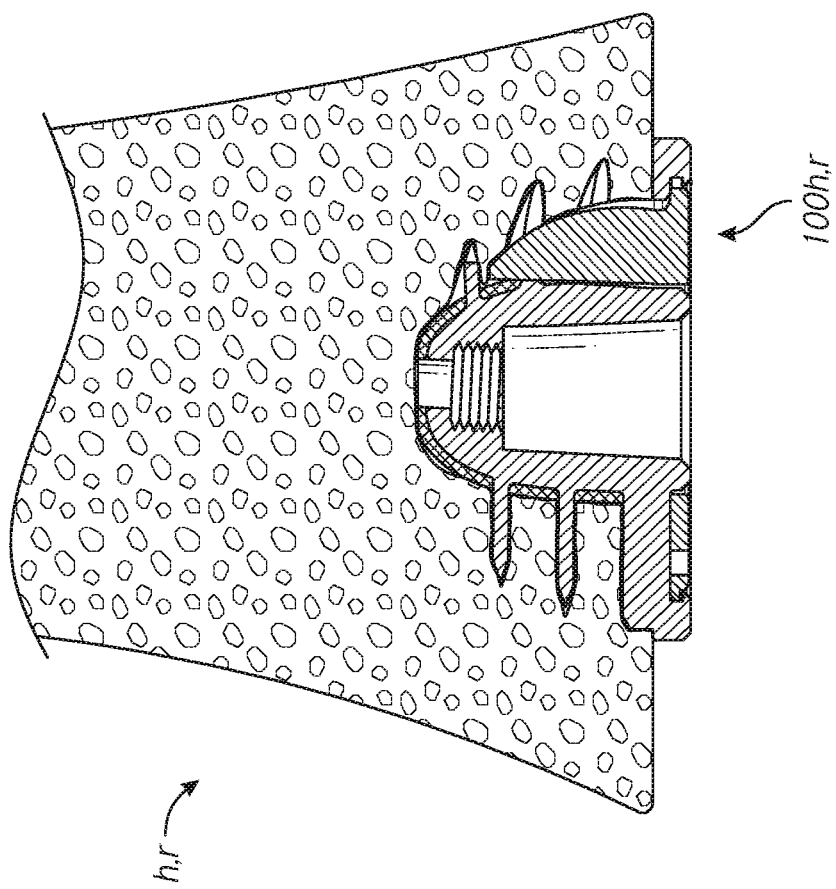
FIG. 28 is a schematic side view of a distal portion of a long bone of an arm, e.g., of the humerus or radius, having a prosthesis assembly similar to that of FIGS. 4-10 disposed therein in connection with an elbow or wrist joint procedure.
Figure 29:
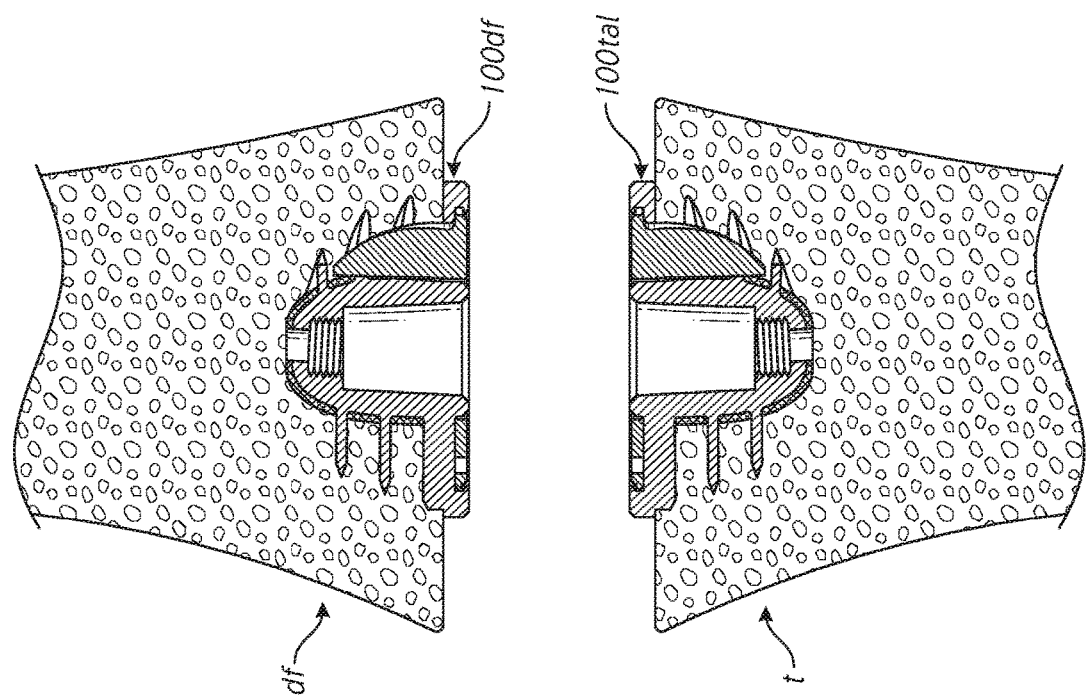
FIG. 29 is a schematic side view of a knee joint showing a prosthesis assembly similar to that of FIGS. 4-10 disposed in the distal femur and in the proximal tibia thereof.

FIGS. 27-29 show a number of other applications for the prosthesis assemblies described herein. In particular, the shoulder assemblies 100, 800 can be applied to other bones and joints.

FIG. 27 shows that a proximal femur f can be fitted with a prosthesis assembly 100*f* similar to the prosthesis assembly 100. The prosthesis assembly 100*f* is different from the shoulder assembly 100 in that it would be configured more particularly for the proximal femur.

FIG. 28 shows that a distal humerus h or to a distal radius r can be fitted with a prosthesis assembly 100*h*, *r* similar to the prosthesis assembly 100. The prosthesis assembly 100*h*, *r* is different from the shoulder assembly 100 in that it would be configured more particularly for the distal humerus or radius.

FIG. 29 shows that a distal femur df and/or to a proximal tibia t can be fitted with a prosthesis assembly 100*df*, 100*t* similar to the prosthesis assembly 100. The prosthesis assemblies 100*df, t*, are different from the shoulder assembly 100 in that they would be configured more particularly for the distal femur or proximal tibia. Also, on both side of the knee joint, implant sizing such as threads external diameter, core diameter, overall length could be sized according to patient anatomy per pre-operative planning based on CT-scan, MRI or any other medical images modality.

Figure 30:
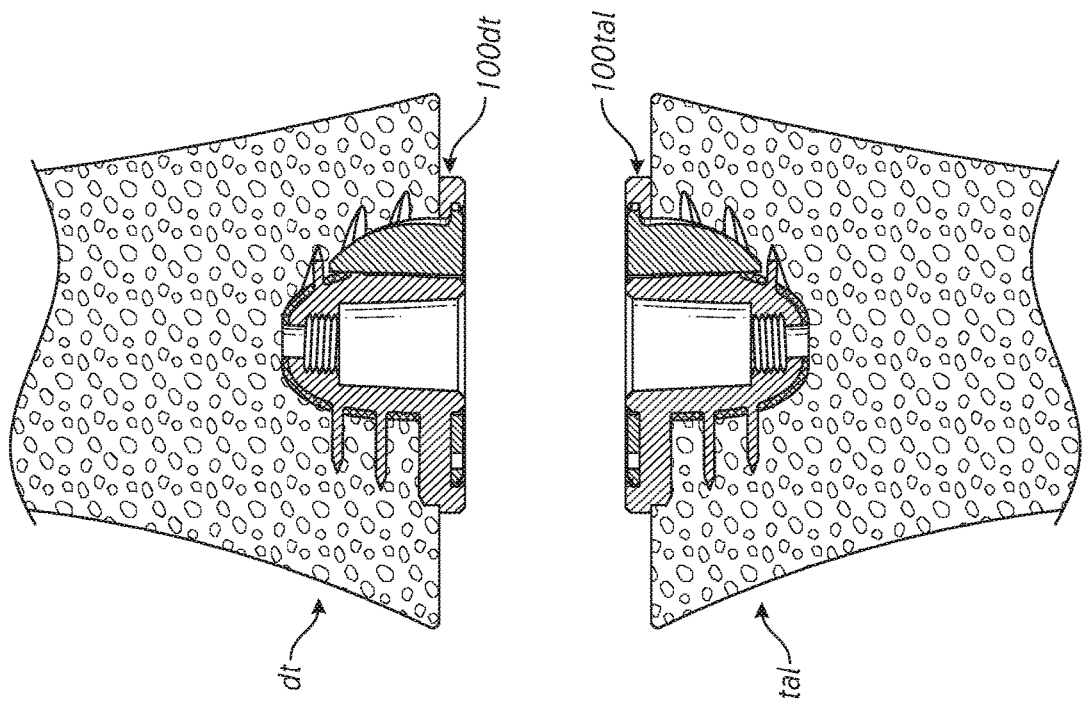
FIG. 30 is a schematic side view of an ankle joint showing a prosthesis assembly similar to that of FIGS. 4-11 disposed in the distal tibia and in the proximal talus thereof.

FIG. 30 shows that a distal tibia dt and/or to a proximal talus tal can be fitted with a prosthesis assembly 100*dt*, 100*tal* similar to the prosthesis assembly 100. The prosthesis assemblies 100*dt, tal*, are different from the shoulder assembly 100 in that they would be configured more particularly for the distal tibia or proximal talus. Also, on both side of the ankle joint, implant sizing such as threads external diameter, core diameter, overall length could be sized according to patient anatomy per pre-operative planning based on CT-scan, MRI or any other medical images modality.

Each of the applications illustrated in FIGS. 27-29 can employ the prosthesis assembly 800 with modifications similar to those discussed above in connection with the prosthesis assemblies 100*h*, 100*r*, 100*f*, and 100*t*.

VII. Performance of Embodiments Disclosed Herein

Figure 31:
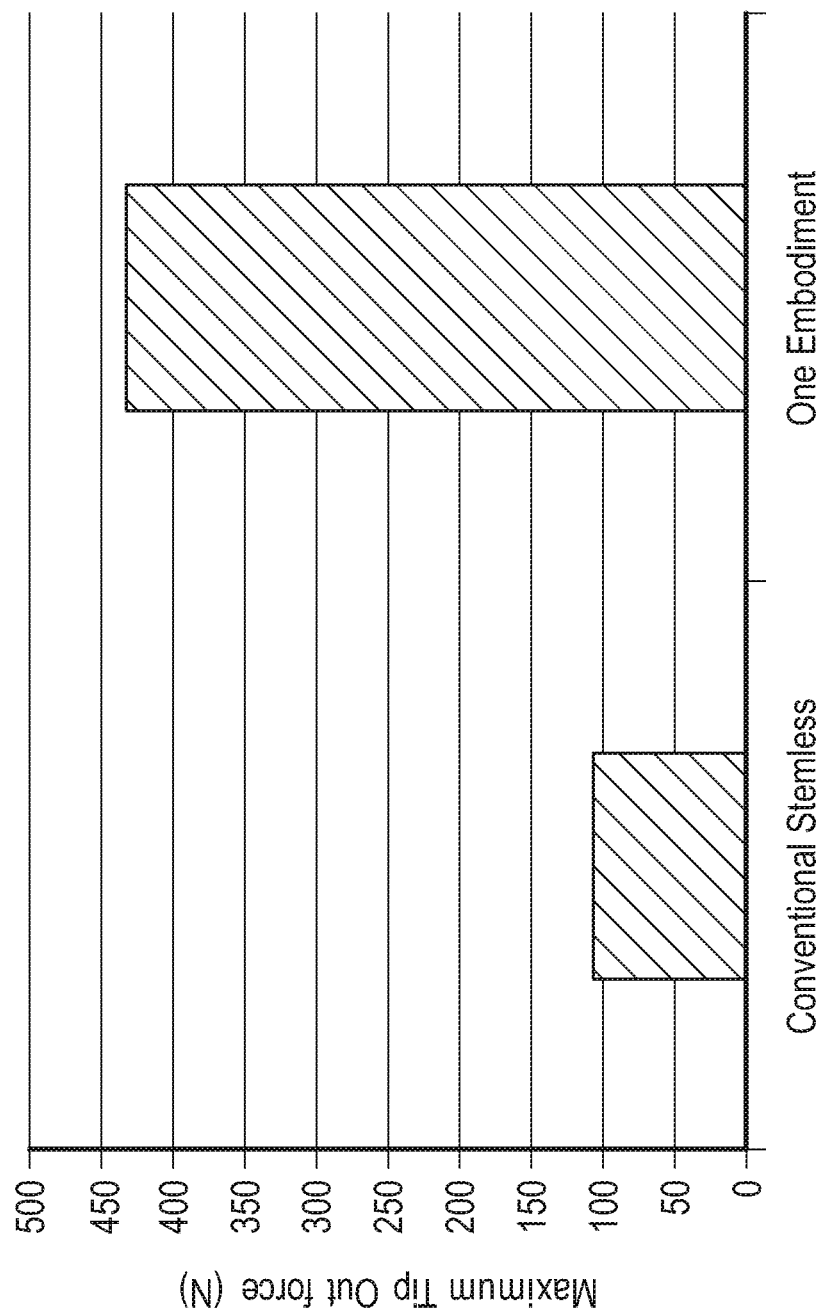
FIG. 31 shows comparative tip out performance of an embodiment as disclosed herein compared to a conventional stemless implant.

FIG. 31 shows comparative performance of embodiments disclosed herein with respect to a stemless apparatus that does not have the helical structures disclosed herein nor the locking devices. The graph shows maximum tip out force which is measured by applying an off axis load at a known or prescribed fixed distance from a surface at or to which a shoulder assembly similar to the assembly 100 was implanted. The tip out force represents the resistance of the device to tipping out or becoming dislodge from the surface when subject to off axis loading. The forces were observed using a load cell or force transducer. As can be seen, the force of one embodiment is more than four times the force that would dislodge the conventional stemless component. This represents a significant improvement in the retention of the apparatuses disclosed herein compared to conventional stemless design which rely to a large extent on ingrowth for securement which can be sufficient some time after implantation but which can be subject to dislodgement prior to full integration by ingrowth.

VIII. Stress Shielding Reduction Members

As discussed above, a problem that can arise in orthopedic implant is stress shielding. This is a condition where stresses are prevented from being applied anywhere around a prosthetic implant, including at a resection surface. FIG. 32 illustrates a shoulder assembly 100B in which one or more components is made patient specific to reduce minimize or eliminate erosion due to stress shielding.

The shoulder assembly 100B includes an articular body 948 and a shoulder assembly 950. The shoulder assembly 950 includes a base member 104D and the locking device 108. The base member 104D is similar to any of the base members 104, 104A, 104B, 104C except as described differently below. Because of the similarities, the description of the features that are consistent will not be repeated. As discussed above in connection with FIGS. 6A-1, 6A-2, and 6A-3, the base member 104D can have at least a portion thereof adapted for a specific patient based upon pre-operative imaging. The locking device 108 also or alternatively can have at least a portion thereof adapted for a specific patient based upon pre-operative imaging. The shoulder assembly 900 includes a trunnion 954 that is configured to reduce, minimize or eliminate stress shielding.

Figure 32A:
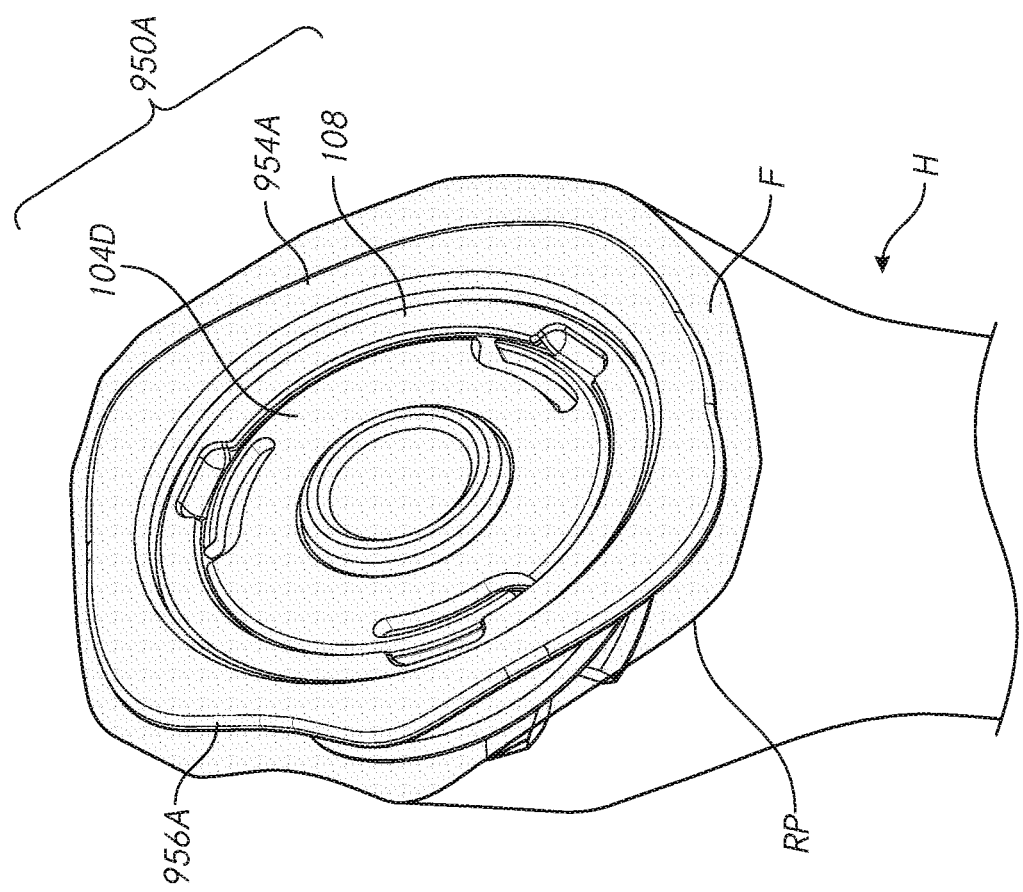
FIG. 32I illustrates a method of implanting the shoulder assemblies of FIGS. 32-32H.
FIG. 32J illustrates another embodiment of a shoulder assembly configured to reduce or eliminate stress shielding in a resected humerus.

FIG. 32 shows that the trunnion 954 can extend from a part of the base member 104D. FIG. 32C shows that the trunnion 954 can be coupled with the collar 220 of the base member 104D. The trunnion 954 can extend between the collar 220 and the perimeter RP of the humerus H at the face F. In one embodiment, the trunnion 954 includes an inner periphery 955 and an outer periphery 956. The inner periphery 955 can be configured to mate with the collar 220 as discussed further below. The outer periphery 956 can be sized to match or nearly match the perimeter RP of the face F at the resection plane. The outer periphery 956 can be circular with a diameter that is tangential or nearly tangential to the portion of the perimeter RP that is closest to the center of the bore B to which the shoulder assembly 950 is mated.

Figure 32B:
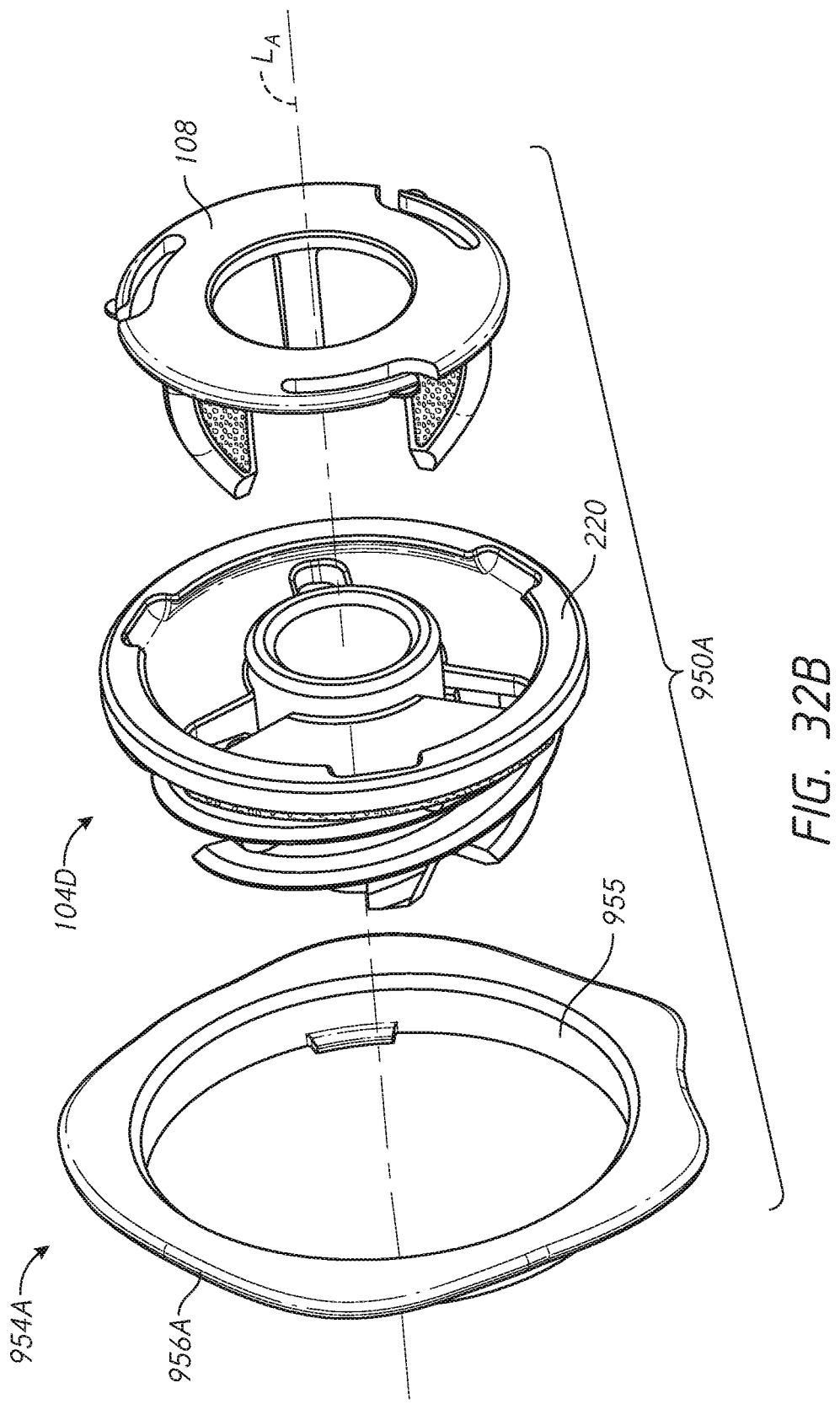
Figure 32C:
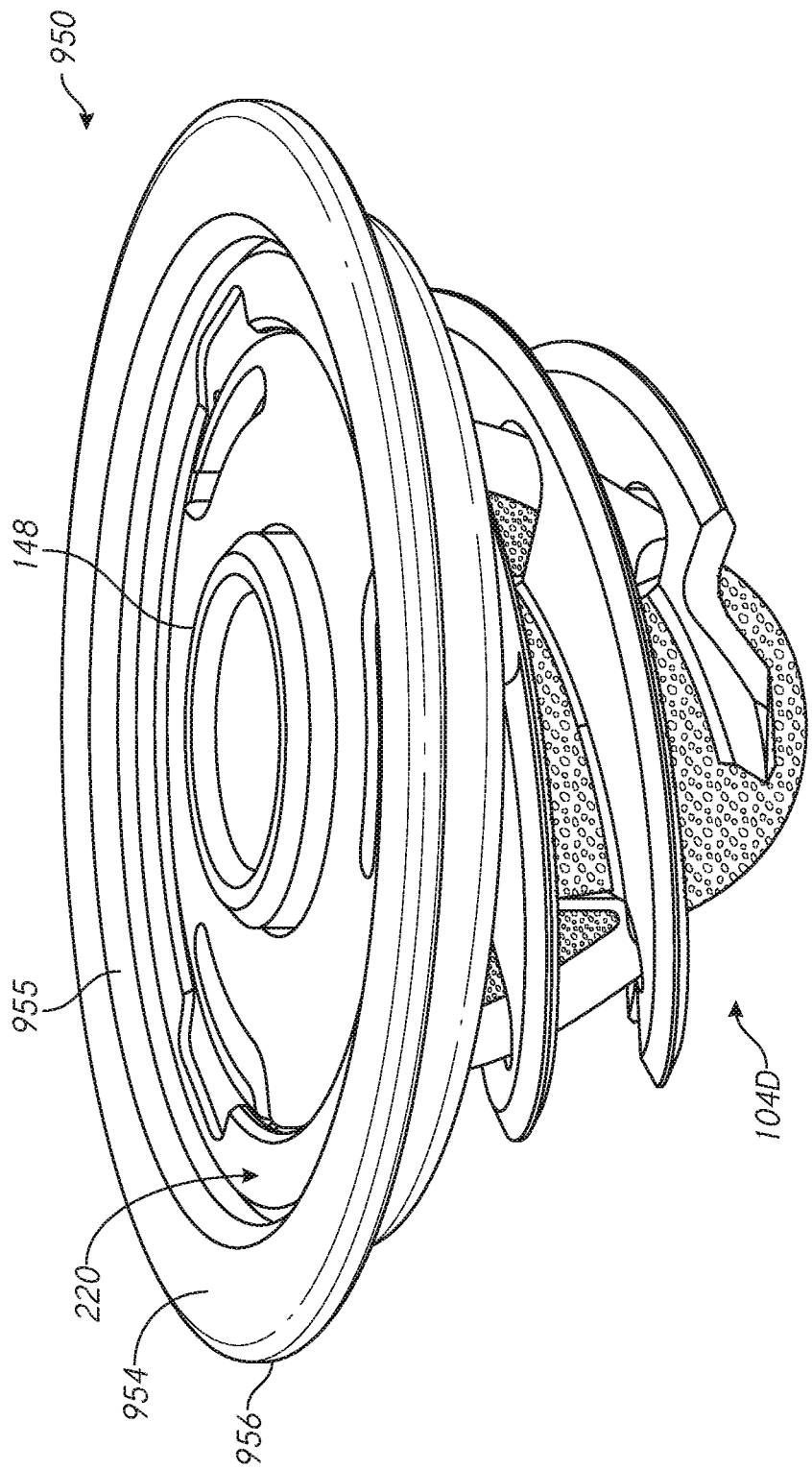
Figure 32D:
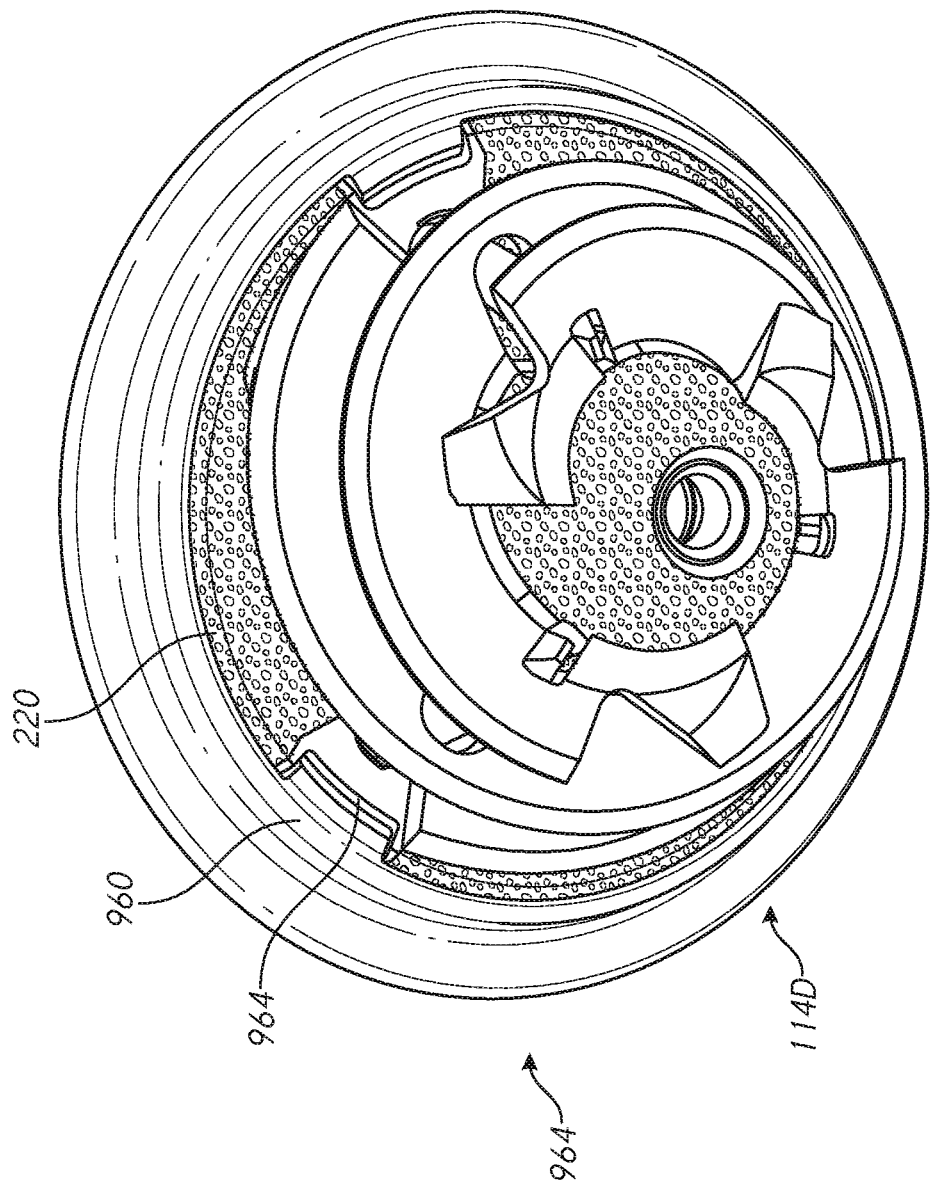
Figure 32E:
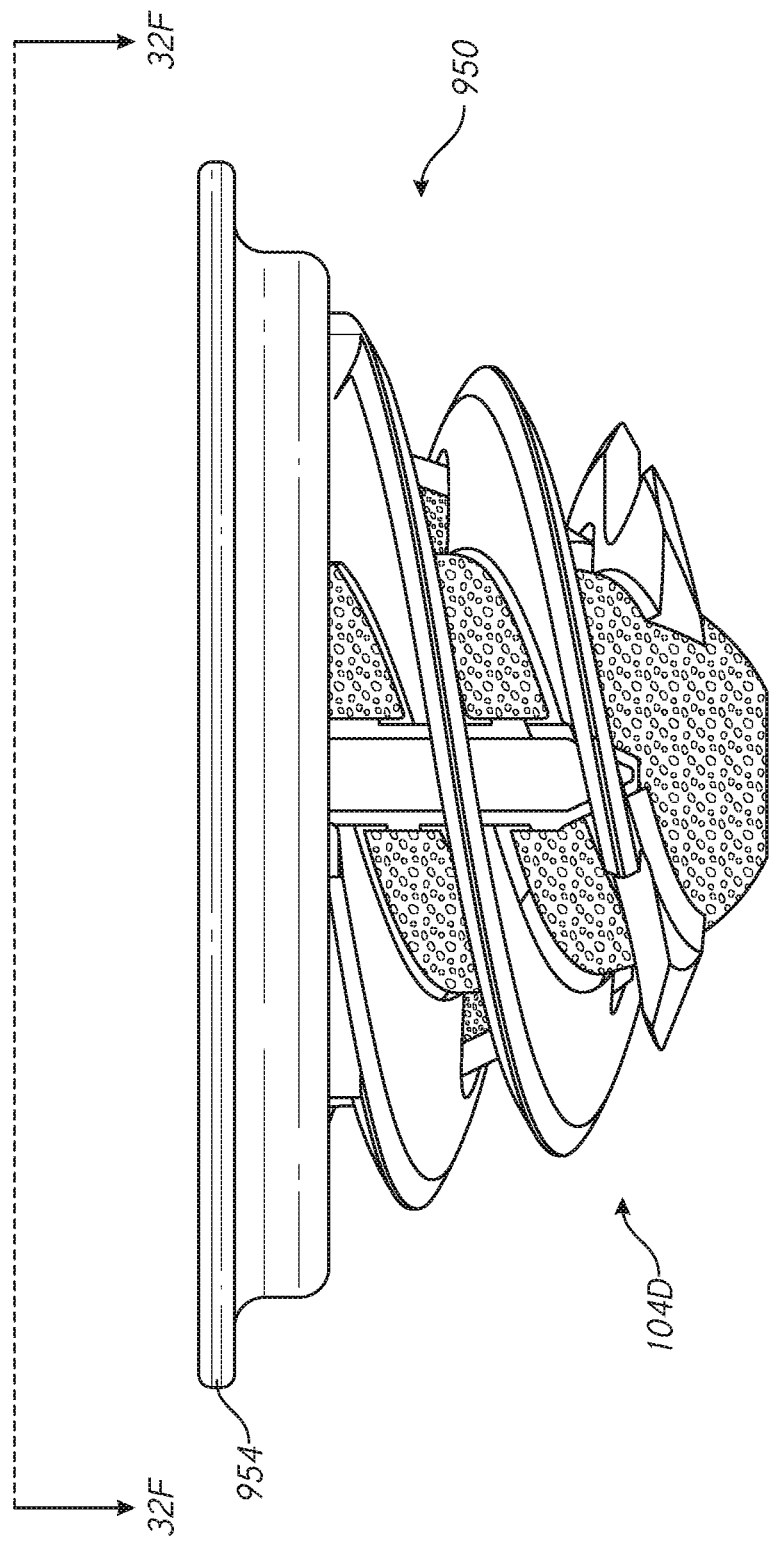

FIG. 32B shows a shoulder assembly 950A that is similar to the shoulder assembly 950 except as described differently. FIG. 32B shows that the shoulder assembly 950A comprises a three component assembly. The one embodiment comprises a trunnion 954A that is the outermost component in the radial direction (e.g., transverse to the longitudinal axis LA). The base member 104D is located inward of the trunnion 954A. The locking device 108 is advanced into the base member 104D in the manner discussed above. The trunnion 954A has an outer periphery 956A that is adapted for a specific patient based upon pre-operative imaging. For example, as shown in FIG. 32A the outer periphery 956A can have a shape that matches the shape of the perimeter RP of the face F. The outer periphery 956A can be non-round. The outer periphery 956A can have can have one or more concavities or flat edges that face radially outwardly or away from the inner periphery 955. The outer periphery 956A can have can have multiple convexities of different curvature to enable the outer periphery to extend further radially outward in certain regions than in other regions.

The size and or shape of the trunnion 954, trunnion 954A can be such as to cover any or all portions of the face F that could be subject to erosion if exposed to stress shielding. The trunnion 954, trunnion 954A can be configured to extend, for example toward or completely cover the medial calcar MC or other zone that could undergo erosion. The trunnion 954, trunnion 954A can be moved into engagement with the face F and can even be caused to put initial or continuing pressure on the cancellous bone that is exposed following resection of the head of the humerus H. By making the trunnion 954 and the trunnion 954A patient specific, as discussed above, sufficient coverage of such regions without overhanging the perimeter RP of the face F can be achieved.

Figure 32F:
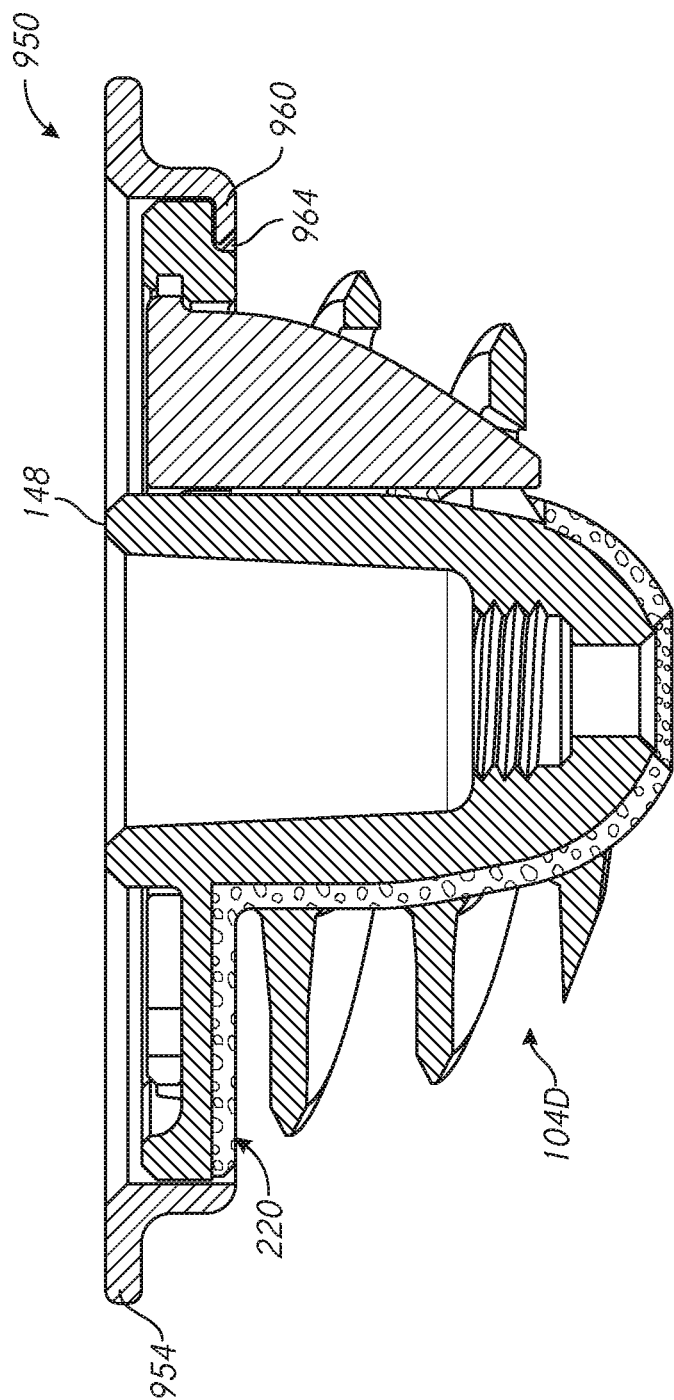
Figure 32G:
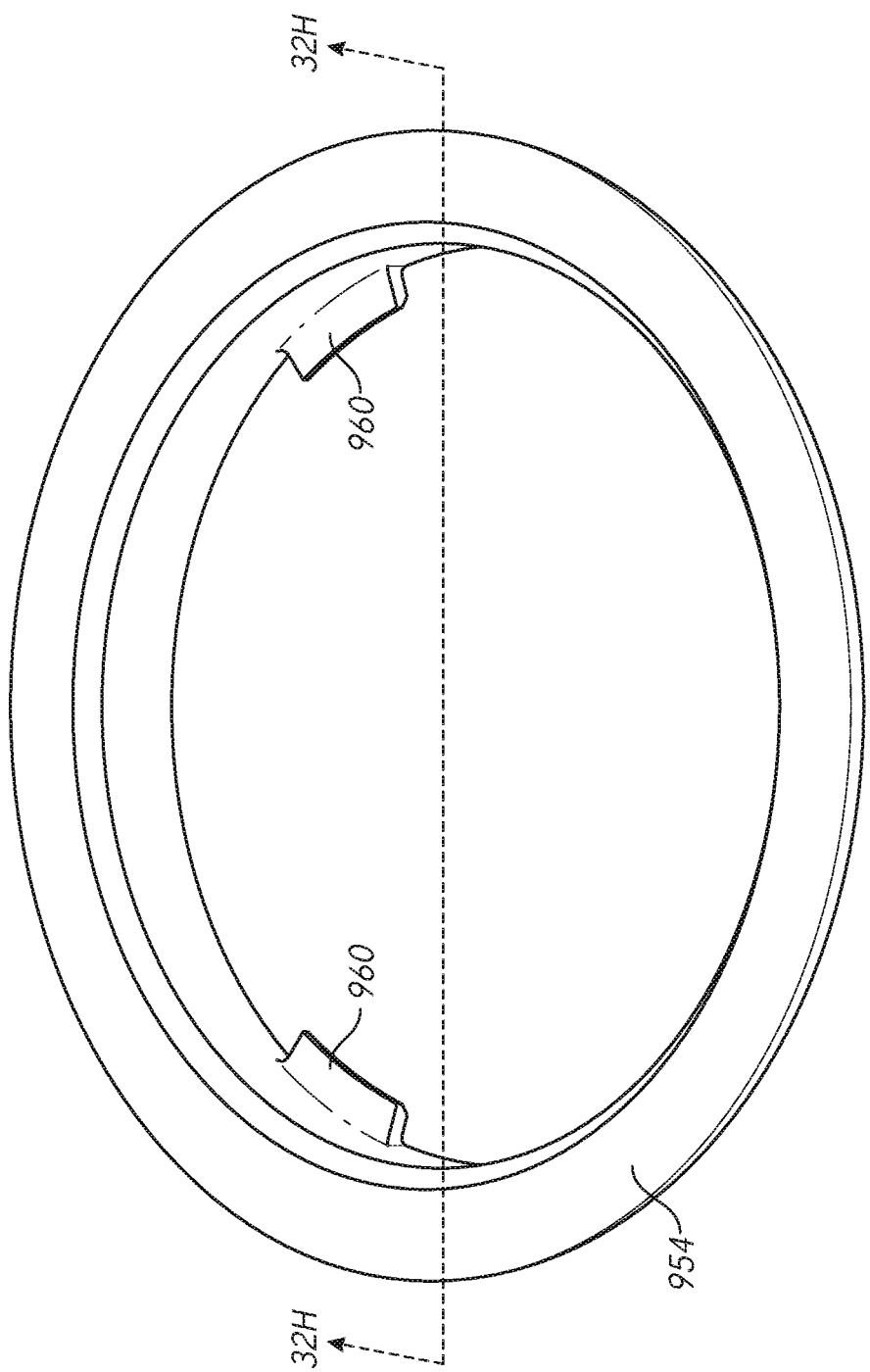
Figure 32H:
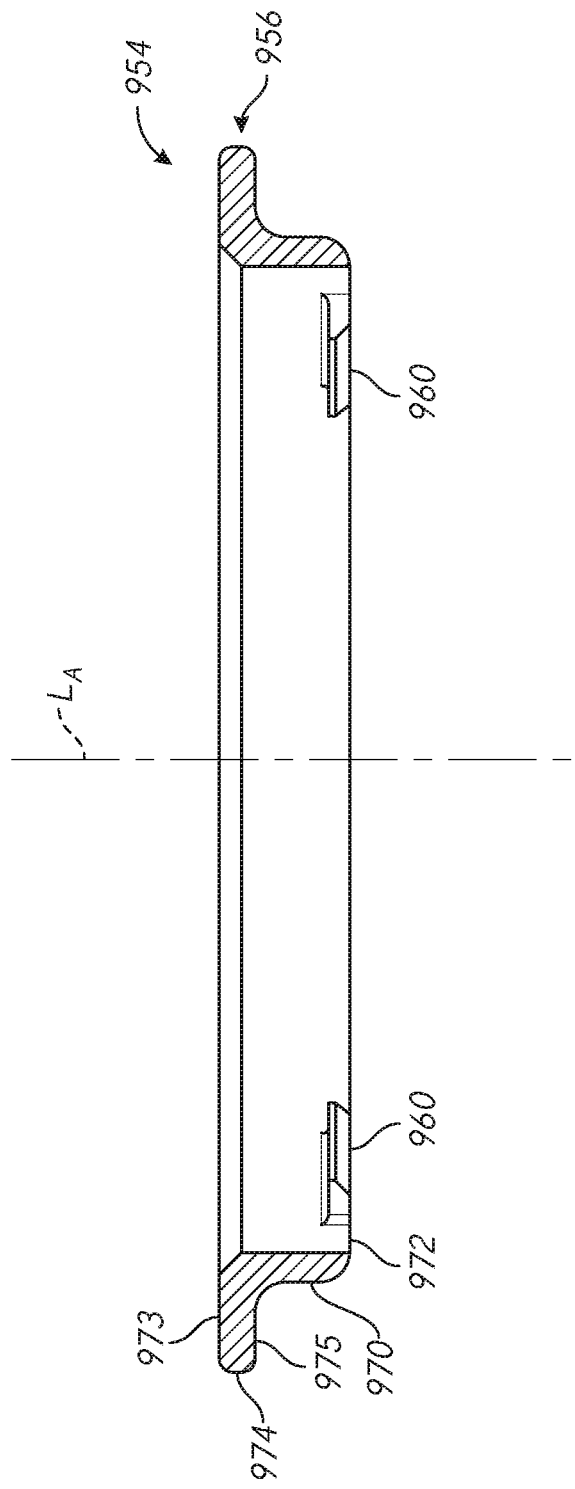

FIGS. 32F-32H show further structure of the trunnion 954 or the trunnion 954A. The trunnion 954 or trunnion 954A includes a wall 970 that projects in the direction of the longitudinal axis LA of the shoulder assembly 950 or shoulder assembly 950A. The wall 970 can surround a cylindrical space that can contain the collar 220 of the base member 104D. A first edge 972 can be aligned with an edge of the collar 220 that faces the first end 204. In some embodiments, the radial projection 960 can be aligned to the first edge 972. The radial projection 960 then act both as anti-rotation elements between the trunnion 954 and the base member 104E but also as an axial stop causing the position along the longitudinal axis LA of the base member 104E to the trunnion 954 to be controlled. A second edge 973 can be disposed opposite the first edge. The second edge 973 can be located along the longitudinal axis LA aligned with the inner raised portion 148 when the base member 104E is assembled to the trunnion 954 (see FIG. 32F). This configuration prevents the trunnion 954 from interfering with securing the articular component 4 to the humerus H. The trunnion 954 also includes a lateral flange portion 974 that extend radially away from the wall 970. The flange portion 974 can extend radially by an amount that varies around the circumference, as discussed above such that the shape of the outer periphery 956 can be non-circular as needed to provide sufficient or full coverage of the face F of the humerus H at the resection. The flange portion 974 can define a third surface 975 that extends between the wall 970 and the outer periphery 956. The third surface 975 can face the first surface 972 and can be configured to be placed in contact with the face F of the humerus H at the resection. The third surface 975 can be porous or otherwise configured to enhance ingrowth of the bone. The third surface 975 can be a porous surface.

FIGS. 32D and 32F-32H illustrate one way in which the trunnion 954 or the trunnion 954A and the base member 104D can be coupled together. The inner periphery 955 of the trunnion 954 can have a radial projection 960. The radial projection 960 can extend radially inwardly of the inner periphery 955 toward the center of the trunnion 954. The radial projection 960 can extend about one-half the radial extent of the collar 220. The collar 220 can have a radial recess 964 that is configured to receive the radial projection 960. The circumferential extent of the radial projection 960 preferably is a bit less than that of the radial recess 964. The radial projection 960 can extend along a circumferential arc subtending about 5 degrees, about 10 degrees, about 15 degrees or up to about 20 degrees.

Figure 32I:
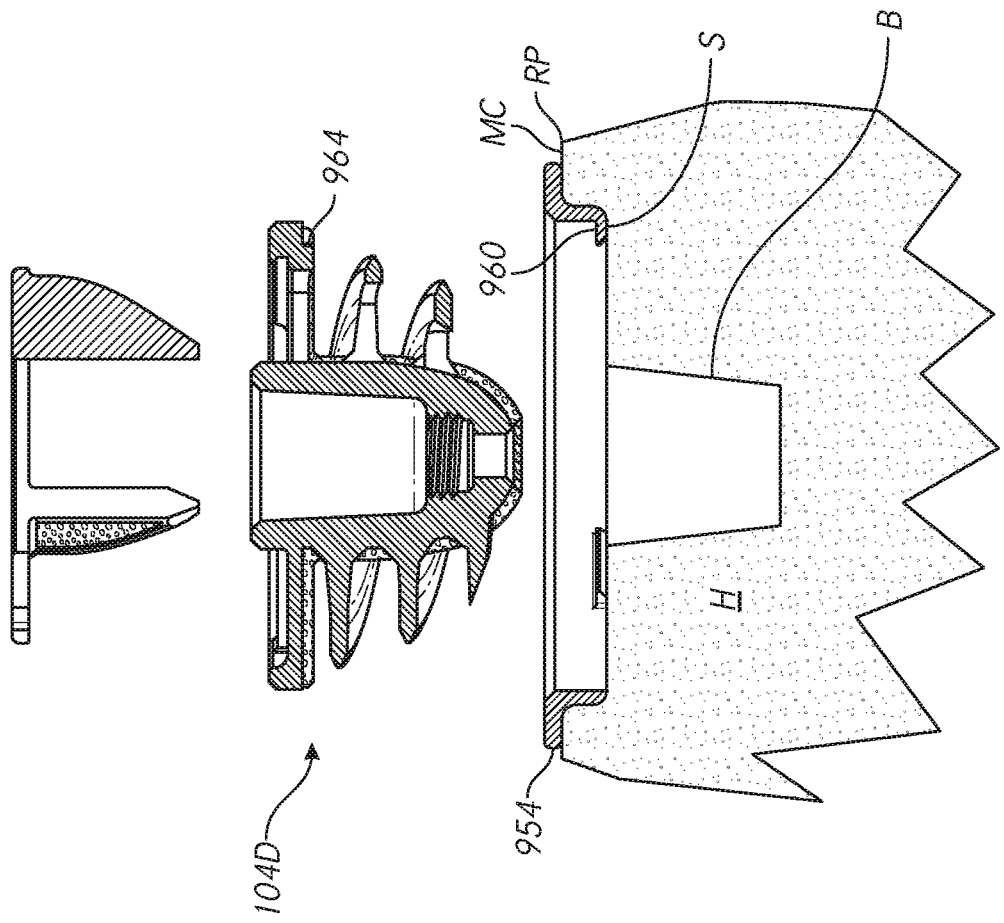

FIG. 32I supplements the method discussion above in FIGS. 11-19. FIG. 32I shows a portion of a method following resection of the humerus H. Thereafter the bore B and the recessed surface S can be formed. Thereafter the trunnion 954 can be advanced into the recessed surface S to contact the bone. This can be done by hand or by instrument. The trunnion 954 does not need to be impacted into the bone but can be in some techniques. Thereafter, the base member 104D can be advanced to the face F and into contact with the boundary between the recessed surface S and the bore B. The base member 104D can be further advanced until the helical structure(s) 224 engage the face F. Further rotation of the base member 104D pulls the base member 104D into the bone and eventually into contact with the trunnion 954. Further rotation of the base member 104D relative to the trunnion 954 causes the base member 104D to rotate to a position where the radial projections 960 are nearly rotationally aligned with the radial recesses 964. As the base member 104D further rotates the radial projection 960 become nested in the radial recess 964 as shown in FIG. 32F. At this point, the base member 104D applies a compression of the trunnion 954 against the bone surface between the recessed surface S and the perimeter RP. This compression not only reduces, minimizes or eliminates stress shielding but also creates positive compression of the bone in this area. As shown in FIG. 32I this can cause the medial calcar MC to be covered and even compressed by the trunnion 954. In variations, the trunnion 954 and the trunnion 954A can have a roughened or porous surface or other configuration that encourages bone ingrowth to the surface from the face F.

In further variations, the connection between the trunnion and the base can be modified. For example, a trunnion 954B can be provided that comprises an annular projection 960A. The annular projection 960A can comprise a circular lip that extends a greater distance around the inner periphery 955 of the trunnion 954B. The annular projection 960A can extend entirely around the inner periphery 955 of the trunnion 954B. The trunnion 954B can be mated with a base member 104E that is similar to the base member 104D except as described differently. The base member 104D can, include an annular recess 964A. The annular recess 964A can extend around a peripheral portion of the base member 104E at a location between the first end 204 and the second end 208 thereof. The annular recess 964A can face the direction of the first end 204. In one embodiment the annular recess 964A extends entirely around the periphery of the base member 104E. The base member 104E and the trunnion 954B are advantageous in that the base member 104E can be rotated into engagement with the trunnion 954B and such rotation can stop at any point providing sufficiently secure connection therebetween and/or sufficient loading of the face F at the resection plane. In the case of mating the radial projection 960 to the radial recess 964, in some cases the surgeon will choose between whether to advance the base member 104D another one-third turn to move the radial projection 960 to the next radial recess 964. This could cause more bone loading than desired. In further variations of the base member 104D and the trunnion 954 more or less than three radial projections 960 are mated with more or less than three radial recesses 964. For example, there can be one, two, four, five, six, seven or eight radial projection 960 that mate with one, two, four, five, six, seven or eight radial recesses 964.

As used herein, the relative terms "proximal" and "distal" shall be defined from the perspective of the humeral shoulder assembly. Thus, distal refers the direction of the end of the humeral shoulder assembly embedded in the humerus, while proximal refers to the direction of the end of the humeral shoulder assembly facing the glenoid cavity when the assembly is applied to the humerus. Distal refers the direction of the end of the humeral shoulder assembly embedded in the scapula, while proximal refers to the direction of the end of the humeral shoulder assembly facing the humerus when the assembly is applied to the glenoid. In the context of a glenoid component, the distal end is also sometimes referred to as a medial end and the proximal end is sometimes referred to as a lateral end.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A stemless humeral anchor, comprising:
    a first end configured to be embedded in an exposed face of a resection plane of a proximal portion of a resected humerus and a second end opposite the first end, wherein the face of the resection plane has a perimeter;
    a mating portion comprising a central recess extending from the second end toward the first end;
    a collar disposed at the second end around the mating portion and extending generally transverse to a longitudinal axis of the recess,
        wherein outer periphery of the collar is configured to have a shape that closely matches the shape of the perimeter of the face of the resection plane of the humerus, and
        wherein the collar is configured to extend to, or extend nearly to, the perimeter of the face of the resection plane of the humerus when the stemless humeral anchor is placed in the face of the resection plane; and
    a plurality of rotation control features disposed between the collar and the first end, wherein the rotation control features are configured to resist rotation of the stemless humeral anchor when the stemless humeral anchor is implanted;

a void filling protrusion disposed between the collar and the first end of the anchor, wherein the void filling protrusion;
(1) is configured as a structure protruding and extending from one of the plurality of rotation control features toward a neighboring second one of the plurality of rotation control features, wherein the void filling protrusion is contiguous with said one of the plurality of rotation control features; or
(2) is configured as a radial protrusion from the mating portion;
wherein at least a portion of the stemless humeral anchor is adapted for the humerus based upon pre-operative imaging.

2. The stemless humeral anchor of claim 1, wherein the collar extends to, or extends nearly to, the perimeter of the face of the resection plane of the humerus transverse to a longitudinal axis of the recess so that a periphery of the collar covers at least the medial calcar of the humerus.

3. The stemless humeral anchor of claim 1, wherein the collar extends to, or extends nearly to, the perimeter of the face of the resection plane of the humerus transverse to a longitudinal axis of the recess so that a periphery of the collar covers substantially the entire exposed face of the resection plane of the humerus.

4. The stemless humeral anchor of claim 1, wherein the void filing protrusion comprises a porous shell.

5. The stemless humeral anchor of claim 4, wherein the porous shell includes a thickness in a range of 0.75 mm to 1 mm thick and pore size in a range of 100 microns to 1000 microns.

6. A kit comprising:
the stemless humeral anchor of claim 1; and
a bone void filling component configured to be disposed in the void filling protrusion.

7. The stemless humeral anchor of claim 1, wherein at least one of the rotation control features comprises a larger radial extent than at least one other of the rotation control features, based on the volume of bone of a corresponding portion of the humerus of the specific patient as determined from pre-operative imaging.

8. The stemless humeral anchor of claim 1, wherein each of the rotation control features have a first end coupled with the first end of the anchor and a second end disposed away from the first end of the anchor toward the second end of the anchor.

9. The stemless humeral anchor of claim 1, wherein each of the rotation control features have a first end coupled with the first end of the anchor and a second end coupled with the collar adjacent to the second end of the anchor.

10. The stemless humeral anchor of claim 1, wherein each of the rotation control features have a first end and a second end, the second end being coupled with the collar and the first end disposed away from the second end of the anchor toward the first end of the anchor.

11. The stemless humeral anchor of claim 1, wherein each of the rotation control features projecting from the mating portion and from the collar distally of the collar.

12. The stemless humeral anchor of claim 1, wherein the collar is configured to rest on an exposed face following resection of a humerus.

13. The stemless humeral anchor of claim 1, wherein the collar is configured such that when properly applied to the humerus, a maximum gap threshold between the collar and the resection plane of humerus is not exceeded along the entire circumference of the collar.

14. The stemless humeral anchor of claim 13, wherein the maximum gap is larger between the outer periphery of the collar and the perimeter of the resection plane of the humerus in zones not subject to stress shielding erosion.

15. The stemless humeral anchor of claim 13, wherein the maximum gap is 4 mm or less, between the outer periphery of the collar and the resection plane of the humerus at the medial calcar zone.

16. The stemless humeral anchor of claim 13, wherein the maximum gap is 2 mm or less between the outer periphery of the collar and the resection plane of the humerus at the medial calcar zone.

17. The stemless humeral anchor of claim 13, wherein the maximum gap is 1 mm or less between the outer periphery of the collar and the resection plane of the humerus at the medial calcar zone.

18. The stemless humeral anchor of claim 1, wherein when the void filling protrusion is configured as a structure protruding and extending from one of the plurality of rotation control features toward a neighboring second one of the plurality of rotation control features, the void filling protrusion is contiguous with said one of the rotation control features.

19. The stemless humeral anchor of claim 1, wherein when the void filling protrusion is configured as a structure protruding and extending from one of the plurality of rotation control features toward a neighboring second one of the plurality of rotation control features,
the stemless humeral anchor further comprises a second void filling protrusion disposed between the collar and the first end of the anchor and protruding and extending from another one of the plurality of rotation control features toward one of the plurality of rotation control features that is neighboring said another one of the plurality of rotation control features, wherein the second void filling protrusion is contiguous with said another one of the plurality of rotation control features.

20. The stemless humeral anchor of claim 19, wherein the two void filling protrusions have different shapes.

21. The stemless humeral anchor of claim 1, wherein when the void filling protrusion is configured as a structure protruding and extending from one of the plurality of rotation control features toward a neighboring one of the plurality of rotation control features,
the stemless humeral anchor further comprises a second void filling protrusion that is configured as a radial protrusion from the mating portion.

22. The stemless humeral anchor of claim 21, wherein the two void filling protrusions have different shapes.

23. The stemless humeral anchor of claim 1, wherein when the void filling protrusion is configured as a radial protrusion from the mating portion, the stemless humeral anchor further comprises a second void filling protrusion that is configured as a radial protrusion from the mating portion.

24. The stemless humeral anchor of claim 23, wherein the two void filling protrusions have different shapes.

* * * * *